US009927337B2

(12) United States Patent
Kombolias

(10) Patent No.: US 9,927,337 B2
(45) Date of Patent: Mar. 27, 2018

(54) SYSTEMS AND METHODS FOR DETERMINING ADHESIVE STRENGTH

(71) Applicant: U.S.A. as represented by Government Publishing Off, Washington, DC (US)

(72) Inventor: Mary Kombolias, Washington, DC (US)

(73) Assignee: The United States of America as Represented by the Government Publishing Office, Washington, DC (US)

( * ) Notice: Subject to any disclaimer, the term of this patent is extended or adjusted under 35 U.S.C. 154(b) by 1 day.

(21) Appl. No.: 14/755,704

(22) Filed: Jun. 30, 2015

(65) Prior Publication Data

US 2016/0003722 A1 Jan. 7, 2016

Related U.S. Application Data

(60) Provisional application No. 62/019,587, filed on Jul. 1, 2014.

(51) Int. Cl.
*G01N 3/08* (2006.01)
*G01N 19/04* (2006.01)

(52) U.S. Cl.
CPC .............. *G01N 3/08* (2013.01); *G01N 19/04* (2013.01); *G01N 2203/0091* (2013.01)

(58) Field of Classification Search
CPC ........................ G01N 19/04; G01N 2203/0091
See application file for complete search history.

(56) References Cited

U.S. PATENT DOCUMENTS

| 7,833,576 | B2 | 11/2010 | Storbeck et al. | |
| 2002/0007014 | A1* | 1/2002 | Hyde | A61L 15/585 525/191 |
| 2004/0146712 | A1 | 7/2004 | Obeng | |
| 2013/0042966 | A1* | 2/2013 | Look | B32B 37/12 156/227 |

OTHER PUBLICATIONS

ANSI INCITS 322-2008 Information Technology Card Durability Test Methods, Information Technology Industry Council, (pp. 4-12; 50-51).

(Continued)

*Primary Examiner* — Blake A Tankersley

(57) ABSTRACT

Embodiments of the invention include systems and methods for determining adhesive strength of a sample label. For example, the present invention relates to a novel approach for examining the resistance to peel force required to remove a pressure sensitive adhesive (PSA) label from its intended substrate. This approach is encompassed by systems and methods which rely on the creation of one or any combination of at least four test strip types traced and cut from a label adhered to its intended substrate. The test strips may be oriented in at least three ways: along the machine direction of the label's face stock, along the cross direction of the label's face stock, and along an angle diagonal to the intersection of the machine and cross directions of the label's face stock, where the angle does not equal 0°, 90°, 180°, 270°, or 360°. The test strips may be peeled in reference to the position along the label and to and from which they extend.

7 Claims, 96 Drawing Sheets

(56) References Cited

OTHER PUBLICATIONS

ASTM D1000-10: Standard Test Methods for Pressure—Sensitive Adhesive—Coated Tapes used for Electrical and Electronic Applications, ASTM International, West Conshohocken, PA (pp. 1-20), Feb. 2010.
ASTM D903: Standard Strength of Adhesive Bonds, ASTM International, West Conshohocken, PA, (pp. 1-3), Oct. 2010.
ASTM D1876-72 (Reapproved 1983): Standard Test Method for Peel Resistance of Adhesive (T-Peel Test), ASTM Committee D-14 on Adhesives, (pp. 139-141).
ISO/IEC FDIS 7810: 2003(E): Identification Cards Physical Characteristics, ISO/IEC, (p. 5).
ISO/IEC 10373-1: Identification Cards—Test Methods—Part 1: General Characteristics, ISO/IEC, (p. 6-9). May 2006.
TLMI Manual of Recommended Standard Test Methods for Pressure Sensitive Labels, 2000 Edition, Tag and Label Manufacturers Institute, Inc., Naperville, IL, (pp. 3-24; 229-230).
Him, U. and Bauer, W., Investigating Paper Curl by Sheet Splitting, EV CEPA Conference "Challenges 06", Bratislava, Slovakia, Nov. 8-9, 2006.
Johnston, J., Pressure Sensitive Adhesive Tapes: A Guide to Their Function, Design, Manufacture, and Use, Pressure Sensitive Tape Council, Northbrook, IL, 2000 (pp. 151-176).
Satas, Donatas (editor), Handbook of Pressure Sensitive Adhesive Technology, Second Edition, Van Nostrand Reinhold, New York, NY, 1989, (pp. 61-96).
Smoak, Gary A., Handbook for Pulp & Paper Technologists, Second Edition, Angus Wilde Publications, Vancouver, BC Canada, 1992 (p. 339).
Beex, L.A.A., et al., An experimental and computational study of laminated paperboard creasing and folding, 46 Int'l J. Solids & Structures 4192-207 (Aug. 25, 2009) [Fig. 6; p. 4196, paragraph 1].
Ghatak, Animangsu, Peeling off an adhesive layer with spatially varying modulus, Physical Rev. E 81, 021603-1 to -6 (Feb. 9, 2010) [Fig. 1].
Laulicht, B., et al., Quick-release medical tape, 109 Proc. Nat'l Acad. Sci. & Tech. 18803-08 (Nov. 13, 2012) [Figs. 1-4].
Lindstrom, S.B., et al., Physical Rev. E 89, 062401-1 to -11 (Jun. 6, 2014) [Figs. 1, 2, and 5].
Sameoto, Dan, et al., Nonangled anisotropic elastomeric dry adhesives with tailorable normal adhesion strength and high directionality, 28 J. Adhesion Sci & Tech. 354-66 (2014) [Figs. 1, 6, 8].
Kroling, H., Anisotrophy of paper and paper based composites and the modeling thereof, 16th Conf. Composite Materials, Seville, Spain, 1-8 (Jun. 22-26, 2014) [p. 2, paragraph 4; p. 4, table 1; p. 5, paragraph 1, 3; p. 6, Fig. 2].

\* cited by examiner

SYSTEMS AND METHODS FOR DETERMINING ADHESIVE STRENGTH

CROSS-REFERENCE TO RELATED APPLICATIONS

This application claims the benefit of prior-filed provisional application No. 62/019,587, filed Jul. 1, 2014, pursuant to 35 U.S.C. § 119(e).

DESCRIPTION OF THE INVENTION

Field of the Invention

The invention relates to systems and methods for determining adhesive strength of a sample label. The systems and methods disclosed herein relate to testing to prevent forgery, counterfeiting, smuggling, identity theft, unauthorized duplication, and immigration fraud concerning the application of adhesive labels bearing security features. Examples of substrates bearing adhesive labels with security features, include but are not limited to, government-issued documents to establish identity, ownership, diplomatic or tax status; documents issued by a religious body or authority; items certified by a religious body; documents issued by academic or scholastic institutions; and the packaging of goods for sale or the goods themselves to establish authenticity, provenance, and compliance with applicable laws and regulations set forth by governmental and regulatory bodies.

Background of the Invention

Thus, it is desirable to have a system and method for determining adhesive strength that more closely mimics the actual conditions of a person manually peeling away a label from a substrate (or a substrate from a label) for nefarious reasons than existing systems and methods.

SUMMARY OF THE INVENTION

Embodiments of the present invention are directed to systems and methods for determining adhesive strength of a sample label that obviate one or more of the limitations and disadvantages of prior systems and methods.

In one embodiment, there is disclosed a method for determining adhesive strength by providing a label having an adhesive layer on a first surface and a second surface opposite the first surface. A substrate is provided having a first surface and a second surface opposite the first surface. The method includes affixing a portion of the adhesive on the first surface of the label to the first surface of the substrate; forming a tab portion on the label from a portion of the label not affixed to the substrate; affixing a tail to the tab portion, the tail being configured receive a pulling force; affixing an adhesive layer to the second surface of the substrate; peeling the label away from the substrate by pulling the tail away from the substrate; and measuring the force required to peel the label from the substrate.

According to another embodiment, there is disclosed a method for determining adhesive strength by providing a label having an adhesive layer on a first surface and a second surface opposite the first surface. A substrate is provided having a first surface and a second surface opposite the first surface. The method includes affixing a portion of the adhesive on the first surface of the label to the first surface of the substrate; forming a tab portion on the substrate from a portion of the substrate not affixed to the label; affixing a tail to the tab portion, the tail being configured receive a pulling force; affixing an adhesive layer to a second surface of the label; peeling the substrate away from the label by pulling the tail away from the label; and measuring the force required to peel the label from the substrate.

According to another embodiment, there is disclosed a system for determining adhesive strength including: a label having an adhesive layer on a first surface and a second surface opposite the first surface; a substrate having a first surface and a second surface opposite the first surface; a portion of the adhesive on the first surface of the label being affixed to the first surface of the substrate; a tab portion formed on the label from a portion of the label not affixed to the substrate; a tail affixed to the tab portion, the tail being configured receive a pulling force; an adhesive layer affixed to the second surface of the substrate; and a sensor for measuring the force required to peel the label from the substrate by peeling the tail away from the substrate.

According to yet another embodiment, there is disclosed a system for determining adhesive strength including: a label having an adhesive layer on a first surface and a second surface opposite the first surface; a substrate having a first surface and a second surface opposite the first surface; a portion of the adhesive on the first surface of the label affixed to the first surface of the substrate; a tab portion formed on the substrate from a portion of the substrate not affixed to the label; a tail affixed to the tab portion, the tail being configured receive a pulling force; an adhesive layer affixed to a second surface of the label; and a sensor for measuring the force required to peel the substrate from the label by peeling the tail away from the label. In various embodiments, the device may include additional features as reflected in the following specification content.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
FIG. 1 provides a cross-section view through the center of the width of a completed test strip created via the Indirect Method which is properly mounted onto a rigid testing plate.

Reference will now be made in detail to the exemplary embodiments of the invention, examples of which are illustrated in the accompanying drawings. Wherever possible, the same reference numbers will be used throughout the drawings to refer to the same or like parts.

According to exemplary embodiments, the invention relates to a novel approach for examining the resistance to peel force required to remove a pressure sensitive adhesive (PSA) label bearing security features from its intended substrate. This approach is encompassed at least by methods which rely on the creation of one or any combination of four test strip types traced and cut from a label adhered to its intended substrate. The test strips may be oriented in three possible ways: along the machine direction of the label's face stock, along the cross direction of the label's face stock, and along an angle diagonal to the intersection of the machine and cross directions of the label's face stock, where the angle does not equal 0°, 90°, 180°, 270°, or 360°. The test strips may be peeled in reference to the position along the label and to and from which they extend. Table 1 below summarizes the information described above:

TABLE 1

A summary of possible peel methods and test strip orientations, peel directions, types, and reversibility characteristics.

| Peel Methods | |
| --- | --- |
| Indirect Peel | Label adhered to substrate. Substrate adhered to testing plate. Label peeled away from substrate. |
| Reverse Direct Peel | Label adhered to substrate. Label face adhered to testing plate. Substrate peeled away from label. |
| Orientations and Associated Peel Directions | |
| Machine Direction | Top to Bottom |
| | Bottom to Top |
| Cross Direction | Left to Right |
| | Right to Left |
| Diagonal Direction | Top Left to Bottom Right |
| | Bottom Right to Top Left |
| | Top Right to Bottom Left |
| | Bottom Left to Top Right |

TABLE 1-continued

A summary of possible peel methods and test strip orientations, peel directions, types, and reversibility characteristics.

| Test Strip Types and Ability to Reverse Peel Direction | |
| --- | --- |
| Edge-to-Edge | Yes |
| Edge-to-Interior | No; strip becomes "interior-to-edge" |
| Interior-to-Edge | No; strip becomes "edge-to-interior" |
| Interior-to-Interior | Yes |

The purpose of developing these methods was to enable an analyst to mimic the manual removal of a PSA label bearing security features by a person involved in activities such as, but not limited to, forgery, counterfeiting, smuggling, identity theft, unauthorized duplication, and immigration fraud which may be performed by or in conjunction with persons engaged in terrorist activities. An analyst may choose to use one method exclusively or choose to use multiple methods to extract the greatest amount of resistance to peel data for a PSA label with security features affixed to its intended substrate.

Definition of a PSA Label with Security Features

A PSA label with security features is a label which is characterized by the presence of at least one element specially designed for counterfeit deterrence, tamper resistance, evidence of tampering, the establishment of provenance and authentication, or any combination of these thereof. These elements may be incorporated into the label before, during, or after printing, and there is no restriction to the number of elements which may be present. The presence of a security element within the label's area and throughout its composition may range from parts of the label to the entire area of the label. Some elements may be incorporated in the manufacture of the label's face stock, the label's pressure sensitive adhesive, and/or the printing and finishing processes of the final product.

Examples of these elements may include, but are not limited to, holograms and other types of secure appliqués, UV fluorescent fibers, security threads, security ribbons, planchettes, taggants, chemical markers, biological markers, chemical indicators, microelectronics, magnetic strips, complex imaging, calculated or changeable content, security printing inks, and security printing techniques, the die-cutting of voids into an area within the label, and any additional stamping or post-production processing performed by a human or a machine including but not limited to acts to input uniquely identifying data onto the label, acts of authentication, and acts to indicate the issuance of authorization related to the function and nature of the label in reference to its substrate.

Definition of a Substrate and the Relationship Between Label and Substrate

Examples of substrates bearing PSA labels with security features, include but are not limited to, government-issued documents to establish identity, ownership, diplomatic or tax status; documents issued by a religious body or authority; items certified by a religious body; documents issued by academic or scholastic institutions; and the packaging of goods for sale or the goods themselves to establish authenticity, provenance, and compliance with applicable laws and regulations set forth by governmental and regulatory bodies. Some examples of substrates which are directly issued to individuals, which include but are not limited to, birth certificates, baptismal certificates, and marriage licenses, are recognized as "breeder" or secondary documents. Secondary documents are those documents which are accepted to complete applications for primary forms of identification such as, but not limited to, driver's licenses and passports which are sought by, for example, a forgery perpetrator, looking to conceal information on or alter a pre-existing document. It is imperative then that a label used to authenticate a substrate be adhered strongly enough to the substrate to show signs of tampering to both the label and the substrate if removal is attempted.

The substrates onto which PSA labels bearing security features are affixed include, but are not limited to, bound materials, single sheets, and layers of paper, cloth, cardboard, plastics, and other packaging materials, which can be composed of naturally occurring organic and inorganic materials or synthetically produced materials, or any combination thereof.

The substrates onto which the PSA labels bearing security features are affixed may also be treated by chemical and physical means including, but not limited to, pigmentation/dyeing, coating, varnishing, and lamination. Security features may also be incorporated throughout the entire substrate or on those areas of the substrate which have contact with the label. Any security features present on the substrate may possibly work in tandem with the security features of the label. Other security features may extend past the perimeter of the PSA label and onto the substrate to which it is affixed.

Additionally, the area of the substrate onto which the PSA label bearing security features is affixed may be homogenous in composition and treatment or heterogeneous in composition and treatment.

Brief Overview of Current Testing Methods

A number of methods to examine the resistance to peel strength of pressure sensitive adhesives currently exist in the literature. Some methods examine pressure sensitive adhesives by affixing the label directly to a rigid testing plate, such as steel (Tag and Label Manufacturers Institute, Inc. (TLMI), "180° Peel Adhesion Face Stock from Substrate") or glass (FINAT Test Methods No. 1, No. 2, and No. 3). While these tests do provide a means of comparing adhesive strength, the labels may not necessarily be affixed to metal or glass substrates in actual use. Also, the TLMI method calls for the use of a 2 kg roller to ensure proper adhesion of the label to the steel substrate. PSA labels with security features more likely would be applied by hand, resulting in much less force on the label.

The "T-Peel" test described within ASTM D1876 involves affixing the label to its intended substrate. However, in this test, substrate and label are pulled away from one another simultaneously. A PSA label with security features is likely to be removed for unlawful, unauthorized, and/or improper reasons. An individual engaging in this activity will employ the utmost care to successfully liberate the PSA label or a portion of interest from the PSA label. This portion of interest may be along the perimeter or it may be well within the interior of the label. The "T-Peel" test is likely to cause delamination of the label, the substrate, or both. Delamination, a common failure mechanism of composite materials, is the separation of a material into layers. Thus, it is unwise and not effective to simulate the attempted removal of the label for unlawful purposes using the "T-Peel" test method.

ASTM D903 describes a more gentle process of removal. However, this test is designed to run at 180° and at a speed of 12 inches per minute, which is very unlikely to be achieved by a person manually peeling away a label from a substrate for nefarious reasons. Also, in the commercially available methods described, a minimum strip length is prescribed in a range of 5-6 inches, and the portion of the strip wherein the substrate and label are not bonded is generally 1 inch. In some cases an actual label may not be able to yield a strip between 5-6 inches long. In the actual practice of removing a label from a substrate, unless the adhesive is of low tackiness and strength, it is unusual during the first attempts of manual removal to peel away one inch of the label from the substrate or the substrate from the label by hand. A fraction of an inch, usually in the range of ¼" to ½", is more realistic. The two novel methods described in this paper are performed at 90° and at a slower speed of removal (10 inches per minute), which more closely mimics the conditions of manual peeling that would be used by an individual involved in activities such as, but not limited to, forgery, unauthorized duplication, counterfeiting, smuggling, and immigration fraud, which theoretically could be conducted parallel to, in conjunction with, and possibly in support of terrorist acts against a nation state.

BRIEF DESCRIPTION OF METHODS

The two methods to be discussed call for the PSA label with security printing features to be adhered directly to the intended substrate. After the label is affixed directly to the intended substrate, the resistance to peel force to remove the label may be measured by two separate methods which are intended to simulate manual attempts at removal—the "Indirect Method" and the "Reverse-Direct Method".

The "Indirect Method" involves the indirect adhesion of the label to the rigid testing plate. A sample test strip traced from label 100 is peeled away from the obverse surface of substrate 102, onto which it is affixed by a release and adhesion tester. The reverse or back side of substrate 102 is affixed to rigid testing plate 104 with suitably strong double-sided tape piece 106 (FIG. 1).

Figure 2:
FIG. 2 provides a cross-section view through the center of the width of a completed test strip created via the Reverse-Direct Method which is properly mounted onto a rigid testing plate.

Alternatively, a label can be separated from its substrate in another manner. An attempt can be made to liberate a label from its substrate by peeling the substrate away from the label. Instead of mounting the substrate 102 to the rigid testing plate 104 with double-sided tape 106 or other adhesive, the non-adhesive side of the label 100 can instead be mounted directly to the rigid testing plate 104 with the double-sided tape 106. This is referred to as the "Reverse-Direct Method" (FIG. 2).

Regardless of whether the Indirect or Reverse-Direct method is utilized, the rigid plate is then mounted onto a release and adhesion tester. The release and adhesion tester with a force transducer of 25 IbF is programmed to run at 90 degrees and 10 inches per minute (254 millimeters per minute) or less in order to measure the resultant force required to separate the two during a simulation of a willful attempt at removing the label by hand with the goal of creating minimal-to-no damage to the label and/or the substrate.

Selection of a Test Strip Area
Background on Properties of Printed/Sheeted Materials Paper, textiles, and other sheeted materials are anisotropic. Anisotropy is the phenomenon which exists when the magnitude of a measurable physical property is directionally dependent. In paper science, the differences in physical measurements along the machine and cross directions of a sheet are well documented.

Figure 3:
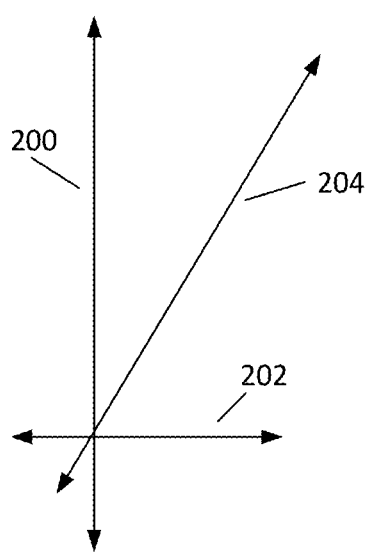
FIG. 3 depicts the relationship between the machine, cross, and diagonal directions of a sheeted material.

The machine direction 200 is the direction from which textiles and other sheeted materials, including but not limited to paper, travel through the machine of manufacture. The cross direction 202 is perpendicular to the machine direction 200. A label can be peeled away from its substrate from either along its machine 200 or cross direction 202, or an attempt may be made to peel a label away at an angle or a diagonal direction 204 relative to the machine 200 and cross 202 directions as shown in FIG. 3.

Construction of Labels

A PSA label is comprised of three main components:

1.) Label stock—that sheeted material which may possess security features as part of the manufacturing process, including but not limited to any of the following: UV fluorescing fibers, planchettes, chemical stain protection, etc., and onto which additional security features may be applied;

2.) Adhesive—a pressure sensitive adhesive, which may include additives, such as taggants for security purposes to establish provenance/authenticity, and may work in tandem with other security features on the label stock and/or the substrate; and 3.) Backing sheet—usually silicone-coated or coated with some other material to preserve the tackiness of the adhesive before the label is affixed to the desired substrate.

Printing of the PSA label is performed after the label stock, adhesive, and backing sheet have been combined to form a "married" stock or a coated roll. The side of the coated roll with the label stock is then printed on by conventional, secure, or any combination thereof of printing modalities before being die-cut into individual labels which may then be easily removed from the backing sheet. However, there may exist PSA labels with security features which are die-cut prior to the application of any printing process. The thickness of the label is determined by the thickness of the printed label stock and the adhesive after all manufacturing stages, printing processes, and any other treatments have been completed. Label thickness may vary along different areas of the label depending upon the manufacturing and printing processes used and the sequencing of these events.

Label Shape

The shape of a label may be described by its outermost perimeter created by the die-cutting process. The number of possible shapes and dimensions by which a label may be constructed is infinite. Label shape may be described broadly within three main categories:

1) polygonal,
that is, a planar figure which is bound by a finite chain of straight line segments closing in a loop to form a closed chain or circuit, which may be further subdivided into the following:
Regular polygons (all sides and all angles are equal; always convex), or Irregular polygons (all sides and all angles are not equal; may be concave or convex);
2) elliptical/circular,
whereby the area (A) can be calculated as equal to the product of pi, foci 1, and foci 2. $A = \pi \cdot f_1 \cdot f_2$; or,
3) a shape which is not defined by 1) and 2) above,
which may be broadly described as a planar figure bound by a finite chain or straight line segments and/or curved line segments closing in a loop to form a closed chain or circuit.

Tracing a Test Strip
Strip Dimensions

The dimensions of the test strip are dependent upon the size of the PSA label from which it will be derived and the limitations on measurement of the release and adhesion tester used to perform the peel. Dimensions may also be limited by the design of the release and adhesion tester and what maximum/minimum sample size the device is designed to physically accommodate.

Length

The length of the test strip should equal the length along the label that the analyst wishes to investigate the resistance to peel strength. A template should be used to maintain identical test strip length for each replicate sample.

Width

The width of the test strip should remain constant across the length of the label that the analyst wishes to investigate. A template should be used to maintain identical test strip width for each replicate sample. The recommended width of the test strip is one inch.

Cases where Length and/or Width are not Constant Across a Traced Test Strip

Depending upon the shape of the label's perimeter and also upon the location within the label that the analyst wishes to investigate, the length and/or width of the test strip may not remain constant across a traced test strip. If the analyst is unable to design a template which will exactly accommodate any of these dimensional irregularities, the analyst shall choose "landmarks" along the design of the label with which to align a template to ensure that replicates traced from other labels will produce identical samples. Two possible embodiments are shown in FIG. 4A-C and FIG. 5A-C.

Figure 4A:
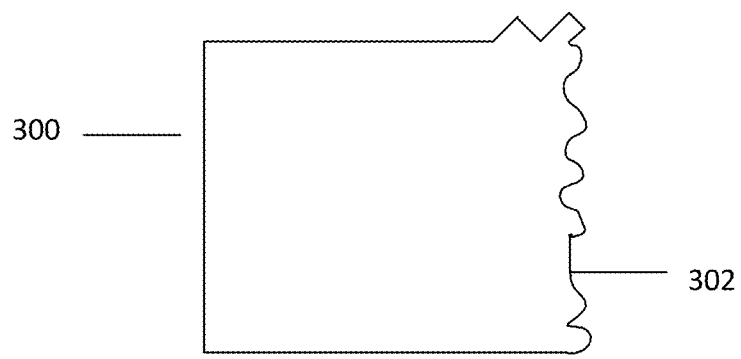
FIG. 4A shows an example of a pressure sensitive adhesive (PSA) label that is neither polygonal nor elliptical in shape.
Figure 4B:
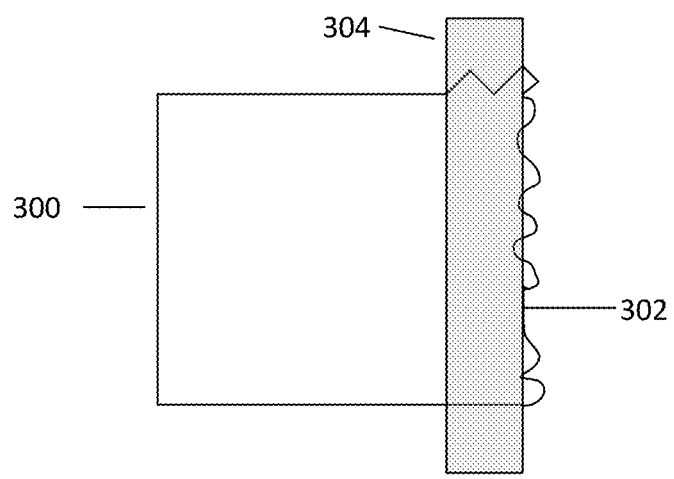
FIG. 4B depicts the alignment of a template along a landmark feature of the label chosen along the perimeter of a PSA label that is neither polygonal nor elliptical in shape.
Figure 4C:
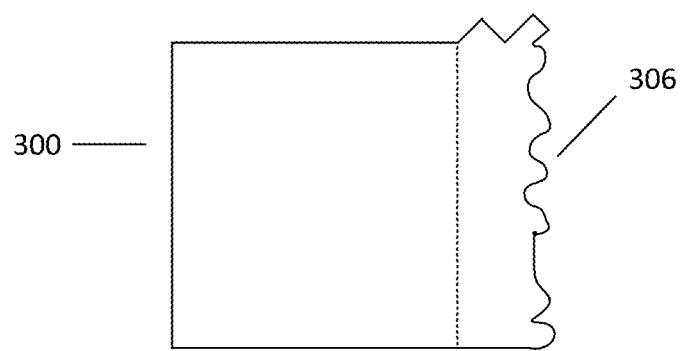
FIG. 4C provides an example of a test strip traced in the machine direction onto a label with the template aligned to a landmark feature along the perimeter of a PSA label that is neither polygonal nor elliptical in shape.

FIG. 4A provides an example of a label 300 which is neither polygonal nor elliptical, from which the analyst wishes to derive a test strip along machine direction 200 from the far right edge of label 300. Along the far right edge of label 300, a landmark, indicated by reference number 302, has been identified against which the analyst will align template 304, as shown in FIG. 4B, to trace a sample test strip. The sample test strip, traced along machine direction 200 and indicated by reference number 306, serves as one possible example of a test strip traced in the machine direction onto label 300 as shown in FIG. 4C.

Figure 5A:
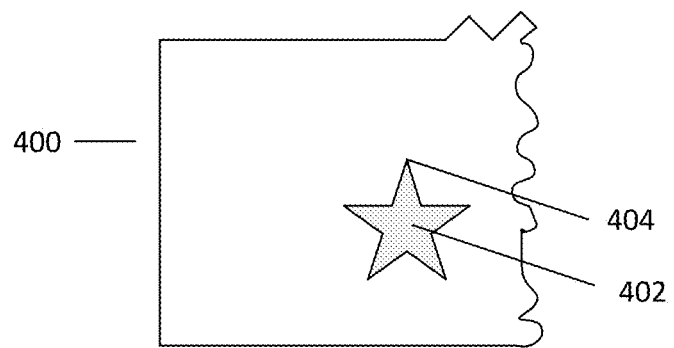
FIG. 5A shows an example of a pressure sensitive adhesive (PSA) label that is neither polygonal nor elliptical in shape on which a landmark is identified by the analyst from a printed feature within the interior of the label.
Figure 5B:
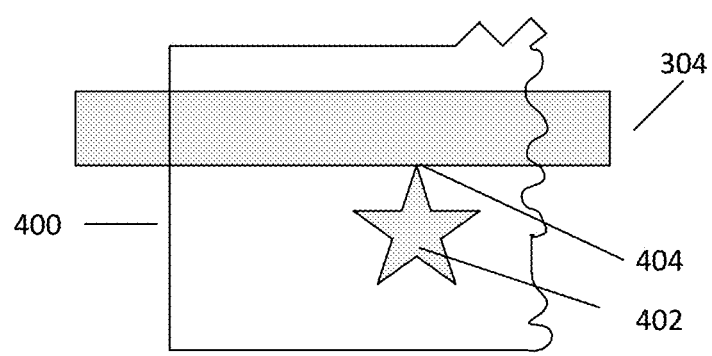
FIG. 5B depicts the alignment of a template along a landmark feature identified within the interior of a PSA label depicted in FIG. 5A.
Figure 5C:
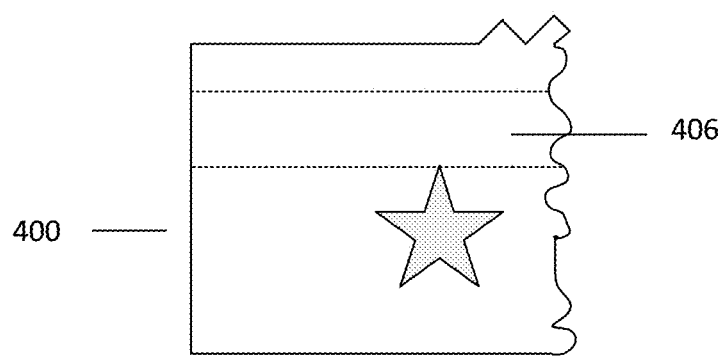
FIG. 5C depicts an example of a test strip traced in the cross direction using the template in FIG. 5B aligned with the landmark feature identified within the interior of a PSA label depicted in FIG. 5A.

Label 400 shown in FIG. 5A is neither polygonal nor elliptical and features prominent graphical motif 402. The analyst wishes to derive a test strip along cross direction 202 from the upper portion of label 400. In FIG. 5A-B landmark 404, the uppermost point of graphical motif 402, has been identified on label 400. The analyst will proceed to align template 304 against landmark 404, as shown in FIG. 5B, in order to trace a sample test strip. The resultant test strip 406 traced along cross direction 202 is depicted in FIG. 5C.

Types of Test Strips

Test strips may be divided into four categories:

"Edge-to-Edge"—a test strip created such that peeling originates and terminates along different, non-overlapping segments of the label's perimeter. Peel direction may be reversed in an alternate set of strips;

"Edge-to-Interior"—a test strip created such that the peeling originates along one segment of the perimeter and terminates at a position within the interior area of the label;

"Interior-to-Edge"—a test strip created such that the peeling originates from a position within the interior area of the label and terminates along one segment of the perimeter; and "Interior-to-Interior"—a test strip created such that the peeling that originates and terminates from two different, non-overlapping positions within the interior area of the label. Peel direction may be reversed in an alternate set of strips.

Figure 6A:
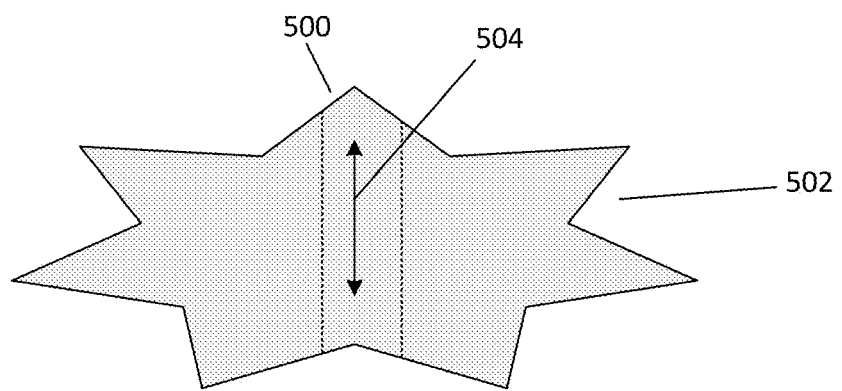
FIG. 6A provides an example of an edge-to-edge test strip traced in the machine direction.
Figure 6B:
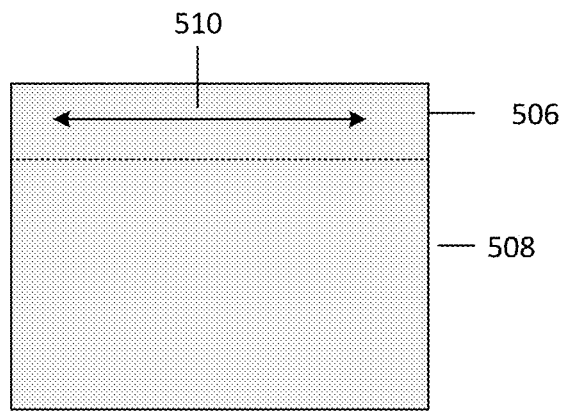
FIG. 6B provides an example of an edge-to-edge test strip traced in the cross direction.
Figure 6C:
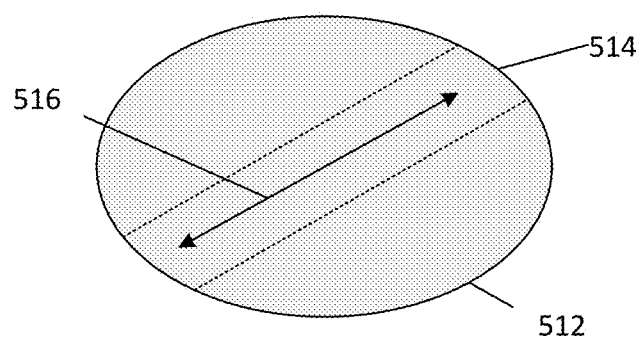
FIG. 6C provides an example of an edge-to-edge test strip traced in the diagonal direction.

Some possible embodiments of edge-to-edge strips are shown in FIG. 6A-C.

Reference number 500 in FIG. 6A corresponds to one possible embodiment of an edge-to-edge strip traced along the machine direction of a duplicate of polygonal shaped label 502. Double arrow 504 indicates the bi-directionality of the peel (either from top to bottom or bottom to top).

Reference number 506 in FIG. 6B corresponds to a possible embodiment of an edge-to-edge strip traced along cross direction 202 of a duplicate of polygonal shaped label 508. Double arrow 510 indicates the bi-directionality of the peel (either from left to right or right to left).

Reference number 514 in FIG. 6C corresponds to a possible embodiment of an edge-to-edge strip traced along diagonal 204 of the intersection of machine 200 and cross 202 directions of a duplicate of elliptical shaped label 512. Double arrow 516 indicates the bi-directionality of the peel (either from upper right to bottom left or bottom left to upper right).

Figure 7A:
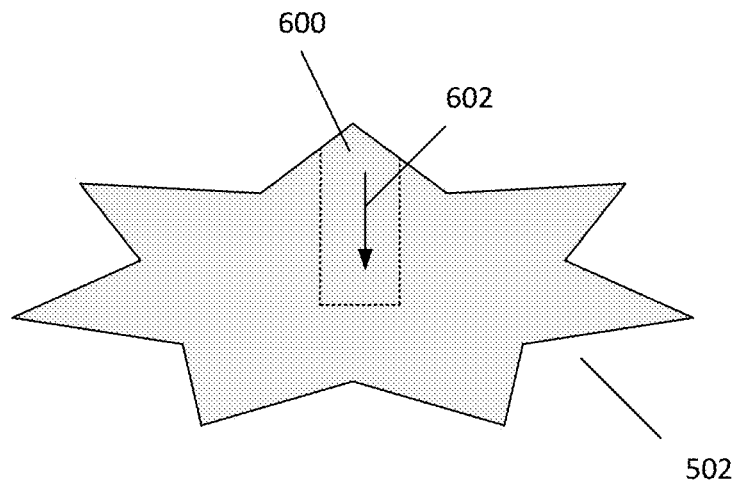
FIG. 7A provides an example of an edge-to-interior test strip traced in the machine direction.
Figure 7B:
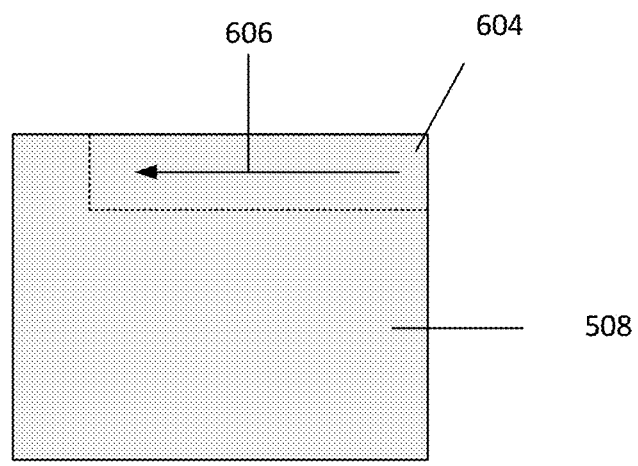
FIG. 7B provides an example of an edge-to-interior test strip traced in the cross direction.
Figure 7C:
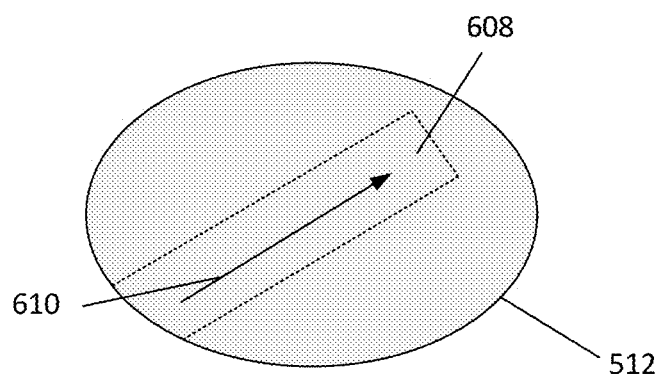
FIG. 7C provides an example of an edge-to-interior test strip traced in the diagonal direction.

Some possible embodiments of edge-to-interior strips are given in FIG. 7A-C, with the arrow on each figure indicating the direction of the peel along each orientation.

One possible embodiment of an edge-to-interior strip, indicated by reference number 600, is traced along the machine direction 200 of a duplicate of polygonal shaped label 502, as depicted in FIG. 7A. Single arrow 602 indicates the peel direction is unidirectional, from top to bottom.

One possible embodiment of an edge-to-interior strip, indicated by reference number 604, is traced along cross direction 202 of a duplicate of polygonal shaped label 508, as shown in FIG. 7B. Single arrow 606 indicates the peel direction is unidirectional, from left to right.

Reference number 608 in FIG. 7C corresponds to a possible embodiment of an edge-to-interior strip which is shown traced along diagonal 204 of the intersection of machine 200 and cross 202 directions on a duplicate of elliptical shaped label 512. Single arrow 610 indicates the peel direction is unidirectional, from bottom left to top right.

Figure 8A:
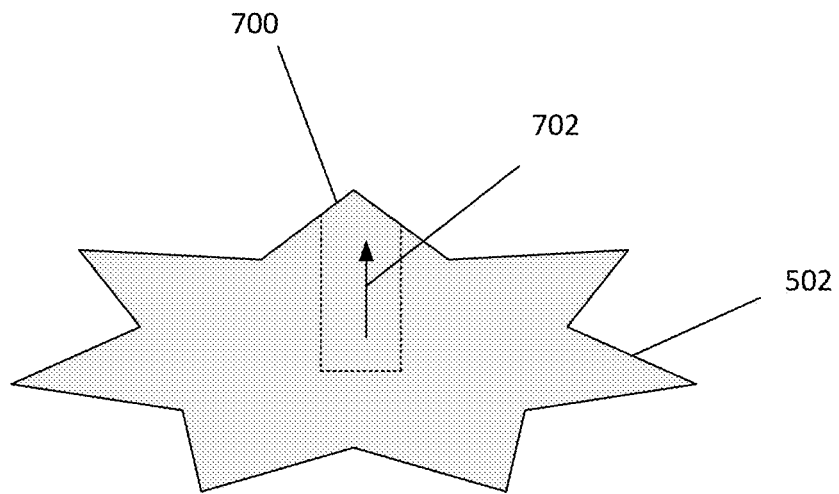
FIG. 8A provides an example of an interior-to-edge test strip traced in the machine direction.
Figure 8B:
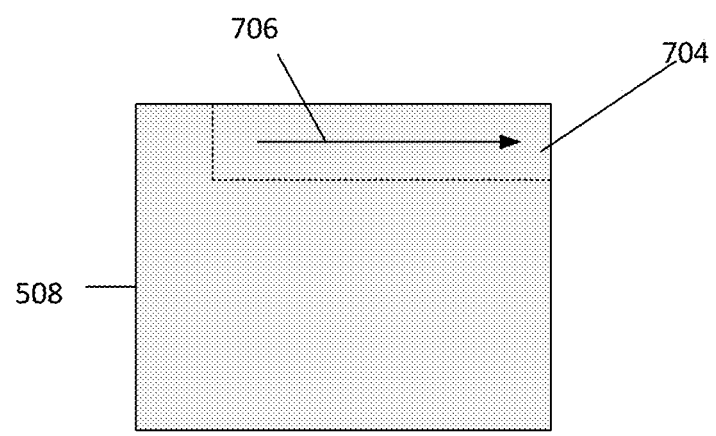
FIG. 8B provides an example of an interior-to-edge test strip traced in the cross direction.
Figure 8C:
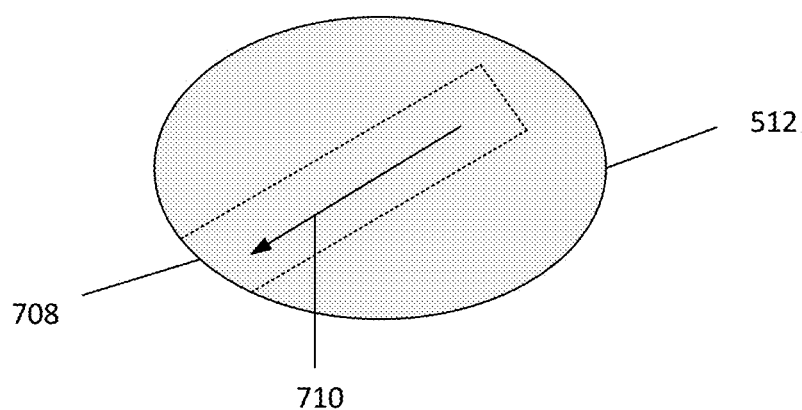
FIG. 8C provides an example of an interior-to-edge test strip traced in the diagonal direction.

Some possible embodiments of interior-to-edge strips are shown in FIG. 8A-C, with the arrow on each figure indicating the direction of the peel along each orientation.

In FIG. 8A one possible embodiment of an interior-to-edge strip, indicated by reference number 700, is traced along machine direction 200 of a duplicate of polygonal shaped label 502. Single arrow 702 indicates direction of peel is unidirectional (bottom to top).

In FIG. 8B one possible embodiment of an interior-to-edge strip, indicated by reference number 704, is traced along cross direction 202 of a duplicate of polygonal shaped label 508. Single arrow 706 indicates the direction of peel is unidirectional (left to right).

In FIG. 8C one possible embodiment of an interior-to-edge strip, indicated by reference number 708, is traced along diagonal 204 of the intersection of machine 200 and cross 202 directions on a duplicate of elliptical shaped label 512. Single arrow 710 indicates the direction of peel is unidirectional (top right to bottom left).

Figure 9A:
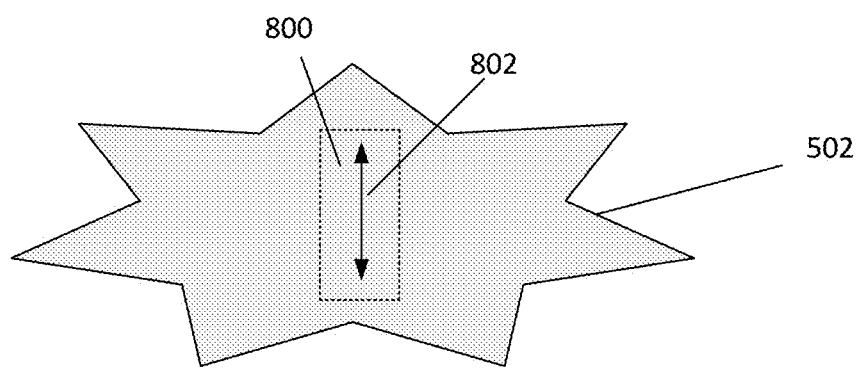
FIG. 9A provides an example of an interior-to-interior test strip traced in the machine direction.
Figure 9B:
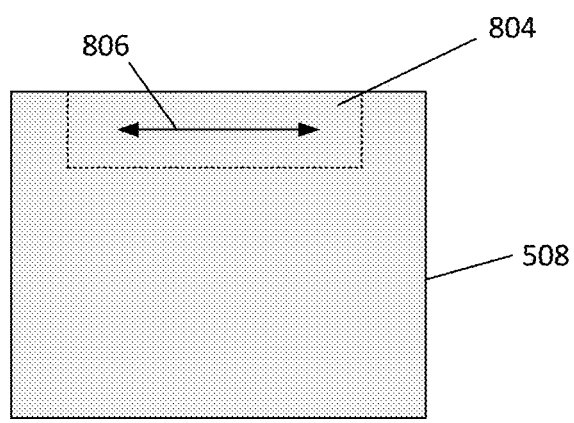
FIG. 9B provides an example of an interior-to-interior test strip traced in the cross direction.
Figure 9C:
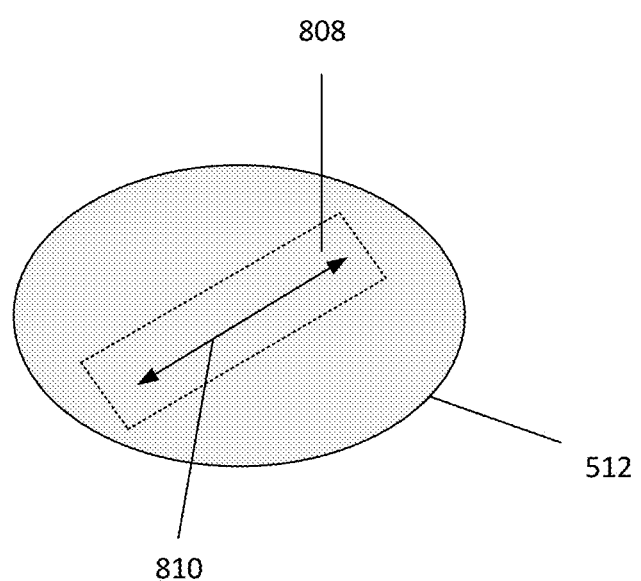
FIG. 9C provides an example of an interior-to-interior test strip traced in the diagonal direction.

Some possible embodiments of interior-to-interior strips are shown in FIG. 9A-C. Double arrows indicate possible directions of peel for each strip shown.

In FIG. 9A one possible embodiment of an interior-to-interior strip corresponding to reference number 800 is shown traced along machine direction 200 of a duplicate of polygonal shaped label 502. Double arrow 802 indicates peel may be performed from top to bottom or bottom to top.

In FIG. 9B one possible embodiment of an interior-to-interior strip 804 is shown traced along the cross direction 202 of a polygonal shaped label 508. Double arrow 806 indicates peel may be performed from left to right or right to left.

In FIG. 9C one possible embodiment of an interior-to-interior strip 808 is shown traced along a diagonal 204 of the intersection of the machine 200 and cross 202 directions on an elliptical shaped label 512. Double arrow 810 indicates peel may be performed from upper right to bottom left or from bottom left to upper right.

Rationale for Choosing a Test Strip Type

Through the combination of the number of areas of interest within the label, the test strip type, the orientation of the strip with regard to the label face stock (machine, cross, diagonal), and the direction from which the peel commences, the analyst is able to design an array of experiments.

Scenario 1: Examining Resistance to Peel Strength Throughout the Entire Area of a Label It is necessary for the analyst to gather data throughout the entire area of the label if an intact label in its entirety is of interest for potential forgery, unauthorized duplication, or alteration. If the entire label area is of interest, the creation of edge-to-edge strips along different orientations (machine, cross, and diagonal) of the label are applicable. In the case that a whole number of test strips cannot be created along an orientation (e.g., where the number of equally sized test strips leaves a fraction of one test strip's area exposed), the analyst may choose to toggle the non-conforming space within that orientation in order to obtain more complete data. In this case, strips with areas which do not directly overlap should not be averaged with one another.

One possible embodiment of Scenario 1 may be realized with test strips traced along the machine direction 200 of a label. Reference numbers 1001, 1003, 1005, 1007, and 1009 featured in FIG. 10A-E, respectively, correspond to duplicates of the same polygonal shaped label.

Figure 10A:
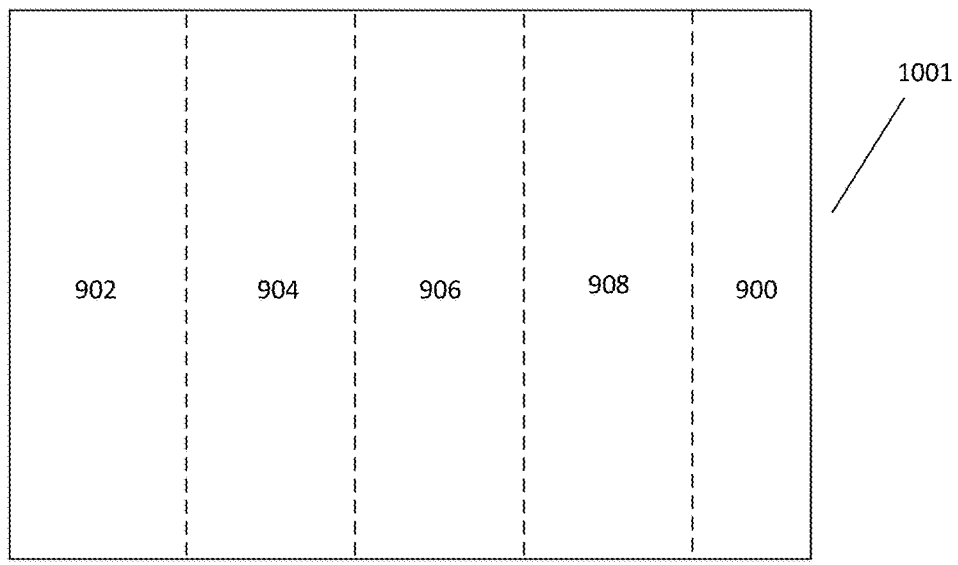
FIG. 10A shows an example of a polygonal label with four test strips of equal width traced in the machine direction, beginning from the far left edge of the label, and featuring an area of non-conformance along the far right edge of the label, the width of which is less than the width of any of the conforming tests strips.

In FIG. 10A four strips, each equal to the width of the template and corresponding to reference numbers 902, 904, 906, and 908, are traced along the machine direction 200 beginning from the left edge of label 1001. An area of non-conformity indicated by reference number 900 remains along the right edge of label 1001.

Figure 10B:
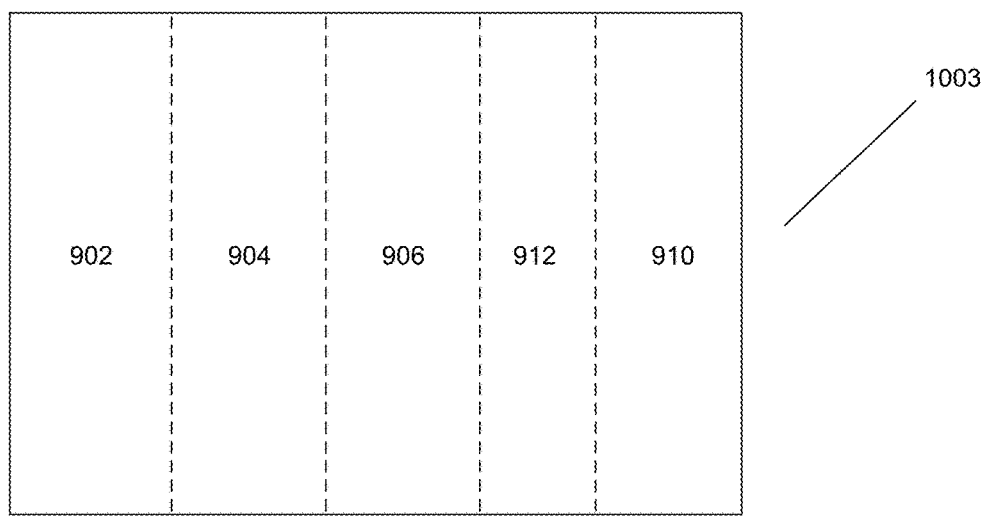
FIG. 10B shows an example of a polygonal label with four test strips of equal width traced in the machine direction and an area of non-conformance which has a width that is less than the width of any of the test strips in which the placement of the area of non-conformance has been shifted to the left of its original position in FIG. 10A by one multiple of the width of the conforming test strips.

In FIG. 10B the test strips corresponding to reference numbers 902, 904, and 906 occupy the same area and respective positions along label 1003 as in label 1001 presented previously in FIG. 10A. An area of non-conformity is designated by reference number 912 on label 1003. The position of area of non-conformity 912 in label 1003 is displaced to the left by one multiple of the width of the template used to trace the test strips, relative to the position of the original area on non-conformity 900 within label 1001 of FIG. 10A. Traced onto label 1003 is test strip 910, which is not in common to labels 1001 and 1003. Test strip 910 is traced along the right edge of label 1003 and includes the entire area and position occupied by area of non-conformity 900 of label 1001 and a portion of the area and position occupied by strip 908 as traced onto label 1001.

Figure 10C:
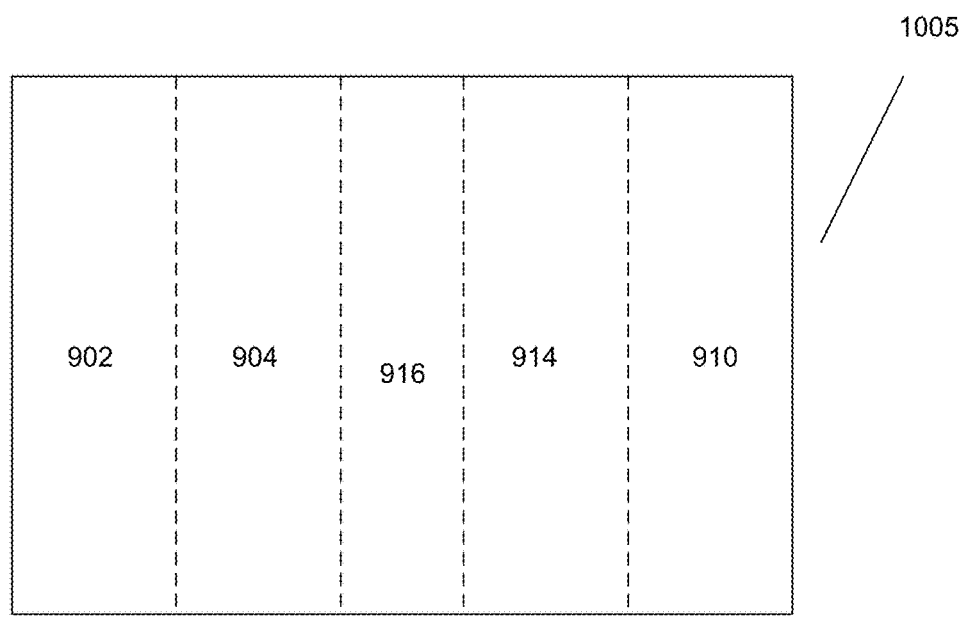
FIG. 10C shows an example of a polygonal label with four test strips of equal width traced in the machine direction and an area of non-conformance, which has a width that is less than the width of any of the test strips, such that the placement of the area of non-conformance has been shifted to the left of its original position in FIG. 10A by two multiples of the width of the conforming test strips.

In FIG. 10C strips corresponding to reference numbers 902 and 904 occupy the same areas and respective positions on label 1005 as along labels 1001 and 1003 as presented previously in FIG. 10A-B. No test strips other than those designated by reference numbers 902 and 904 are in common between labels 1001, 1003, and 1005. Strips corresponding to reference number 910 occupy the same areas and respective positions on labels 1003 and 1005. No other test strips other than those designated by reference numbers 902, 904, and 910 are in common between labels 1003 and 1005. An area of non-conformity along label 1005 is designated by reference number 916. The position of area of non-conformity 916 within label 1005 is displaced to the left by two multiples of the width of the template used to trace the test strips, relative to the position of the original area of non-conformity 900 of label 1001.

Traced onto label 1005 is test strip 914, which is not in common either to labels 1001 or 1003. Test strip 914 on label 1005 is traced along the right edge of the area of non-conformity 916 and the left edge of strip 910 and includes the entire area and position occupied by area of non-conformity 912 of label 1003 and a portion of the area and position occupied by strip 906 as traced onto labels 1001 and 1003. Test strip 914 also includes a portion of the area occupied by strip 908 as traced onto label 1001 in FIG. 10A.

Figure 10D:
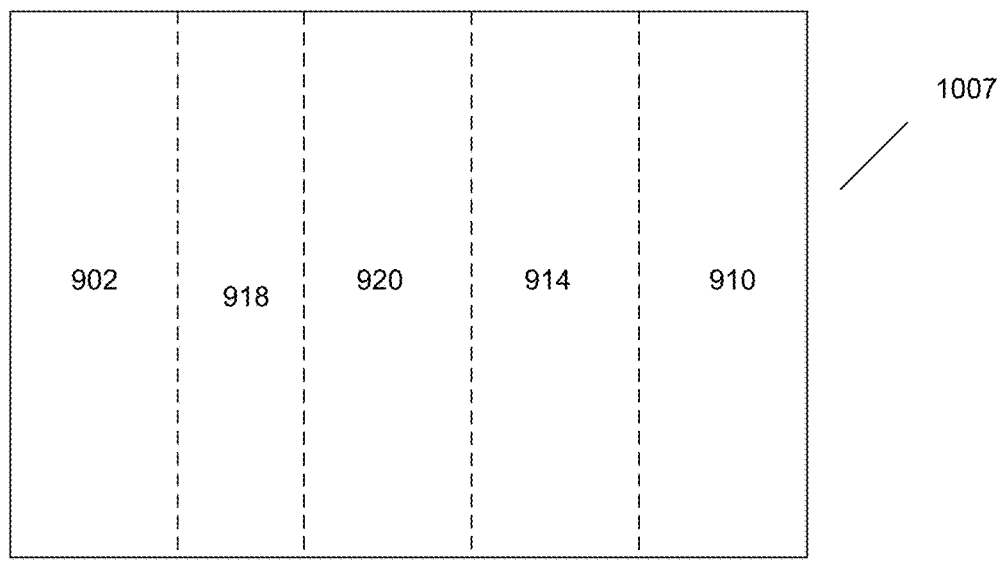
FIG. 10D shows an example of a polygonal label with four test strips of equal width traced in the machine direction and an area of non-conformance, which has a width that is less than the width of any of the test strips, such that the placement of the area of non-conformance has been shifted to the right of its original position in FIG. 10A by three multiples of the width of the conforming test strips.

In FIG. 10D the strip corresponding to reference number 902 occupies the same area and respective position on label 1007 as along labels 1001, 1003 and 1005 presented previously in FIG. 10A-C. No test strip other than that designated by reference number 902 is in common between labels 1001, 1003, 1005, and 1007. Also in FIG. 10D, the strip corresponding to reference number 910 occupies the same area and respective position on label 1007 as along labels 1003 and 1005. No test strips other than 910 and 902 are in common between labels 1003, 1005, and 1007. Between labels 1005 and 1007, no test strips other than 902, 914, and 910 are in common.

An area of non-conformity along label 1007 is designated by reference number 918. The position of area of non-conformity 918 within label 1007 is displaced to the left by three multiples of the width of the template used to trace the test strips, relative to the position of the original area of non-conformity 900 of label 1001. Traced onto label 1007 is test strip 920, which is not in common with labels 1001, 1003, or 1005. Test strip 920 is traced along the right edge of area of non-conformity 918 and the left edge of strip 914 and includes the entire area and position occupied by area of non-conformity 916 of label 1005 and a portion of the area and position occupied by strip 904 as traced onto labels 1001, 1003, and 1005. Test strip 920 also includes a portion of the area and position occupied by strip 906 in labels 1001 and 1003.

Figure 10E:
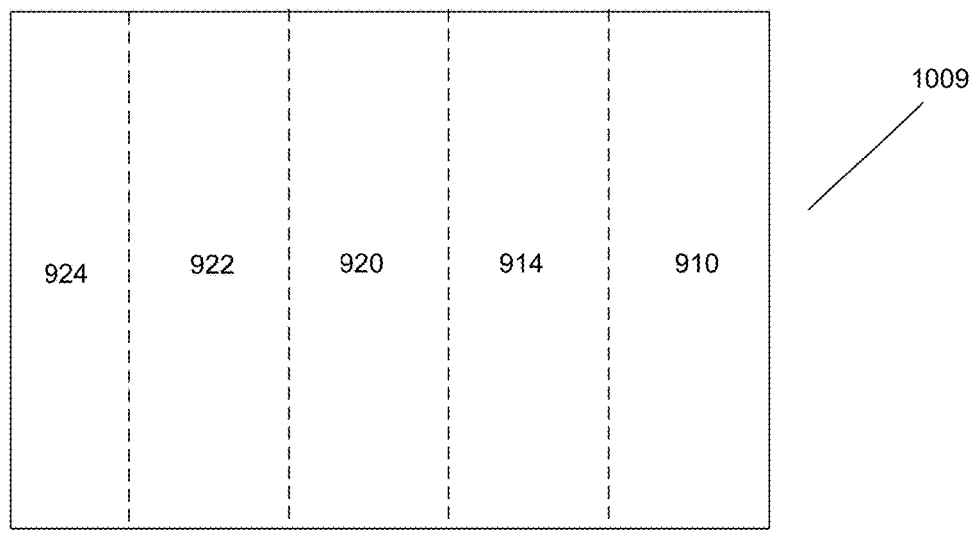
FIG. 10E shows an example of a polygonal label with four test strips of equal width traced in the machine direction and an area of non-conformance, which has a width that is less than the width of any of the test strips, such that the placement of the area of non-conformance has been shifted to the right of its original position in FIG. 10A by four multiples of the width of the conforming test strips.

In FIG. 10E the strip corresponding to reference number 910 occupies the same area and respective position on label 1009 as along labels 1003, 1005, and 1007 presented previously in FIG. 10B-E. No test strip other than that designated by reference number 910 is in common between labels 1003, 1005, 1007, and 1009. Also in FIG. 10E, the strip corresponding to reference number 914 occupies the same area and respective position on label 1009 as along labels 1005 and 1007. No test strips other than 910 and 914 are in common between labels 1005, 1007, and 1009. Additionally, the strip corresponding to reference number 920 in FIG. 10E occupies the same area and respective position on label 1009 as along label 1007. Only strips 910, 914, and 920 are in common between labels 1007 and 1009.

An area of non-conformity along label 1009 is designated by reference number 924. The position of the area of non-conformity 924 within label 1009 is displaced to the left by four multiples of the width of the template used to trace the test strips, relative to the position of the original area of non-conformity 900 of label 1001. Area of non-conformity 924 is located along the left edge of label 1009. Traced onto label 1009 is test strip 922, which is not in common with labels 1001, 1003, 1005, or 1007. Test strip 922 is traced along the right edge of the area of non-conformity 924, and the left edge of strip 920 and includes the entire area and position occupied by area of non-conformity 918 of label 1007 and a portion of the area and position occupied by strip 902 as traced onto labels 1001, 1003, 1005, and 1007. Test strip 922 also includes a portion of the area and position occupied by strip 904 as traced onto labels 1001, 1003, and 1005.

Thus the following relationships may be derived:

Replicates of strip 902 traced onto labels 1001, 1003, 1005, and 1007 as presented in FIG. 10A-D may be averaged together as each occupies the same position along these duplicate polygonal labels.

Replicates of strip 904 traced onto labels 1001, 1003, and 1005 as presented in FIG. 10A-C may be averaged together as each occupies the same position along these duplicate polygonal labels.

Replicates of strip 906 traced onto labels 1001 and 1003 as presented in FIG. 10A-B may be averaged together as each occupies the same position along these duplicate polygonal labels.

Replicates of strip 910 traced onto labels 1003, 1005, 1007, and 1009 as presented in FIG. 10B-E may be averaged together as each occupies the same position along these duplicate polygonal labels.

Replicates of strip 914 traced onto labels 1005, 1007, and 1009 as presented in FIG. 10C-E may be averaged together as each occupies the same position along these duplicate polygonal labels.

Replicates of strip 920 traced onto labels 1007 and 1009 as presented in FIG. 10D-E may be averaged together as each occupies the same position along these duplicate polygonal labels.

Replicates of strip 908 traced onto label 1001 as presented in FIG. 10A cannot be averaged with replicates of strips corresponding to any of the other reference numbers previously provided in FIG. 10A-E.

Replicates of strip 922 traced onto label 1009 as presented in FIG. 10E cannot be averaged with replicates of strips corresponding to any of the other reference numbers previously provided in FIG. 10A-E.

The chart below offers a matrix which summarizes the relationships outlined above:

| LABEL | STRIPS | | | | | | | |
|---|---|---|---|---|---|---|---|---|
| | 902 | 904 | 906 | 908 | 910 | 914 | 920 | 922 |
| 1001 | X | X | X | X | | | | |
| 1003 | X | X | X | | X | | | |
| 1005 | X | X | | | X | X | | |
| 1007 | X | | | | X | X | X | |
| 1009 | | | | | X | X | X | X |

To increase the number of replicates available to study a particular position along the cross direction of the label in the embodiment of Scenario 1 demonstrated throughout FIG. 10A-E, for example, the position occupied by test strip 922, which is created in label 1009 of FIG. 10E as a result of toggling the area of non-conformity several times previously, it is incumbent on the analyst to reproduce the configuration of test strips as traced onto label 1009 onto enough duplicate labels to satisfy the statistical confidence desired by the analyst.

Another possible embodiment of the principle described in Scenario 1 may be realized with tests strips traced along the cross direction 202 of a label. Reference numbers 1101, 1103, 1105, and 1107 featured in FIG. 11A-D, respectively, correspond to duplicates of the same polygonal shaped label.

Figure 11A:
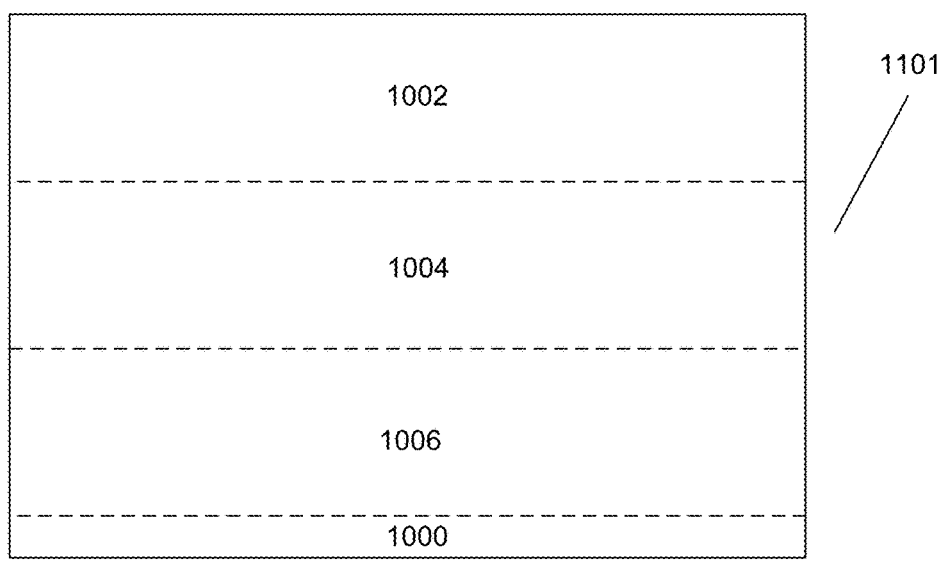
FIG. 11A shows an example of a polygonal label with three test strips of equal width traced in the cross direction, beginning from the top edge of the label, and featuring an area of non-conformance along the bottom edge of the label, the width of which is less than the width of any of the three tests strips.

In FIG. 11A, three strips, each equal to the width of the template and corresponding to reference numbers 1002, 1004, 1006, are traced along the cross direction 202 beginning from the top edge of label 1101. An area of non-conformity corresponding to reference number 1000 remains along the bottom edge of label 1101.

Figure 11B:
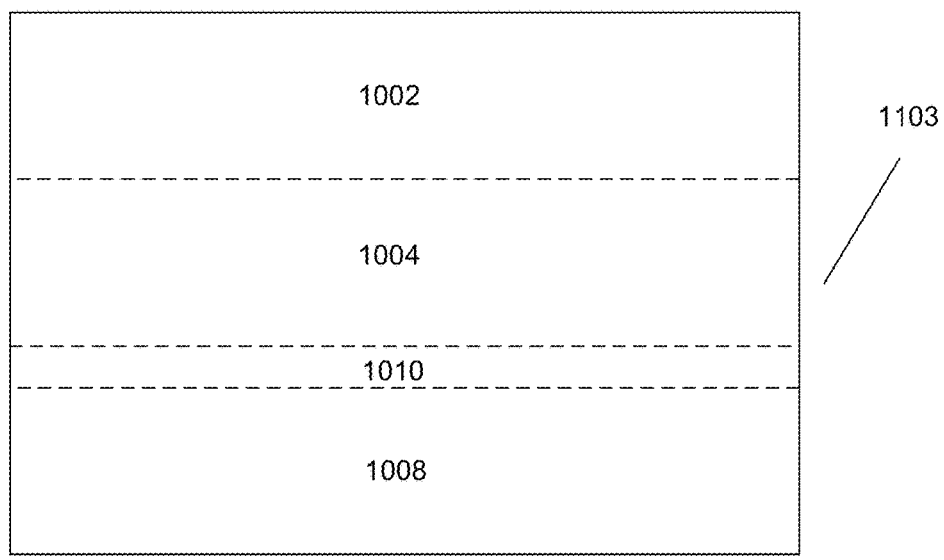
FIG. 11B shows an example of a polygonal label with three test strips of equal width traced in the cross direction and an area of non-conformance, which has a width that is less than the width of any of the test strips, in which the placement of the area of non-conformance has been shifted upward of its original position in FIG. 11A by one multiple of the width of the conforming test strips.

In FIG. 11B the strips corresponding to reference numbers 1002 and 1004 occupy the same area and respective positions along label 1103 as in label 1101 presented previously in FIG. 11A. An area of non-conformity is designated by reference number 1010 on label 1103. The position of area of non-conformity 1010 in label 1103 is displaced upward by one multiple of the width of the template used to trace the test strips, relative to the position of the original area on non-conformity 1000 within label 1101 of FIG. 11A. Traced onto label 1103 is test strip 1008, which is not in common to labels 1101 and 1103. Test strip 1008 is traced along the bottom edge of label 1103 and includes the entire area and position occupied by area of non-conformity 1000 of label 1101 and a portion of the area and position occupied by strip 1006 as traced onto label 1101.

Figure 11C:
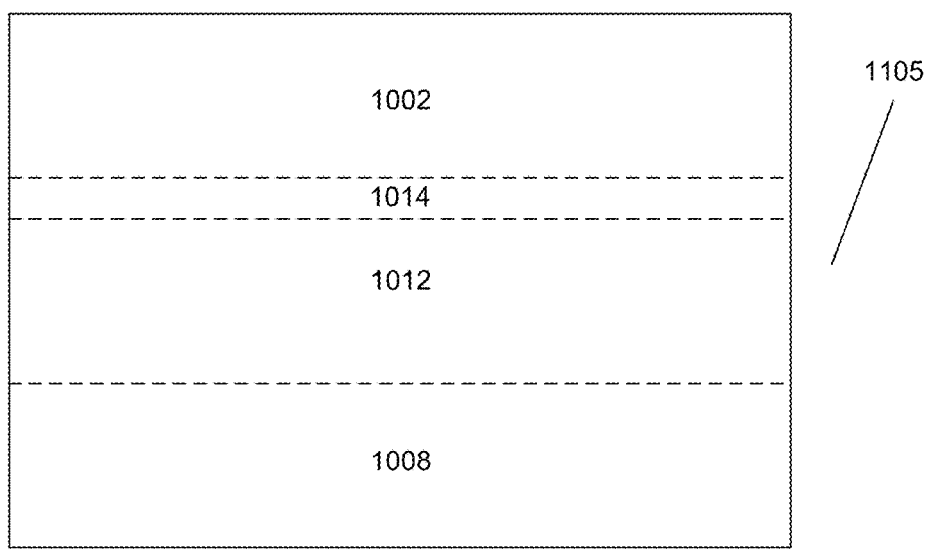
FIG. 11C shows an example of a polygonal label with three test strips of equal width traced in the cross direction and an area of non-conformance, which has a width that is less than the width of any of the test strips, in which the placement of the area of non-conformance has been shifted upward of its original position in FIG. 11A by two multiples of the width of the conforming test strips.

In FIG. 11C the strip corresponding to reference number 1002 occupies the same area and respective position on label 1105 as along labels 1101 and 1103 as presented previously in FIG. 11A-B. No test strip other than that designated by reference number 1002 is in common between labels 1101, 1103, and 1105. Strips 1002 and 1008 occupy the same areas and respective positions on labels 1103 and 1105. No tests strips other than those designated by reference numbers 1002 and 1008 are in common between labels 1103 and 1105. An area of non-conformity along label 1105 is designated by reference number 1014. The position of area of non-conformity 1014 within label 1105 is displaced upward by two multiples of the width of the template used to trace the test strips, relative to the position of the original area of non-conformity 1000 of label 1101.

Traced onto label 1105 is test strip 1012, which is not in common either to labels 1101 or 1103. Test strip 1012 is traced along the bottom edge of area of non-conformity 1014 and the top edge of strip 1008 and includes the entire area and position occupied by area of non-conformity 1010 of label 1103 and a portion of the area and position occupied by strip 1004 as traced onto labels 1101 and 1103.

Figure 11D:
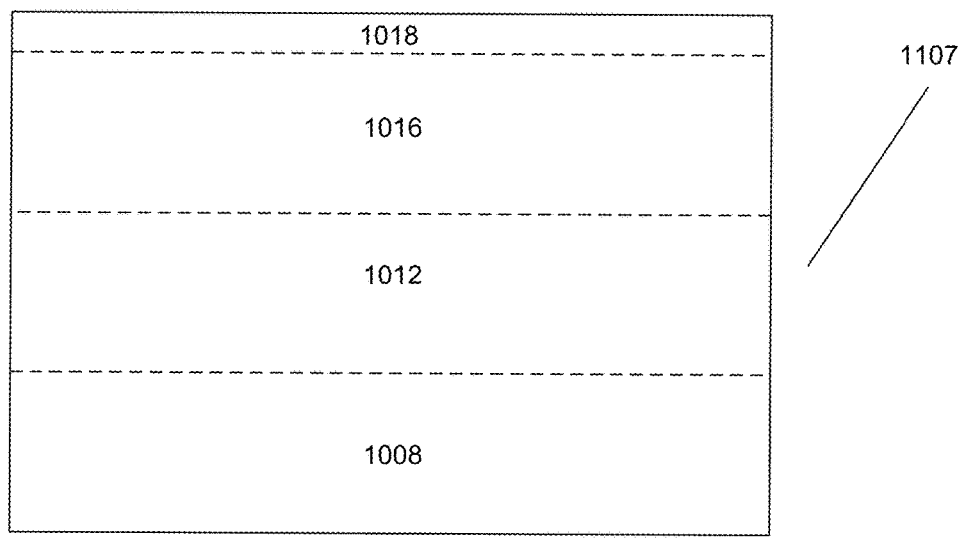
FIG. 11D shows an example of a polygonal label with three test strips of equal width traced in the cross direction and an area of non-conformance, which has a width that is less than the width of any of the test strips, in which the placement of the area of non-conformance has been shifted upward of its original position in FIG. 11A by three multiples of the width of the conforming test strips.

In FIG. 11D the strip corresponding to reference number 1008 occupies the same area and respective position on label 1107 as along labels 1103 and 1105 presented previously in FIG. 11B-C. No test strip other than that designated by reference number 1008 is in common between labels 1103, 1105, and 1107. Also in FIG. 11D, the strip corresponding to reference number 1012 occupies the same area and respective position on label 1107 as along label 1105. No test strips other than 1012 and 1008 are in common between labels 1105 and 1107.

An area of non-conformity along label 1107 is designated by reference number 1018. The position of area of non-conformity 1018 within label 1107 is displaced upward by three multiples of the width of the template used to trace the test strips, relative to the position of the original area of non-conformity 1000 of label 1101. Traced onto label 1107 is test strip 1016, which is not in common either to labels 1101, 1103, or 1105. Test strip 1016 is traced along the bottom edge of area of non-conformity 1018 and the top edge of strip 1012 and includes the entire area and position occupied by area of non-conformity 1014 of label 1105 and a portion of the area and position occupied by strip 1002 as traced onto labels 1101, 1103, and 1105.

Thus the following relationships may be derived:

Replicates of strip 1002 traced onto labels 1101, 1103, and 1105 as presented in FIG. 11A-C may be averaged together as each occupies the same position along these duplicate polygonal labels.

Replicates of strip 1004 traced onto labels 1101 and 1103 as presented in FIG. 11A-B may be averaged together as each occupies the same position along these duplicate polygonal labels.

Replicates of strip 1012 traced onto labels 1105 and 1107 as presented in FIG. 11C-D may be averaged together as each occupies the same position along these duplicate polygonal labels.

Replicates of strip 1008 traced onto labels 1103, 1105, 1107 as presented in FIG. 11B-D may be averaged together as each occupies the same position along these duplicate polygonal labels.

Replicates of strip 1006 traced onto label 1101 as presented in FIG. 11A cannot be averaged with replicates of strips corresponding to any of the other reference numbers previously provided in FIG. 11A-D.

Replicates of strip 1016 traced onto label 1107 as presented in FIG. 11D cannot be averaged with replicates of strips corresponding to any of the other reference numbers previously provided in FIG. 11A-D.

The chart below offers a matrix which summarizes the relationships outlined above:

| Labels | Strips | | | | | |
|---|---|---|---|---|---|---|
| | 1002 | 1004 | 1006 | 1008 | 1012 | 1016 |
| 1101 | X | X | X | | | |
| 1103 | X | X | | X | | |
| 1105 | X | | | X | X | |
| 1107 | | | | X | X | X |

To increase the number of replicates available to study a particular position along the cross direction of the label in the embodiment of Scenario 1 demonstrated throughout FIG. 11A-D, for example, the position occupied by test strip 1016, which is created in FIG. 11D as a result of toggling the area of non-conformity several times previously, it is incumbent on the analyst to reproduce the configuration of test strips as traced onto label 1107 onto enough duplicate labels to satisfy the statistical confidence desired by the analyst.

Figure 12A:
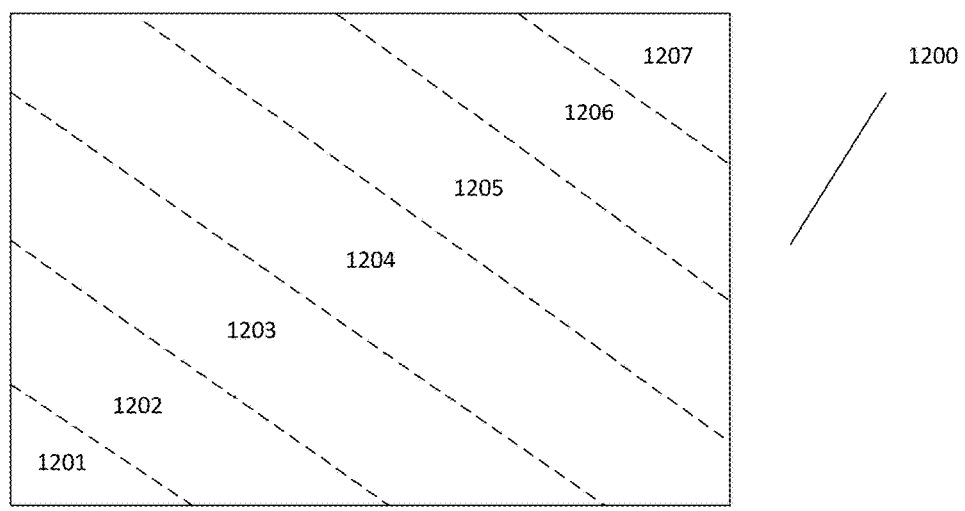
FIG. 12A shows an example of a polygonal label with five test strips of equal width traced in the diagonal direction between the upper left and lower right corners of the label. The upper right and lower left corners of the label contain areas of non-conformity with the width of the template used to trace the conforming test strips.
Figure 12B:
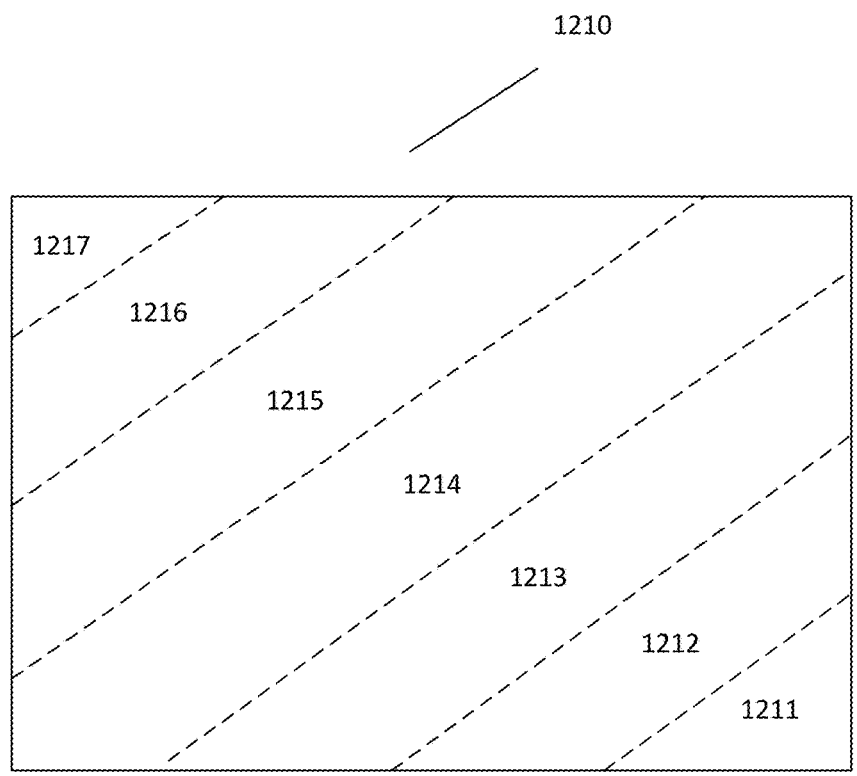
FIG. 12B shows an example of a polygonal label with five test strips of equal width traced at a non-specified angle in the diagonal direction between the upper right and lower left corners of the label. The upper left and lower right corners of the label contain areas of non-conformity with the width of the template used to trace the conforming test strips.

Another possible embodiment of the principle described in Scenario 1 is shown in FIG. 12A-B using duplicates of a polygonal shaped label with strips traced in the diagonal direction 204.

Reference number 1200 in FIG. 12A corresponds to a duplicate of a polygonal shape label. Five strips of varying lengths with widths equal to the width of the template are traced diagonally from the upper left to the lower right corners of label 1200. Two non-conforming areas, 1207 and 1201, are located at the upper right and lower left corners, respectively, of label 1200.

In FIG. 12B, non-conforming areas 1217 and 1211 are located at the upper left and lower right corners, respectively, of label 1210. Five strips of varying lengths with widths equal to the template's width are traced diagonally from the upper right to the lower left corners of label 1210.

The test strips traced onto label 1200 FIG. 12A are non-superimposable mirror images of the test strips traced onto label 1210 of FIG. 12B. Though the members of strip pairs 1206 and 1216, 1205 and 1215, 1204 and 1214, 1203 and 1213, and 1202 and 1212 may be equal in area, they do not occupy the same positions along the label. Therefore, replicates of each strip shown in FIG. 12A-B must be considered separately. It is incumbent on the analyst to reproduce the configuration of test strips as shown in FIG. 12A-B on enough duplicates of the same polygonal shaped label to satisfy the statistical confidence desired by the analyst.

Additionally, another set of replicates should be created identical to the previous experiments but the direction in which the strips are to be peeled is reversed. That is, if, for example, the test strips were created along the machine direction and were peeled from the top end of the label to the bottom, then another set of strips should be created and peeled from the bottom end of the label to the top, and the data compared to determine if ease of removal differs if the label is removed starting from the top or the bottom. Likewise, two sets of test strips along the cross direction should be created to determine if there is a difference in the resistance to peel force when the strips are peeled from right to left and from the left to the right.

The analyst shall continue the analysis of the resistance to peel strength across the entire label by creating diagonal strips. Diagonal strips are useful to help determine how much effect the anisotropy of the label (if performing the indirect peel) or of the substrate (if performing the reverse-direct peel) has on the resistance to peel strength along the entire area of the label.

The angle at which diagonal strips are created is to the analyst's discretion. If the angle chosen is 45 degrees relative the machine direction, the analyst shall prepare a second set of strips in the angle of reflection if the machine direction were a mirror plane, in this case at 135 degrees. The analyst shall then consider the cross direction as a mirror plane and prepare third and fourth sets of diagonal strips traced at 225 and 315 degrees, respectively. This will then satisfy the question of what effect, if any, does reversing the peel direction have on a diagonal strip.

If the 45 degree strips are peeled in the direction from the top right corner to the bottom left corner, the 225 degree strips will be peeled in the opposite direction, from the bottom left to the top right. The 135 degree strips shall be peeled in the opposite direction of the 315 degree strips as well. This will allow the analyst to assess both the impact of the location of the peel along the label and the direction of the peel on the resistance to peel strength.

However, for the most comprehensive examination, particularly for labels and substrates which have heterogeneous elements, a 360 degree analysis is recommended. The 360 degree analysis involves peeling in intervals set by the analyst such that peeling is attempted along all points of the label and in all possible directions.

FIG. 13A-G illustrate one possible embodiment of this principle using multiple sets of duplicates of the same label.

Figure 13A:
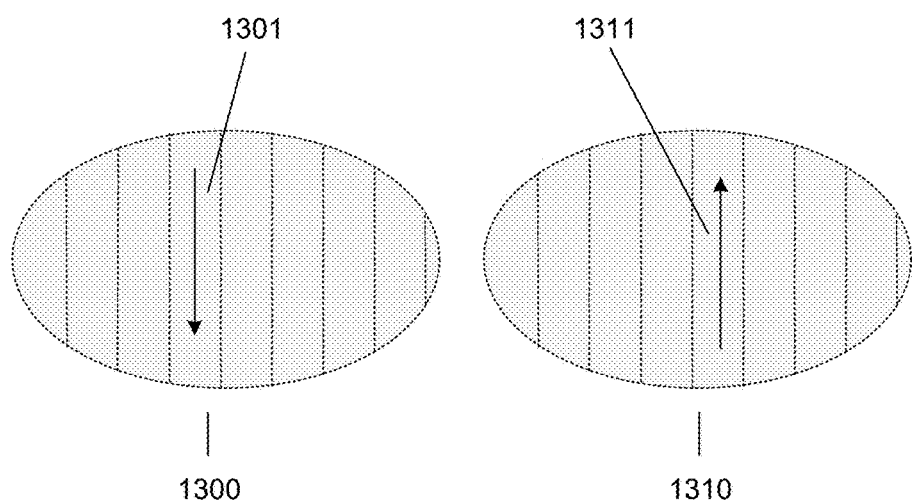
FIG. 13A presents two duplicates of an elliptically-shaped label in which strips are traced onto each in the machine direction and in which the peel direction differs between each duplicate.
Figure 13B:
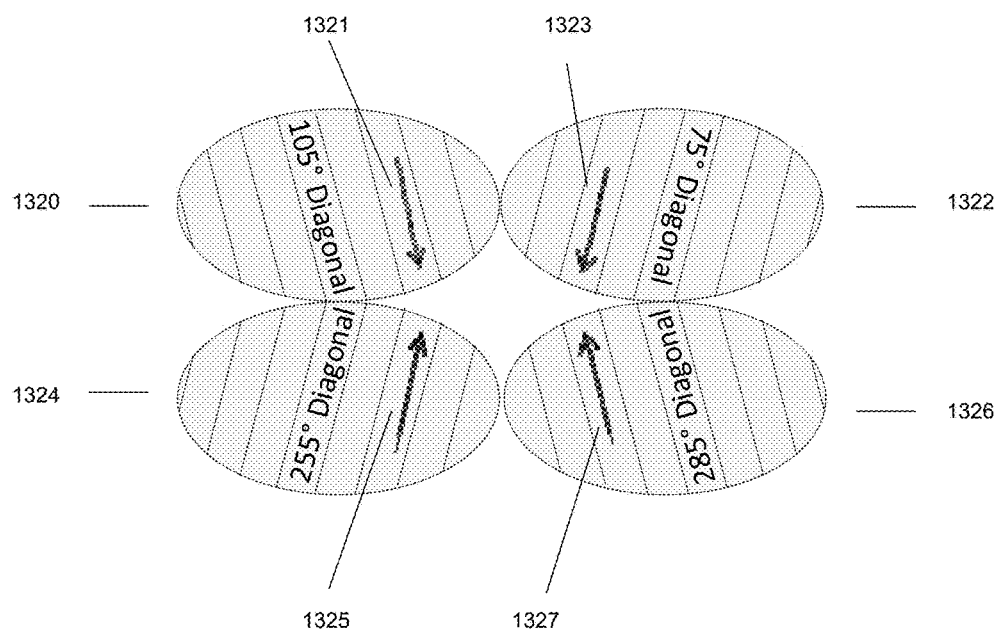
FIG. 13B presents four duplicates of an elliptically-shaped label where the angle at which strips are traced deviate 15 degrees away from the machine direction such that test strips are traced at 75, 105, 255, and 285 degree diagonals. The peel directions of the 75 and 255 degree diagonal strips are opposite of each other. The peel directions of the 105 and 285 degree diagonal strips are also opposite of each other.
Figure 13C:
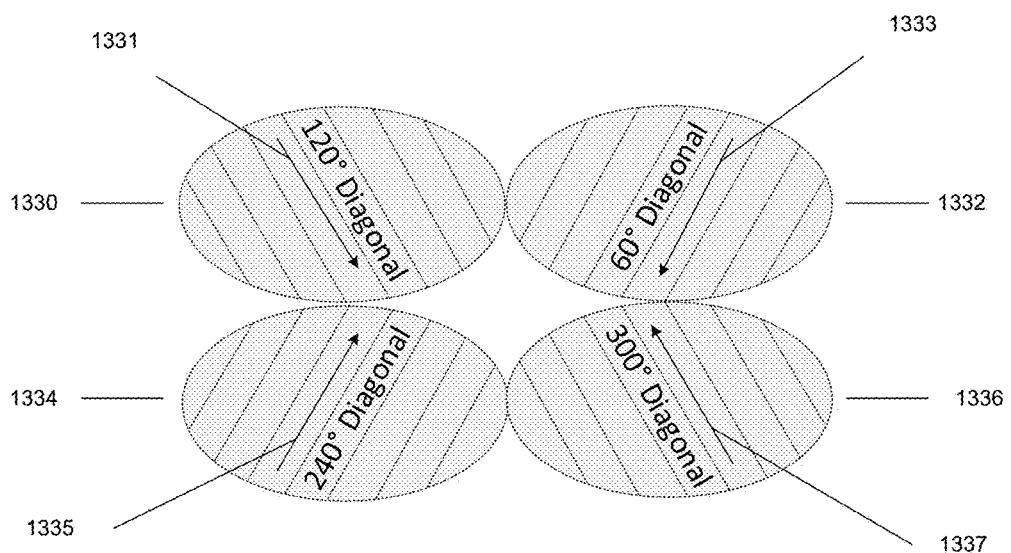
FIG. 13C presents four duplicates of an elliptically-shaped label where the angle at which strips are traced deviate 30 degrees away from the machine direction such that test strips are traced at 60, 120, 240, and 300 degree diagonals. The peel directions of the 60 and 240 degree diagonal strips are opposite of each other. The peel directions of the 120 and 300 degree diagonal strips are also opposite of each other.
Figure 13D:
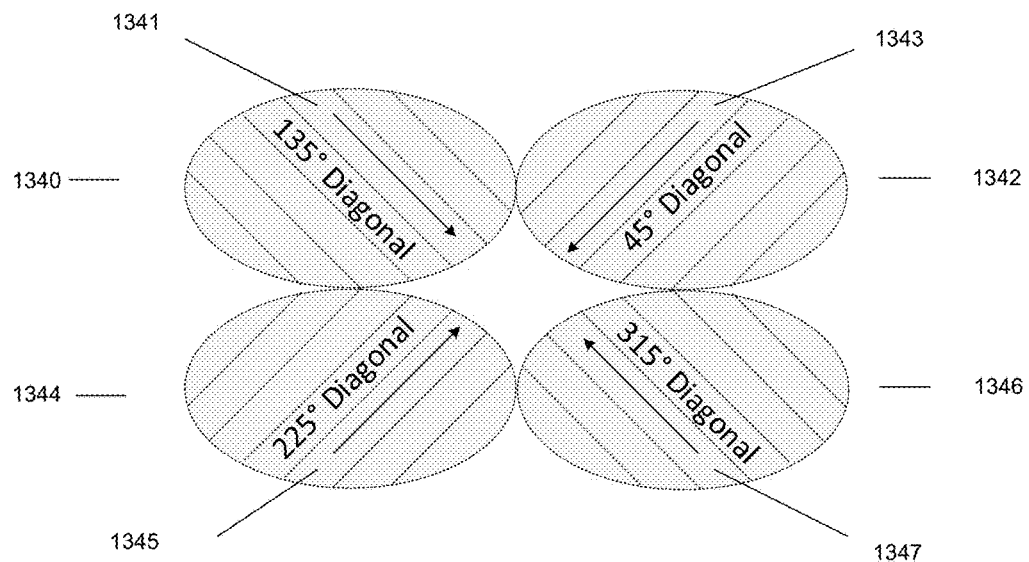
FIG. 13D presents four duplicates of an elliptically-shaped label where the angle at which strips are traced deviate 45 degrees away from the machine direction such that test strips are traced at 45, 135, 225, and 315 degree diagonals. The peel directions of the 45 and 225 degree diagonal strips are opposite of each other. The peel directions of the 135 and 315 degree diagonal strips are also opposite of each other.
Figure 13E:
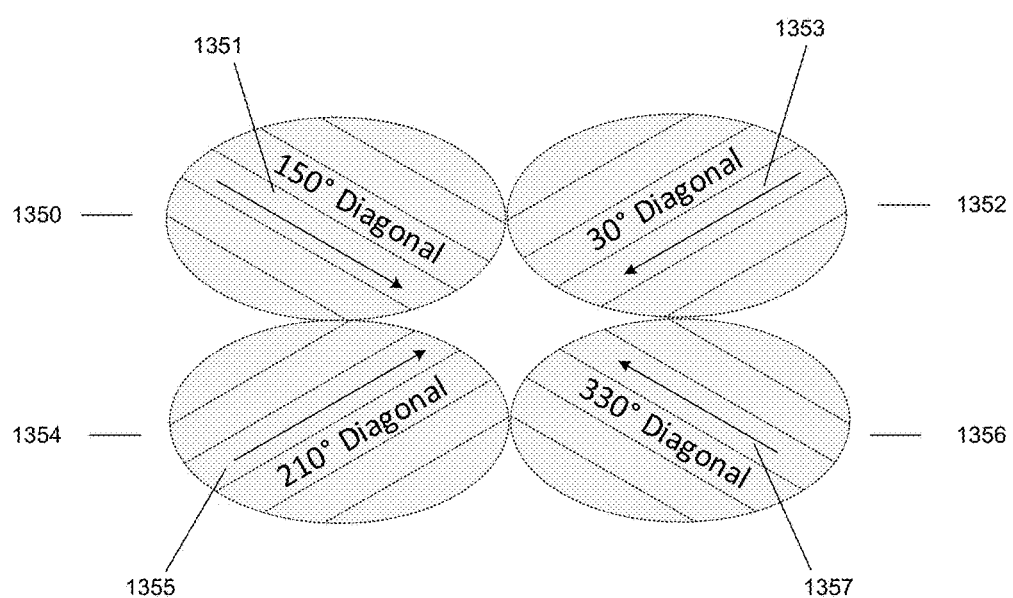
FIG. 13E presents four duplicates of an elliptically-shaped label where the angle at which strips are traced deviate 60 degrees away from the machine direction such that test strips are traced at 30, 150, 210, and 330 degree diagonals. The peel directions of the 30 and 210 degree diagonal strips are opposite of each other. The peel directions of the 150 and 330 degree diagonal strips are also opposite of each other.
Figure 13F:
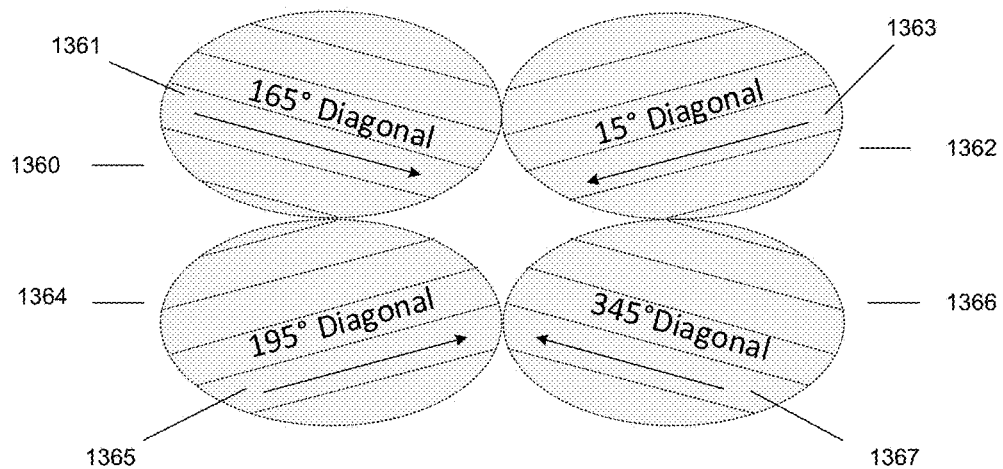
FIG. 13F presents four duplicates of an elliptically-shaped label where the angle at which strips are traced deviate 75 degrees away from the machine direction such that test strips are traced at 15, 165, 195, and 345 degree diagonals. The peel directions of the 15 and 195 degree diagonal strips are opposite of each other. The peel directions of the 165 and 345 degree diagonal strips are also opposite of each other.
Figure 13G:
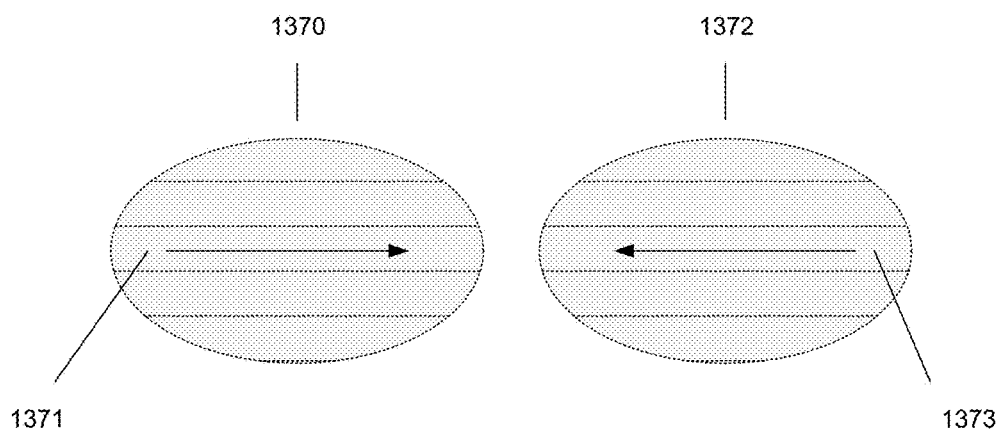
FIG. 13G presents two duplicates of an elliptically-shaped label in which strips are traced onto each in the cross direction and in which the peel direction differs between each duplicate.

To begin the 360 degree analysis, sets of edge-to-edge test strips are prepared in the machine direction (FIG. 13A) and in the cross directions (FIG. 13G).

One set of machine direction strips (traced at 90 degrees/270 degrees), as shown traced onto label 1300, is to be peeled from top to bottom, as indicated by single arrow 1301. The other set of machine direction strips in FIG. 13A, as shown traced onto label 1310, are identical to the strips traced onto label 1300, except that these strips are to be peeled from bottom to top, as indicated by single arrow 1311. Next, sets of edge-to-edge strips are prepared in the cross direction (180 degrees/0 degrees), as depicted in FIG. 13G. The strips traced onto label 1370 are identical to the strips traced onto label 1372. The strips traced onto label 1370 are to be peeled from left to right, as indicated by single arrow 1371, and the strips traced onto label 1372 are to be peeled from the right to the left, as indicated by single arrow 1373.

In this particular embodiment of the 360 degree analysis, the analyst has chosen to vary the angle in the diagonal direction by 15 degrees. Therefore, multiple sets of strips are traced for diagonals of 15, 30, 45, 60, and 75 degrees along with their associated variants (FIG. 13B-F) on duplicate sets of labels. The analyst then has the choice of performing one or both of the peel methods described in this document.

FIG. 13B depicts strips traced at diagonals which are displaced from the normal created by the intersection of the machine and cross directions by 15 degrees. Therefore, four sets of diagonal test strips are created at 75, 105, 255, and 285 degrees along the mirror planes formed by the machine and cross directions. Label 1322 depicts the 75 degree diagonal test strips to be peeled from the upper right to lower left as indicated by single arrow 1323. The 255 degree strips traced onto label 1324 are identical to those of label 1322, except that the direction of the peel, as indicated by single arrow 1325, is in the opposite direction, from the lower left to the upper right. Accordingly, the 105 degree diagonal strips traced onto label 1320 are identical to those traced at the 285 degree diagonal on label 1326, except that the peel directions indicated by single arrows 1321 and 1327 are opposite (upper left to lower right vs. lower right to upper left).

FIG. 13C depicts strips traced at diagonals which are displaced from the normal created by the intersection of the machine and cross directions by 30 degrees. Therefore, four sets of diagonal test strips are created at 60, 120, 240, and 300 degrees along the mirror planes formed by the machine and cross directions. Label 1332 depicts the 60 degree diagonal test strips to be peeled from the upper right to lower left as indicated by single arrow 1333. The 240 degree strips traced onto label 1334 are identical to those of label 1332, except that the direction of the peel, as indicated by single arrow 1335, is in the opposite direction, from the lower left to the upper right. Accordingly, the 120 degree diagonal strips traced onto label 1330 are identical to those traced at the 300 degree diagonal on label 1336, except that the peel directions indicated by single arrows 1331 and 1337 are opposite (upper left to lower right vs. lower right to upper left, respectively).

FIG. 13D depicts strips traced at diagonals which are displaced from the normal created by the intersection of the machine and cross directions by 45 degrees. Therefore, four sets of diagonal test strips are created at 45, 135, 225, and 315 degrees along the mirror planes formed by the machine and cross directions. Label 1342 depicts the 45 degree diagonal test strips to be peeled from the upper right to lower left as indicated by single arrow 1343. The 225 degree strips traced onto label 1344 are identical to those of label 1342, except that the direction of the peel, as indicated by single arrow 1345, is in the opposite direction, from the lower left to the upper right. Accordingly, the 135 degree diagonal strips traced onto label 1340 are identical to those traced at the 315 degree diagonal on label 1346, except that the peel directions indicated by single arrows 1341 and 1347 are opposite (upper left to lower right vs. lower right to upper left, respectively).

FIG. 13E depicts strips traced at diagonals which are displaced from the normal created by the intersection of the machine and cross directions by 60 degrees. Therefore, four sets of diagonal test strips are created at 30, 150, 210, and 330 degrees along the mirror planes formed by the machine and cross directions. Label 1352 depicts the 30 degree diagonal test strips to be peeled from the upper right to lower left as indicated by single arrow 1353. The 210 degree strips traced onto label 1354 are identical to those of label 1352, except that the direction of the peel, as indicated by single arrow 1355, is in the opposite direction, from the lower left to the upper right. Accordingly, the 150 degree diagonal strips traced onto label 1350 are identical to those traced at the 330 degree diagonal on label 1356, except that the peel directions indicated by single arrows 1351 and 1357 are opposite (upper left to lower right vs. lower right to upper left, respectively).

FIG. 13F depicts strips traced at diagonals which are displaced from the normal created by the intersection of the machine and cross directions by 75 degrees. Therefore, four sets of diagonal test strips are created at 15, 165, 195, and 345 degrees along the mirror planes formed by the machine and cross directions. Label 1362 depicts the 15 degree diagonal test strips to be peeled from the upper right to lower left as indicated by single arrow 1363. The 195 degree strips traced onto label 1364 are identical to those of label 1362, except that the direction of the peel, as indicated by single arrow 1365, is in the opposite direction, from the lower left to the upper right. Accordingly, the 165 degree diagonal strips traced onto label 1360 are identical to those traced at the 345 degree diagonal on label 1366, except that the peel directions indicated by single arrows 1361 and 1367 are opposite (upper left to lower right vs. lower right to upper left, respectively).

It is incumbent on the analyst to produce enough replicates of the test strips used in the 360 degree analysis to satisfy the statistical confidence desired by the analyst.

Scenario 2: Excluding an Area within a Label

The analyst may choose to exclude areas of the label for analysis. Reasons for exclusion include, but are not limited to, the physical and technical limitations of the testing equipment, the time and resources available to complete the analysis, and the nature and location of a particular security attribute. Any of the four test strip types can be used to focus on one specific area within the label and exclude the other areas. Interior-to-Interior strips, like edge-to-edge strips, may have their peel direction reversed to determine if the direction of the peel (i.e., top to bottom, bottom to top) plays a role in the ease of removal of the test strip from the substrate.

Figure 14A:
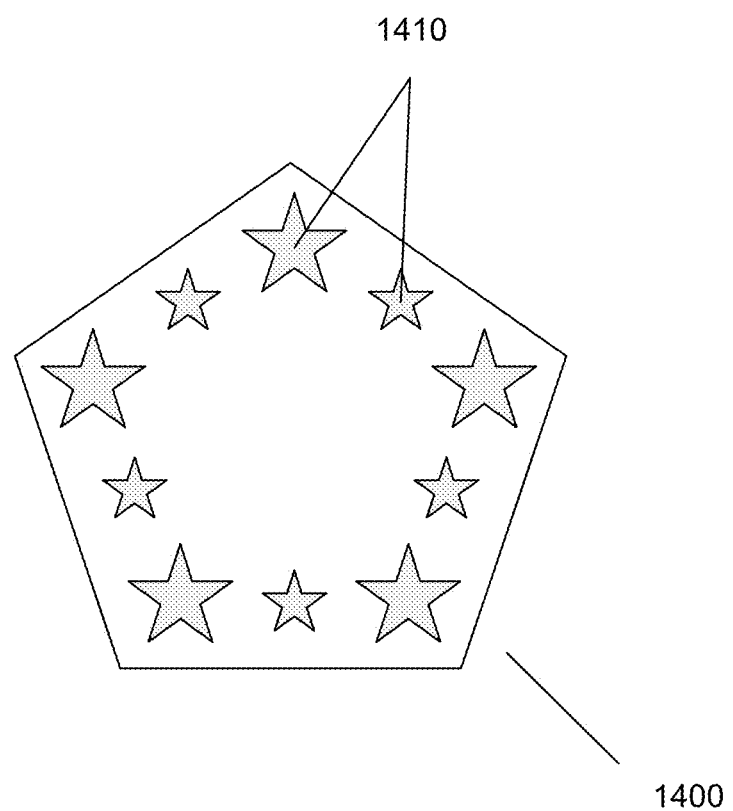
FIG. 14A is an example of a label which is up for redesign.
Figure 14B:
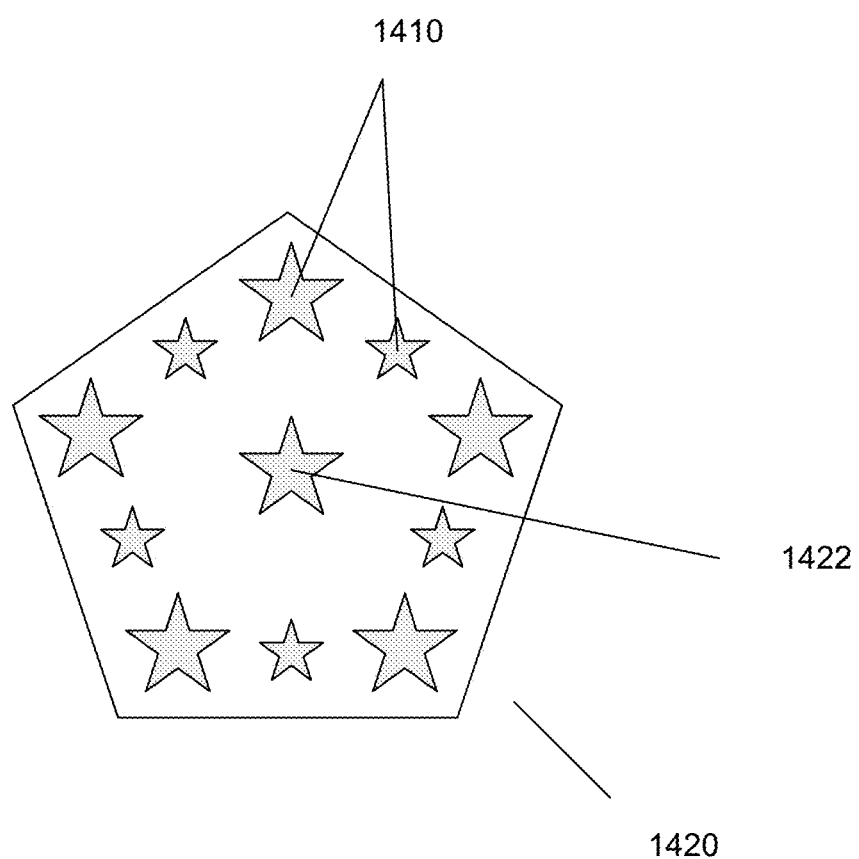
FIG. 14B is a proposed redesign of the label provided in FIG. 14A.
Figure 14C:
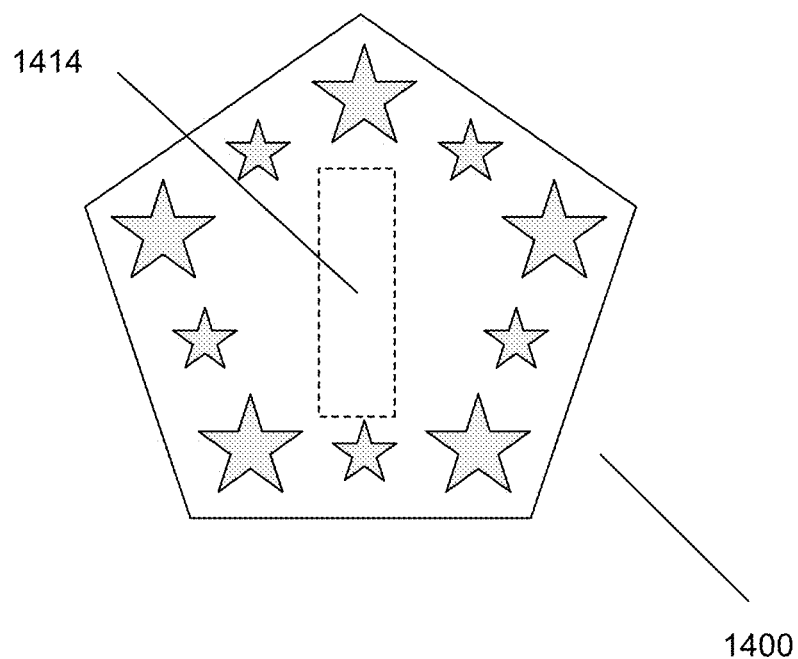
FIG. 14C depicts an interior-to-interior strip traced through the center of the label provided in FIG. 14A.
Figure 14D:
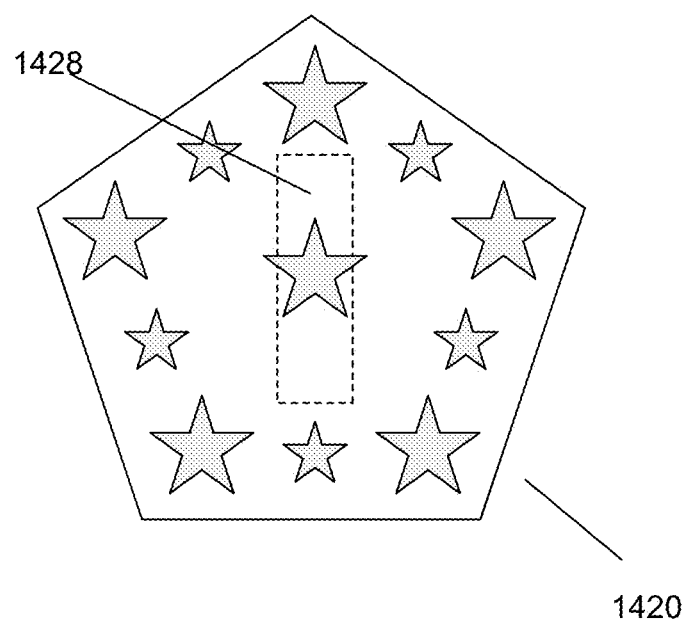
FIG. 14D depicts an interior-to-interior strip traced through the center of the label provided in FIG. 14B.
Figure 14E:
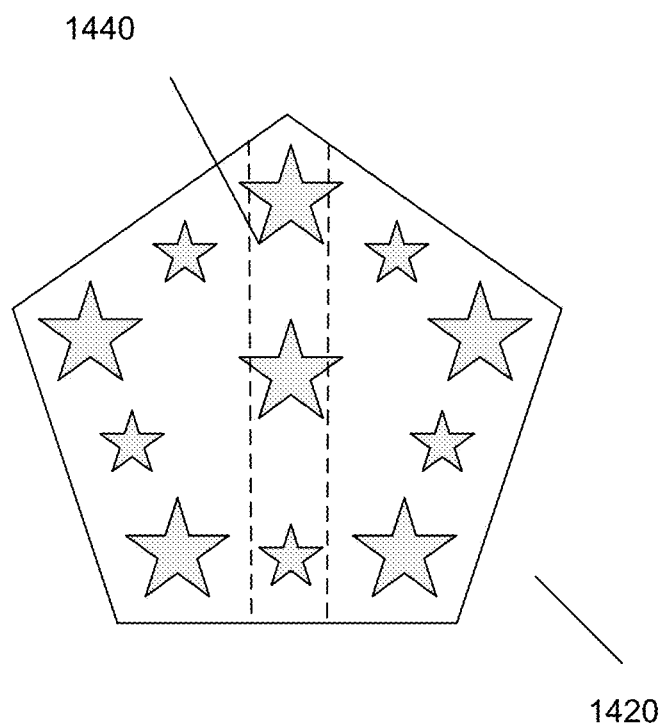
FIG. 14E depicts an edge-to-edge strip traced through the center of the label provided in FIG. 14B.
Figure 14F:
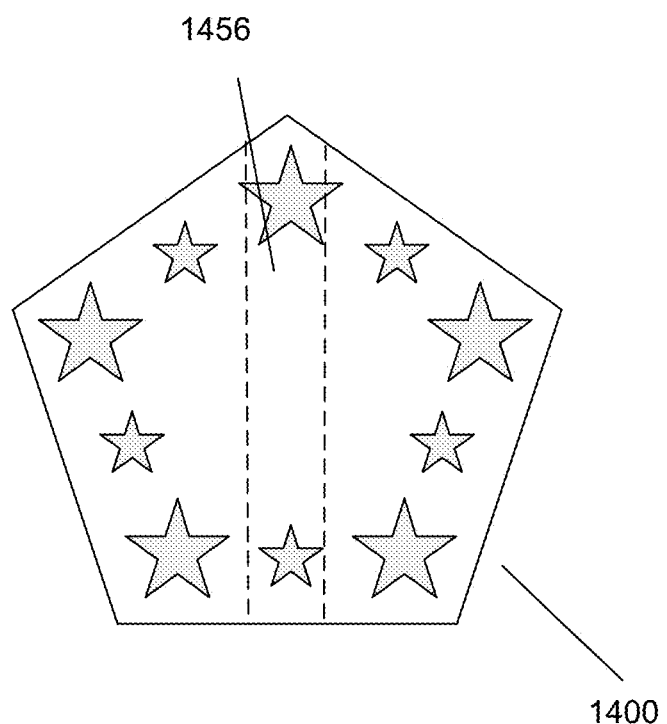
FIG. 14F depicts an edge-to-edge strip traced through the center of the label provided in FIG. 14A.

Strip types may also be combined to provide a more complete analysis of which areas of the label are easier to remove than others through peeling and to evaluate proposed process changes to a label. One possible embodiment is shown in FIG. 14A-F. FIG. 14A demonstrates a possible example of a label, label 1400, which is up for revision to stay ahead of counterfeiters. Label 1400 features an alternating star motif 1410, which is printed via a security printing technique around the perimeter. The downside of using this technique is that though it is difficult to counterfeit, the presence of this type of printing has been observed to stiffen the edges of the label, making it easier for a forger or counterfeiter to remove label 1400 from its intended substrate. The proposed design change is shown as label 1420, depicted in FIG. 14B, where an additional star, indicated by reference number 1422 and printed using the same security printing technique, is to be included in the center. As shown in FIG. 14C, the analyst may choose to exclude the borders of the label and prepare an interior-to-interior strip, corresponding to reference number 1414, to study the resistance to peel strength of the center area of label 1400, which reflects the currently issued design. This would then be compared to the results from replicates of interior-to-interior strip 1428 prepared from label 1420, which is reflective of the proposed design change, as shown in FIG. 14D. Afterward, the analyst would proceed to create replicates of edge-to-edge strip 1440 as depicted in label 1420 in FIG. 14E and compare the results to those from replicates of edge-to-edge strip 1456 traced onto duplicates of label 1400, as shown in FIG. 14F. With an understanding of the resistance to peel strength along different areas of the current and newly proposed designs, the analyst may suggest possible remedies including, but not limited to, changing the printing modalities used on the label and acquiring a stronger adhesive.

Figure 15:
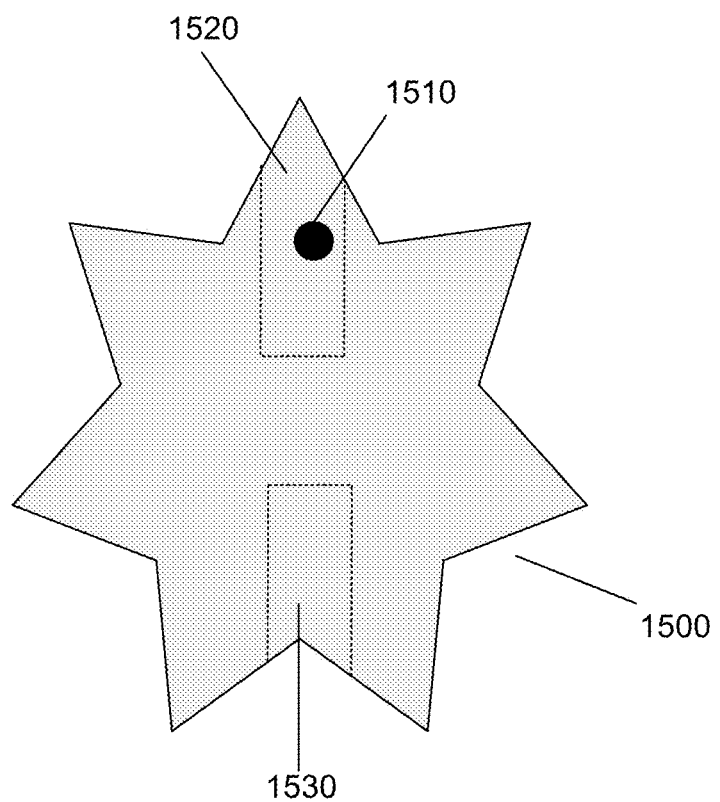
FIG. 15 shows a label bearing a security feature that a forger wishes to liberate and test strips traced along areas of interest to the analyst.

The choice of strip(s) depends upon the location of the area of interest on the label and the suspected motivations of a potential forger or counterfeiter. In one possible embodiment of this principle, an offset-printed label is populated with specific, personalized data by hand or by a machine operated by an employee of the issuing authority. The label stock is impregnated with chemically sensitive agents such that any attempt to remove the personalized data with ordinary household chemicals will result in an indelible stain on the label. However, the label also includes an easily identifiable and distinct security feature, which a counterfeiter cannot reasonably and reliably reproduce, such as a hologram or a microelectronic component. The counterfeiting strategy utilized by the potential forger within this example would be to print the label via an offset press and insert the security feature removed from a genuine-issue label and add the personalized data the forger wishes to use. Therefore, it is important to understand the resistance to peel strength of the label in the area where the security feature is located to determine the likelihood of its intact removal by an individual engaged in forging or counterfeiting activities. One possible embodiment of this situation is provided in FIG. 15 which depicts label 1500 bearing security feature 1510, represented by the black circle, which the potential forger wishes to liberate. As the label in its entirety is not of interest to the potential forger, sets of edge-to-interior strips, one set of which corresponds to reference number 1520 that includes security feature 1510, and another set corresponding to reference number 1530 which does not bear security feature 1510, may be prepared to gauge the ease of removal of security feature 1510.

Description of the Indirect Method

The indirect method may be applied to the following types of test strips: "Edge-to-Edge" strips, "Edge-to-Interior" strips, "Interior-to-Edge" strips, and "Interior-to-Interior" strips.

Regardless of the test strip type created, the analyst must wear gloves during all points of sample preparation. This is to prevent the contamination of the adhesive and the surface of the substrate to which the label will be affixed. Once an area of interest on the label has been chosen, strips should be traced using a template of the chosen width and length to ensure dimensional uniformity. The template may be aligned against a "landmark" feature along the design of the label to ensure that replicate sample test strips traced from other labels will be identical to each other, as described previously.

Any number of replicate test strips of the same area of investigation may be prepared depending upon the scale of the experiment and the level of statistical confidence sought by the analyst. For a full analysis of the resistance to peel strength of a label, it is recommended that a set of experiments be performed whereby the entire label is sectioned into "edge-to-edge" strips across in the machine direction, cross direction, and diagonal directions for a 360 degree analysis as discussed previously in Scenario I.

Step 1: Identifying an Area of the Label to Create a Strip

The analyst will identify an area of interest on the label to create a test strip.

Figure 16:
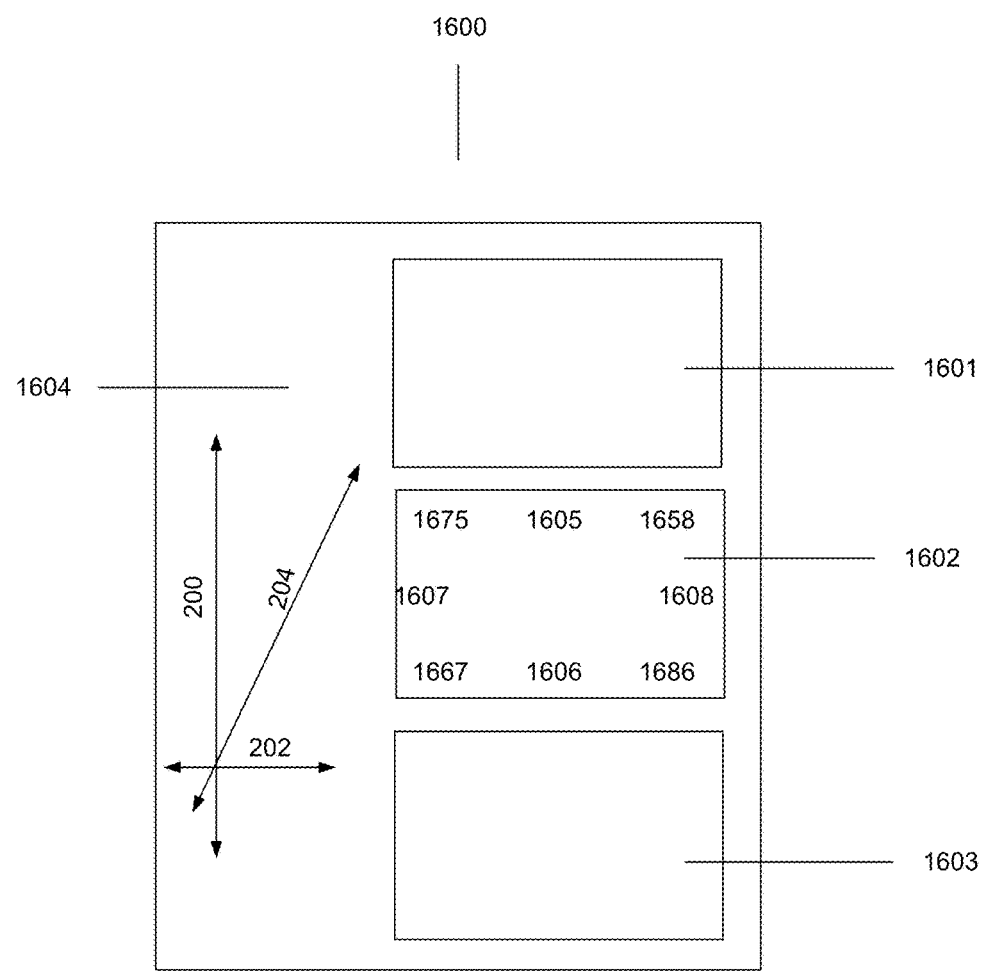
FIG. 16 provides an example of a PSA labels printed three to a sheet.
Figure 17:
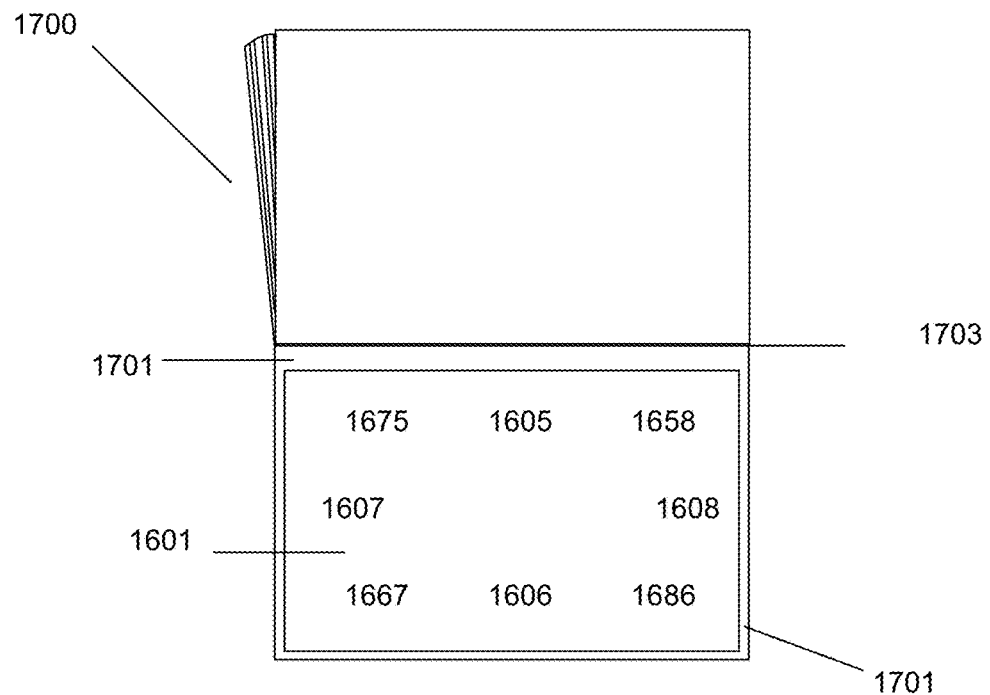
FIG. 17 illustrates the proper placement of a PSA label shown in FIG. 16 into a page of a booklet in order to authenticate the booklet.

One possible embodiment is shown in FIG. 16-17. FIG. 16 depicts polygonal-shaped labels 1601, 1602, and 1603 which are printed and die cut three to a sheet on converted face stock sheet 1600. Unprinted area 1604 of the label stock is immediately to the left of labels 1601, 1602, and 1603 on sheet 1600. Machine 200, cross 202, and diagonal 204 directions are provided as a reference, as are the orientations of the labels with respect to the sheet onto which they have been manufactured (top 1605, bottom 1606, left 1607, right 1608, top left 1675, top right 1658, bottom left 1667, and bottom right 1686).

In FIG. 17, label 1601 is shown within a normal circumstance of its intended use, authenticating page 1701 of booklet 1700. Page 1701 functions as the substrate onto which the label is adhered. Label 1601 is applied onto page 1701 of booklet 1700 with the top edge of the label aligned parallel to the booklet's spine, which is represented by reference number 1703.

For this particular embodiment, the analyst has chosen to examine the far left edge of the label and will then proceed to step 2.

Step 2: Tracing the Test Strip with the Template

Figure 18:
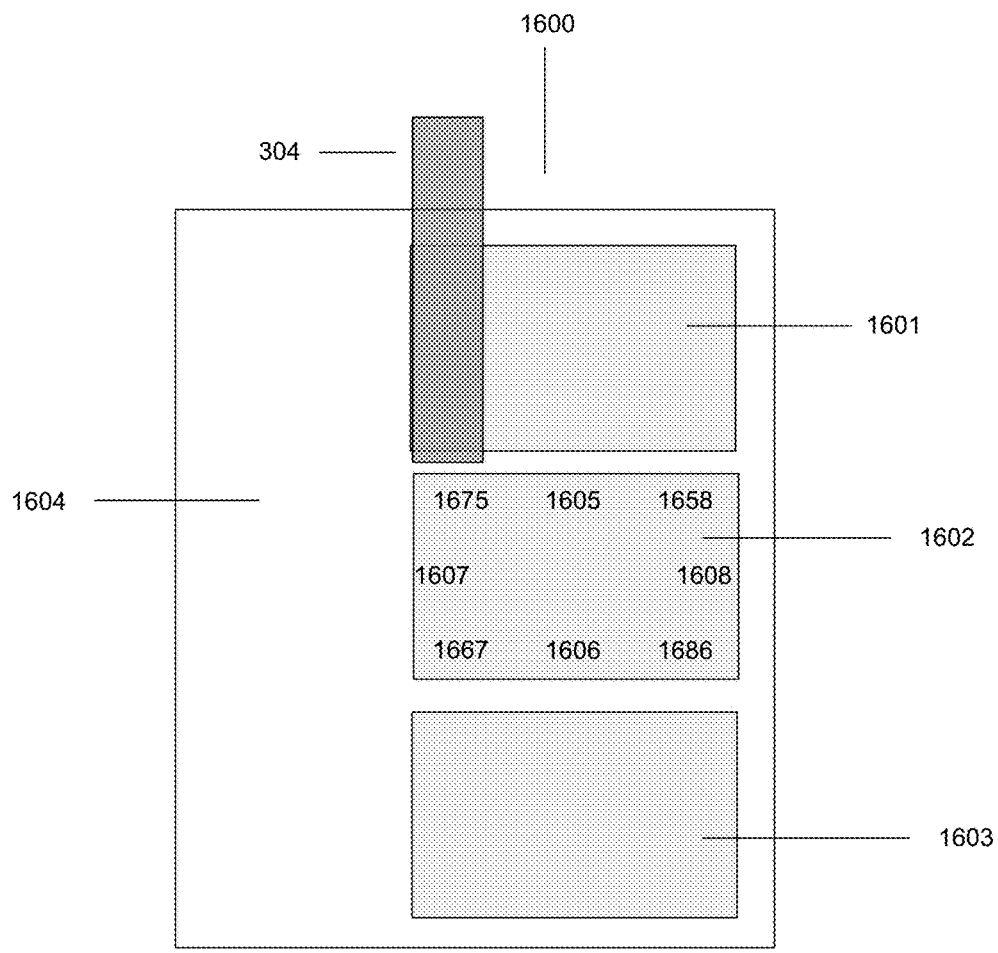
FIG. 18 demonstrates the process of tracing a test strip using a template on one of the sample labels provided in the three-up sheet originally depicted in FIG. 16.

The test strip shall be traced with the aid of template 304. The template serves as a guide to ensure uniformity among replicates within an experiment. In FIG. 18, the analyst aligns template 304 with the far left edge of label 1601 of sheet 1600. Any of the four test strip types can be traced from this area.

FIG. 19A-D provide possible embodiments of what test strips may look like if drawn from the chosen area of interest, the left edge of label 1601.

Figure 19A:
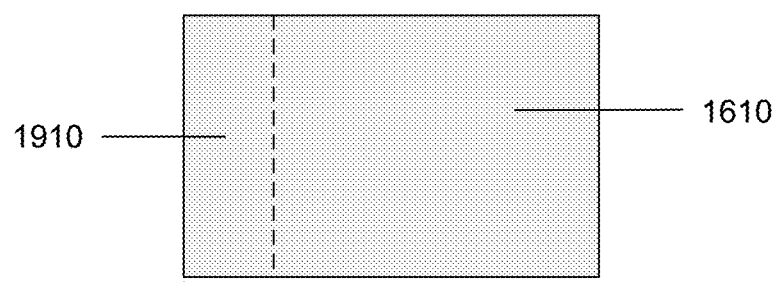
FIG. 19A depicts an edge-to-edge strip traced in the machine direction onto the far left side on a duplicate of a PSA label as shown in FIG. 16.

FIG. 19A depicts edge-to-edge strip 1910 as it would be traced on label 1610, a duplicate of label 1601.

Figure 19B:
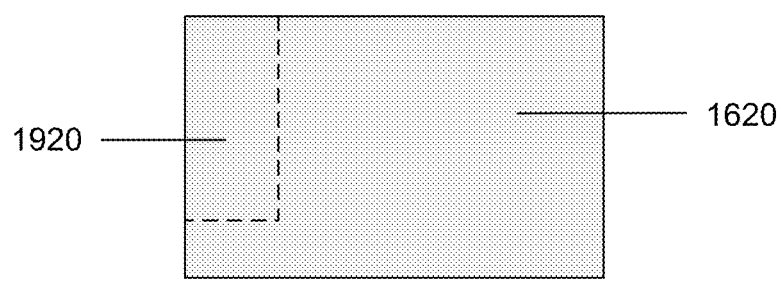
FIG. 19B depicts an edge-to-interior strip traced in the machine direction onto the far left side on a duplicate of a PSA label as shown in FIG. 16.

FIG. 19B depicts edge-to-interior strip 1920 as it would be traced onto label 1620, a duplicate of label 1601.

Figure 19C:
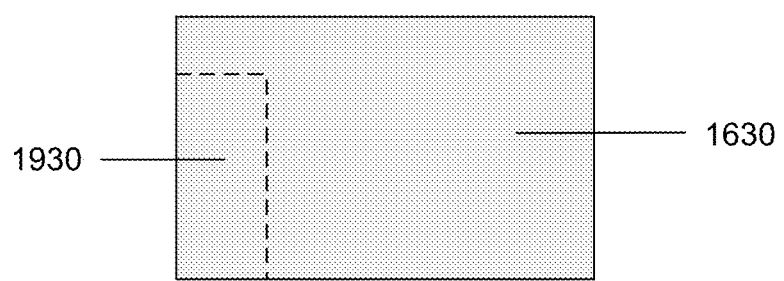
FIG. 19C depicts an interior-to-edge strip traced in the machine direction onto the far left side on a duplicate of a PSA label as shown in FIG. 16.

FIG. 19C depicts interior-to-edge strip 1930 as it would be traced onto label 1630, a duplicate of label 1601.

Figure 19D:
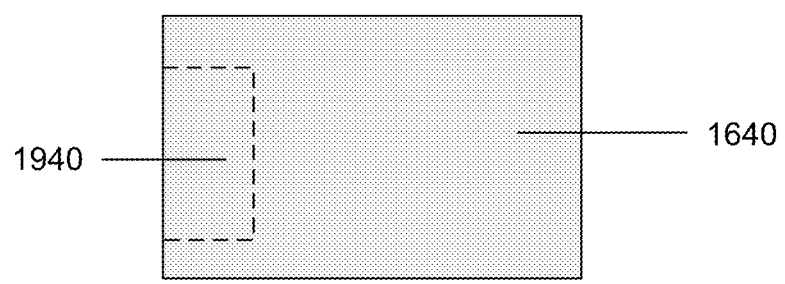
FIG. 19D depicts an interior-to-interior strip traced in the machine direction onto the far left side on a duplicate of a PSA label as shown in FIG. 16.
Figure 20A:
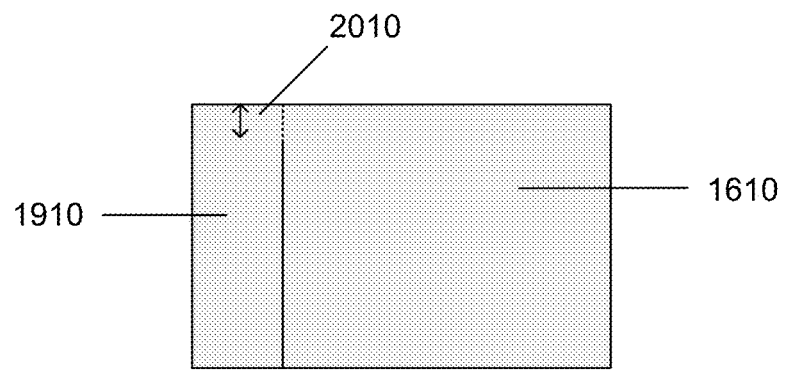
FIG. 20A shows the position of a tab created on an edge-to-edge strip traced in the machine direction onto the far left side on a duplicate of a PSA label as shown in FIG. 16.
Figure 20B:
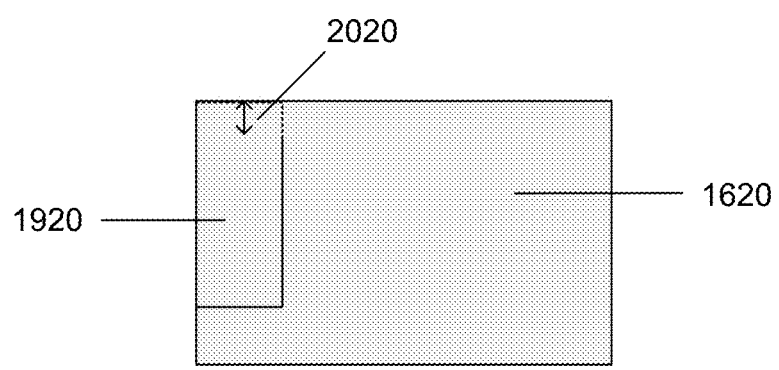
FIG. 20B shows the position of a tab created on an edge-to-interior strip traced in the machine direction onto the far left side on a duplicate of a PSA label as shown in FIG. 16.
Figure 20C:
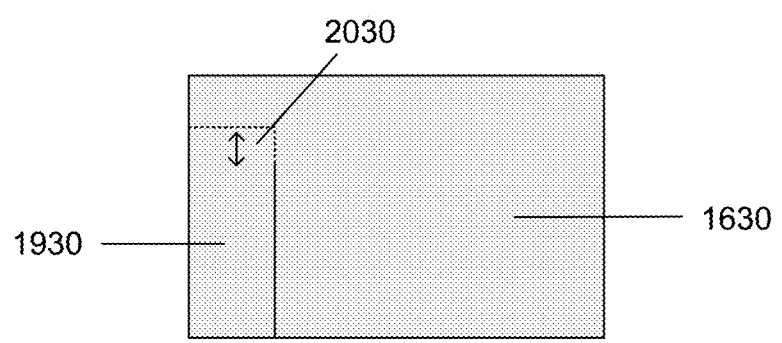
FIG. 20C shows the position of a tab created on an interior-to-edge strip traced in the machine direction onto the far left side on a duplicate of a PSA label as shown in FIG. 16.
Figure 20D:
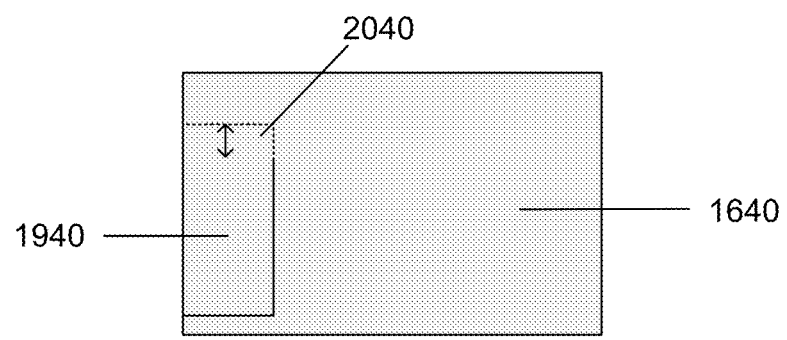
FIG. 20D shows the position of a tab created on an interior-to-interior strip traced in the machine direction onto the far left side on a duplicate of a PSA label as shown in FIG. 16.

FIG. 19D depicts interior-to-interior strip 1940 as it would be traced onto label 1640, a duplicate of label 1601.

For each the strips shown traced in FIG. 19A-D, the direction of the peel is assumed to be from top 1605 to bottom 1606 along machine direction 200. It is also assumed that the labels depicted in FIG. 19A-D have not been removed or lifted from sheets onto which they have been printed and die cut.

Step 3: Creating a Tab

After identifying the desired location for a test strip and tracing it with the assistance of a template, the analyst will choose the end of the strip from which the peeling will commence. On this end of the strip, the analyst will create a tab.

The purpose of the tab is to provide a means by which the release and adhesion tester will pull the sample away from the substrate. The presence of the tab is also meant to mimic the start of an attempted removal of the label from the substrate.

FIG. 20A-D depict examples of each of the four test strip types traced along the area of interest identified in step 1. Assume labels shown have not been removed from their backing sheets.

Tabs corresponding to reference numbers 2010, 2020, 2030, and 2040 have been created with a razor blade or similar cutting instrument from the end desired to initiate the peel along test strips 1910, 1920, 1930, and 1940, respectively.

Tabs 2010, 2020, 2030, and 2040 in FIG. 20A-D are depicted prior to being lifted away from the silicone backing sheet. The length or depth, d, of tabs 2010, 2020, 2030, and 2040 is between ¼" and ½. However, for each replicate within an experiment, the tab length should remain constant to decrease variation in measurement on the release and adhesion tester. The tab should be lifted delicately from the silicone backing sheet and folded slightly forward without making a crease on the label.

If the configuration and set up of the release and adhesion tester being used allows for it, the tab may be folded over onto itself. However, in many cases, the tab will not be long enough to reach the mounting clamp (connected to the force transducer) on the release and adhesion tester. For this scenario, the tab should remain lifted up and away from the silicone backing sheet and uplifted slightly forward without creating a fold or crease on the portion of the label comprising the test strip.

Step 4: Affixing the Label to the Substrate

The analyst shall obtain the intended substrate and wipe it with a lint-free cloth to remove any residues or detritus. The analyst shall carefully remove the entire label from its backing sheet without disturbing the uplifted tab. The analyst will then affix the label onto the substrate in the same position and orientation as it would be done during normal practice and use, except that the tab shall remain unaffixed to the substrate. Examples for each strip type are shown in FIG. 21A-D.

Figure 21A:
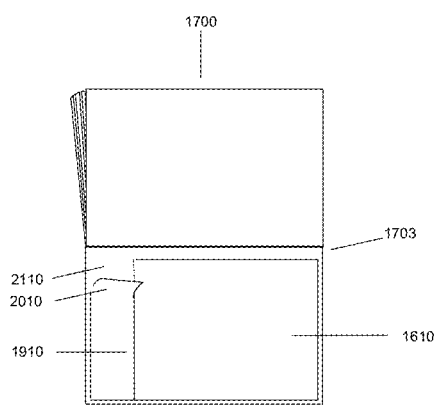
FIG. 21A demonstrates the placement of a label, onto which an edge-to-edge strip has been traced in the machine direction, onto its intended substrate without adhering the tab to the substrate.

In FIG. 21A, edge-to-edge strip 1910, traced onto label 1610, a duplicate of label 1601, has been transferred by the analyst onto the intended substrate, page 2110 of booklet 1700. The top portion of the label is aligned parallel to the spine of booklet 1700, indicated by reference number 1703. Tab 2010 created previously is shown uplifted away from substrate 2110. The remaining portions of label 1610 are to make contact with and adhere to the substrate, booklet page 2110.

Figure 21B:
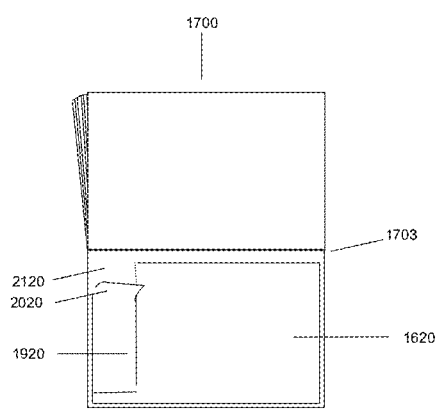
FIG. 21B demonstrates the placement of a label, onto which an edge-to-interior strip has been traced in the machine direction, onto its intended substrate without adhering the tab to the substrate.

In FIG. 21B, edge-to-interior strip 1920, traced onto label 1620, a duplicate of label 1601, has been transferred by the analyst onto the intended substrate, page 2120 of booklet 1700. The top portion of the label is aligned parallel to the spine of booklet 1700, indicated by reference number 1703. Tab 2020 created previously is shown uplifted away from substrate 2120. The remaining portions of label 1620 are to make contact with and adhere to the substrate, booklet page 2120.

Figure 21C:
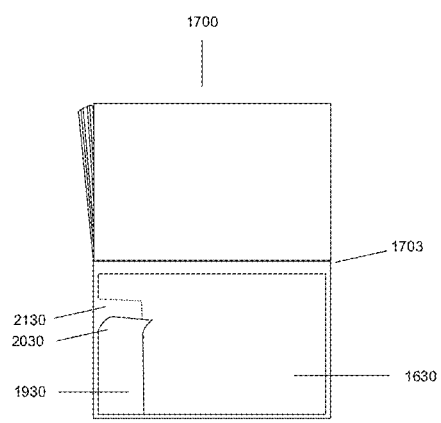
FIG. 21C demonstrates the placement of a label, onto which an interior-to-edge strip has been traced in the machine direction, onto its intended substrate without adhering the tab to the substrate.

In FIG. 21C, interior-to-edge strip 1930, traced onto label 1630, a duplicate of label 1601, has been transferred by the analyst onto the intended substrate, page 2130 of booklet 1700. The top portion of the label is aligned parallel to the spine of booklet 1700, indicated by reference number 1703. Tab 2030 created previously is shown uplifted away from substrate 2130. The remaining portions of label 1630 are to make contact with and adhere to the substrate, booklet page 2130.

Figure 21D:
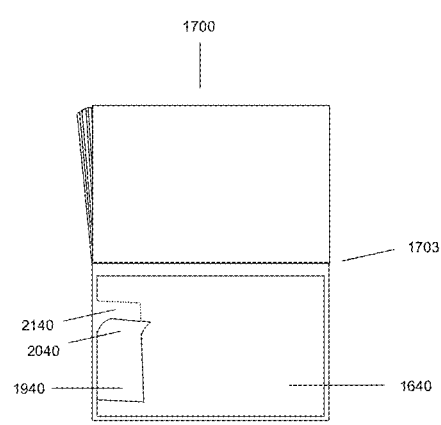
FIG. 21D demonstrates the placement of a label, onto which an interior-to-interior strip has been traced in the machine direction, onto its intended substrate without adhering the tab to the substrate.

In FIG. 21D, interior-to-interior strip 1940, traced onto label 1640, a duplicate of label 1601, has been transferred by the analyst onto the intended substrate, page 2140 of booklet 1700. The top portion of the label is aligned parallel to the spine of booklet 1700, indicated by reference number 1703. Tab 2040 created previously is shown uplifted away from substrate 2140. The remaining portions of label 1640 are to make contact with and adhere to the substrate, booklet page 2140.

The analyst shall then swipe the area of the label affixed to the substrate with a hand applicator, such as the 3M P.A.-1 hand applicator or similar device, held at 90 degrees with respect to the plane in which lies the surface of the non-adhesive side of the label, carefully avoiding contact with the uplifted tab. The label shall be swiped in a total of 8 directions with respect to the orientation of the label (top to bottom, bottom to top, left to right, right to left, bottom right to top left, top right to bottom left, top left to bottom right, bottom left to top right). Care shall be taken by the analyst to avoid contact with the uplifted tab while swiping the label with the hand applicator.

Step 5: Trimming/Removing Excess Substrate

If the portion of the substrate onto which the label is affixed is bound/suspended/attached/connected to a larger array, grouping, or collection, including but not limited to the page of a bound book, then that portion shall be separated from the greater whole by physical means such as cutting or slicing, as shown for each of the four test strip types in FIG. 22A-D.

Any area of the substrate beyond 5 mm of the perimeter of the label should ideally be removed by a cutting device. However, this is not required for purposes of this invention. The process of separating any remaining area of the substrate from the substrate adhering to the label will be performed to reduce the likelihood that a part of the label, or the area of the substrate to which it is affixed, shall be disturbed or damaged. The area of the substrate which remains underneath and exposed by the uplifted tab of the label shall remain part of the test sample strip and should not be cut away, discarded, altered, disturbed, or damaged.

Figure 22A:
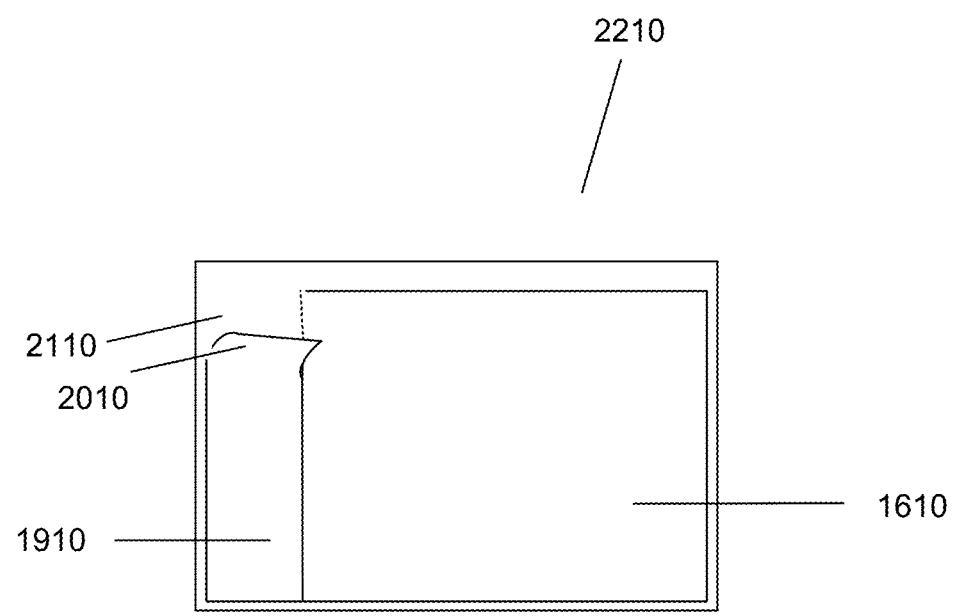
FIG. 22A depicts the label/substrate combination featuring an edge-to-edge traced strip separated from the booklet, with the tab remaining uplifted and not adhered to the substrate.

In FIG. 22A reference number 2210 refers to the indirect method label/substrate combination of label 1610 and substrate booklet page 2110, onto which strip 1910 has been traced and tab 2010 remains uplifted and unaffixed to any other materials, that has been separated by the analyst from booklet 1700 by removing the substrate booklet page 2110 from spine 1703.

Figure 22B:
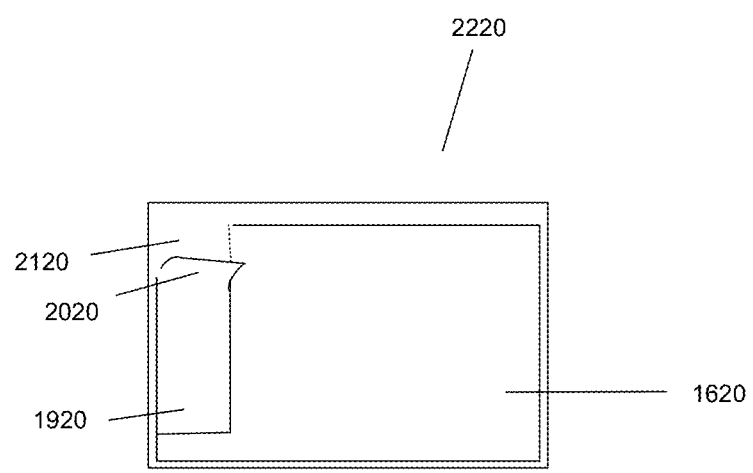
FIG. 22B depicts the label/substrate combination featuring an edge-to-interior traced strip separated from the booklet, with the tab remaining uplifted and not adhered to the substrate.

In FIG. 22B reference number 2220 refers to the indirect method label/substrate combination of label 1620 and substrate booklet page 2120, onto which strip 1920 has been traced and tab 2020 remains uplifted and unaffixed to any other materials, that has been separated by the analyst from booklet 1700 by removing the substrate booklet page 2120 from spine 1703.

Figure 22C:
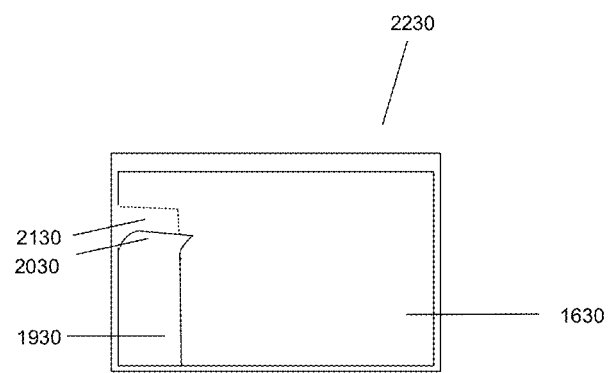
FIG. 22C depicts the label/substrate combination featuring an interior-to-edge traced strip separated from the booklet, with the tab remaining uplifted and not adhered to the substrate.

In FIG. 22C reference number 2230 refers to the indirect method label/substrate combination of label 1630 and substrate booklet page 2130, onto which strip 1930 has been traced and tab 2030 remains uplifted and unaffixed to any other materials, that has been separated by the analyst from booklet 1700 by removing the substrate booklet page 2130 from spine 1703.

Figure 22D:
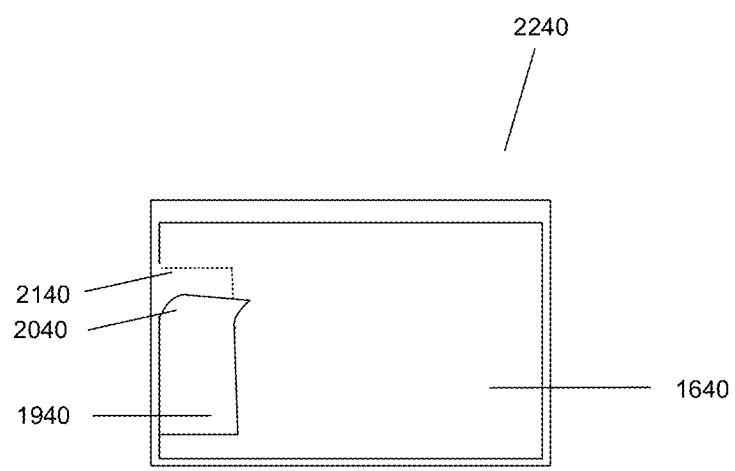
FIG. 22D depicts the label/substrate combination featuring an interior-to-interior traced strip separated from the booklet, with the tab remaining uplifted and not adhered to the substrate.

In FIG. 22D reference number 2240 refers to the indirect method label/substrate combination of label 1640 and substrate booklet page 2140, onto which strip 1940 has been traced and tab 2040 remains uplifted and unaffixed to any other materials, that has been separated by the analyst from booklet 1700 by removing the substrate booklet page 2140 from spine 1703.

Step 6: Adding a "Tail"

A piece of fiber-reinforced tape of a width greater than or equal to the sample test strip's width shall be cut without bias at either end. The length of the tape shall be double the length necessary for the sample to be clamped to the release and adhesion tester for peeling. It is necessary to maintain equal length and width of the tape for all samples to reduce variation in measurement.

One end of the fiber-reinforced tape shall be joined at the full length, d, of the tab such that the adhesive side of the tape along that end is affixed to the adhesive side of the tab. The other end of the fiber-reinforced tape shall adhere to the full length, d, of the printed side of the tab and shall be folded over onto itself to create a "tail" by which the sample test strip will be peeled by the release and adhesion tester.

Figure 23A:
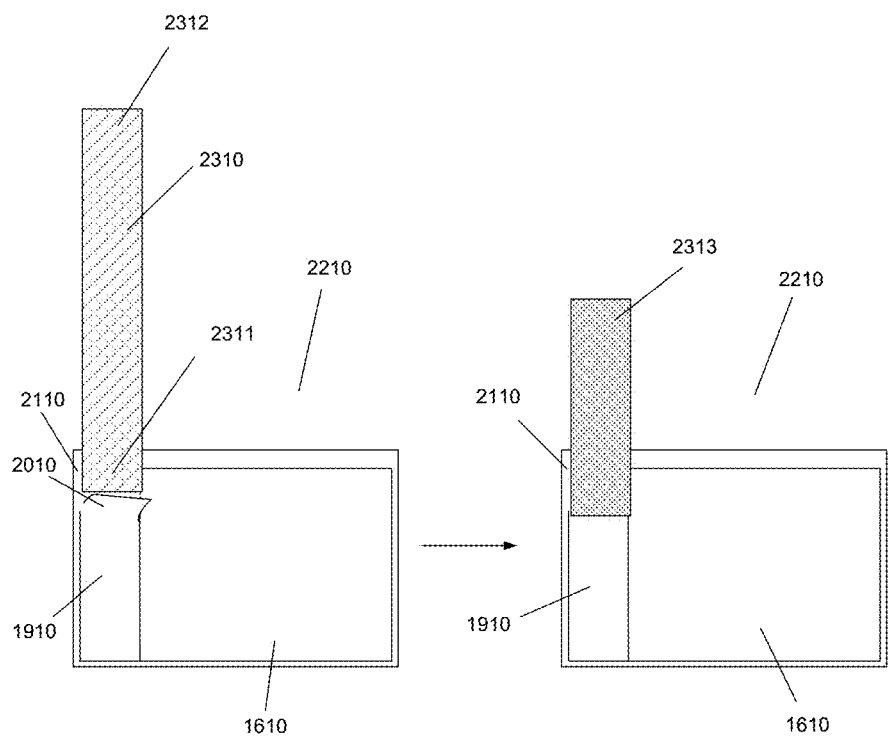
FIG. 23A demonstrates the process of creating a fiber-reinforced tape tail onto the tab of an edge-to-edge traced strip which has not yet been cut away from its originating label/substrate combination.

In FIG. 23A reference number 2310 corresponds to a piece of fiber-reinforced tape conforming to the requirements described above with two opposite ends. The fiber-reinforced tape contains adhesive only on one side. Reference number 2311 corresponds to the first end of fiber-reinforced tape piece 2310, the adhesive side of which is to be affixed to the full length, d, of the adhesive side of tab 2010. Thus, the non-adhesive side of fiber-reinforced tape piece 2310 is adjacent to the area of substrate 2110 which is directly beneath tab 2010 of traced edge-to-edge test strip 1910 of label 1610. Reference number 2312 corresponds to the second end of fiber reinforced tape piece 2310, the adhesive side of which is to be affixed to the full length, d, of tab 2010 on the non-adhesive side of tab 2010. The folding over of fiber reinforced tape piece 2310 onto itself along its adhesive coated surface after the affixation of ends 2311 and 2312 described in the sequence above results in the creation of fiber-reinforced tape tail 2313.

Figure 23B:
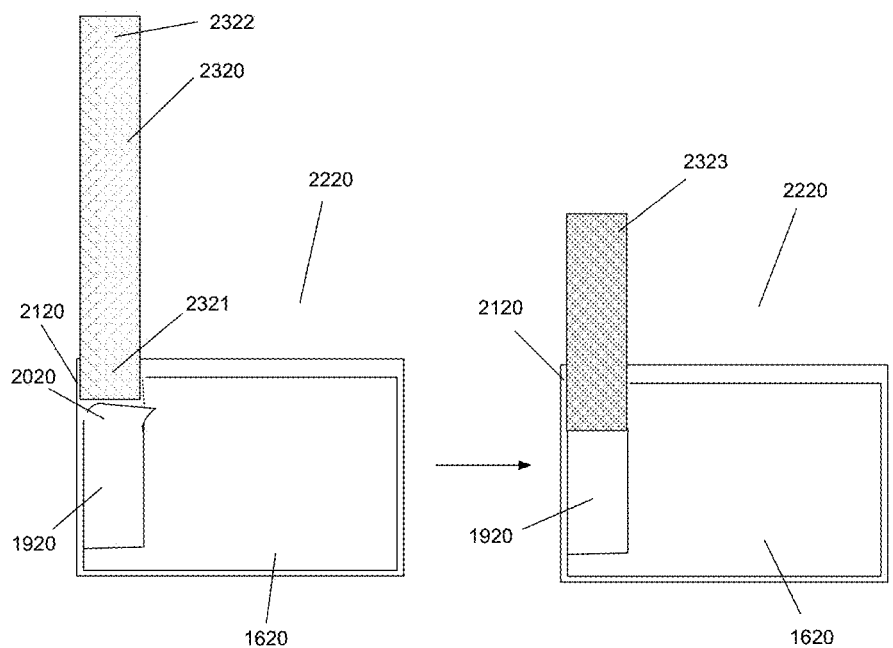
FIG. 23B demonstrates the process of creating a fiber-reinforced tape tail onto the tab of an edge-to-interior traced strip which has not yet been cut away from its originating label/substrate combination.

In FIG. 23B reference number 2320 corresponds to a piece of fiber-reinforced tape conforming to the requirements described above with two opposite ends. The fiber-reinforced tape contains adhesive only on one side. Reference number 2321 corresponds to the first end of fiber-reinforced tape piece 2320, the adhesive side of which is to be affixed to the full length, d, of the adhesive side of tab 2020. Thus, the non-adhesive side of fiber-reinforced tape piece 2320 is adjacent to the area of substrate 2120 which is directly beneath tab 2020 of traced edge-to-interior test strip 1920 of label 1620. Reference number 2322 corresponds to the second end of fiber reinforced tape piece 2320, the adhesive side of which is to be affixed to the full length, d, of tab 2020 on the non-adhesive side of tab 2020. The folding over of fiber-reinforced tape piece 2320 onto itself along its adhesive coated surface after the affixation of ends 2321 and 2322 described in the sequence above results in the creation of fiber-reinforced tape tail 2323.

Figure 23C:
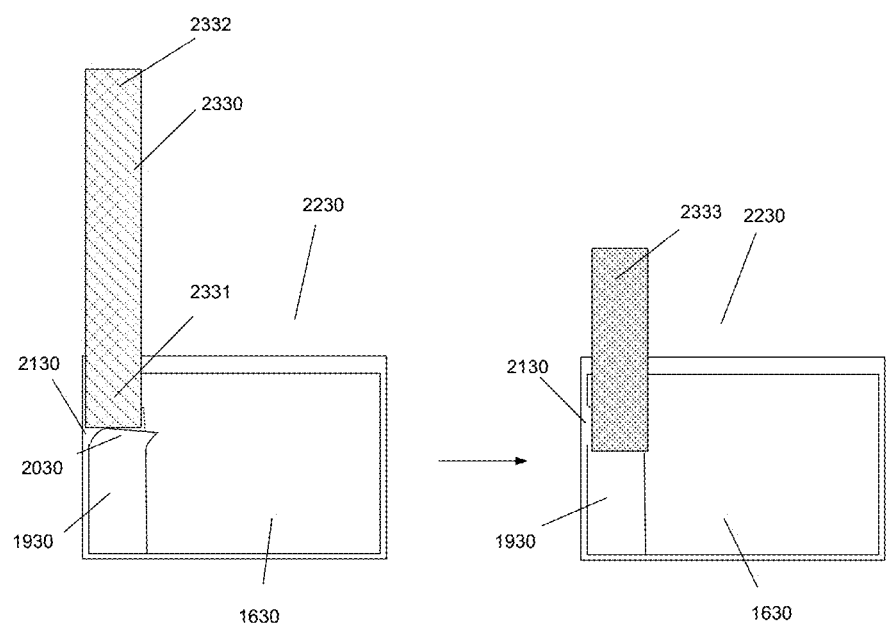
FIG. 23C demonstrates the process of creating a fiber-reinforced tape tail onto the tab of an interior-to-edge traced strip which has not yet been cut away from its originating label/substrate combination.

In FIG. 23C reference number 2330 corresponds to a piece of fiber-reinforced tape conforming to the requirements described above with two opposite ends. The fiber-reinforced tape contains adhesive only on one side. Reference number 2331 corresponds to the first end of fiber-reinforced tape piece 2330, the adhesive side of which is to be affixed to the full length, d, of the adhesive side of tab 2030. Thus, the non-adhesive side of fiber-reinforced tape piece 2330 is adjacent to the area of substrate 2130 which is directly beneath tab 2030 of traced interior-to-interior test strip 1930 of label 1630. Reference number 2332 corresponds to the second end of fiber reinforced tape piece 2330, the adhesive side of which is to be affixed to the full length, d, of tab 2030 on the non-adhesive side of tab 2030. The folding over of fiber reinforced tape piece 2330 onto itself along its adhesive-coated surface after the affixation of ends 2331 and 2332 described in the sequence above results in the creation of fiber-reinforced tape tail 2333.

Figure 23D:
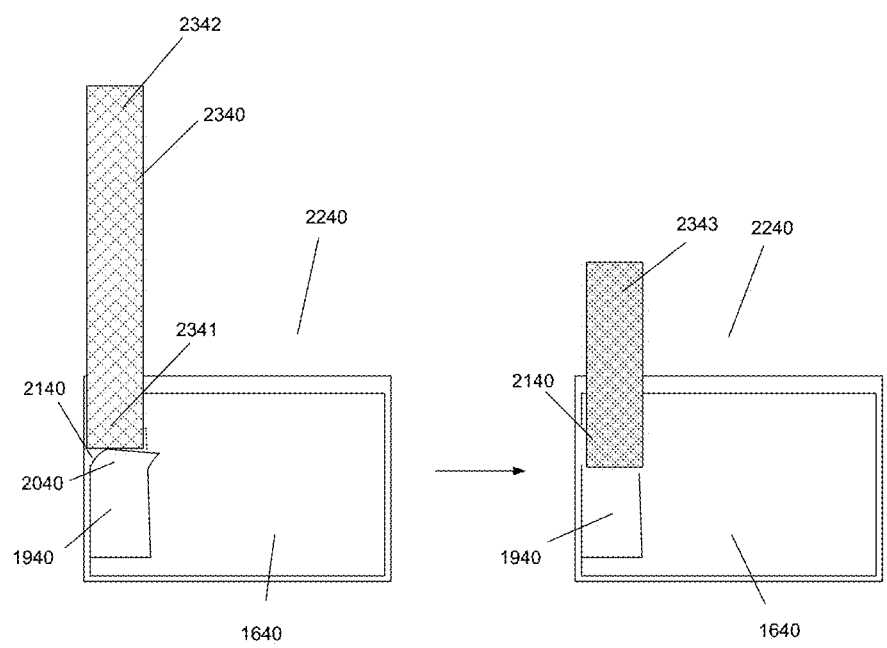
FIG. 23D demonstrates the process of creating a fiber-reinforced tape tail onto the tab of an interior-to-interior traced strip which has not yet been cut away from its originating label/substrate combination.

In FIG. 23D reference number 2340 corresponds to a piece of fiber-reinforced tape conforming to the requirements described above with two opposite ends. The fiber-reinforced tape contains adhesive only on one side. Reference number 2341 corresponds to the first end of fiber-reinforced tape piece 2340, the adhesive side of which is to be affixed to the full length, d, of the adhesive side of tab 2040. Thus, the non-adhesive side of fiber-reinforced tape piece 2340 is adjacent to the area of substrate 2140 which is directly beneath tab 2040 of traced interior-to-interior test strip 1940 of label 1640. Reference number 2342 corresponds to the second end of fiber reinforced tape piece 2340, the adhesive side of which is to be affixed to the full length, d, of tab 2040 on the non-adhesive side of tab 2040. The folding over of fiber reinforced tape piece 2340 onto itself along its adhesive-coated surface after the affixation of ends 2341 and 2342 described in the sequence above results in the creation of fiber-reinforced tape tail 2343.

Step 7: Cutting Away the Test Strip

The sample test strip is cut along the line(s) traced on the label using a rotary cutter, razor blade, or other suitable cutting device.

Step 8: Affixing Double-Sided Tape to the Substrate

Figure 24:
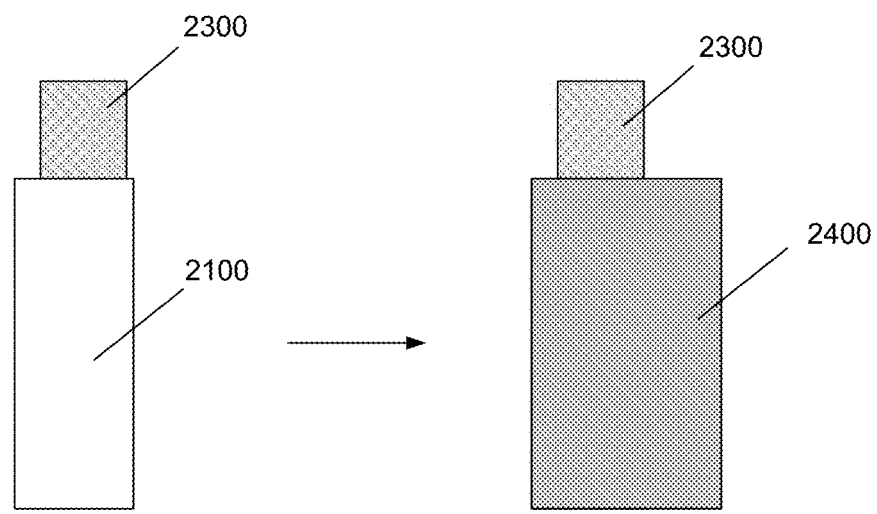
FIG. 24 is a generic representation of the process of affixing double-sided tape to the surface of a cut test strip which bears the substrate.

FIG. 24 depicts the reverse side a generic test strip produced thus far via the indirect method and is composed of two main elements indicated by reference numbers 2300 and 2100. Reference number 2100 corresponds to the area of the reverse side of the substrate which does not bear the traced label strip, and reference number 2300 refers to a fiber reinforced tail attached to the tab created from the traced label strip. The analyst shall cut a strip of suitable strong double-sided table, corresponding to reference number 2400, to accommodate the length of the sample test strip plus any areas of the surrounding substrate 2100. Double-sided tape piece 2400 shall be applied to area 2100 the reverse side of the substrate which does not bear the label. Double-sided tape 2400 shall also be aligned to substrate area 2100 so that there is no over-hang of double-sided tape 2400 near fiber-reinforced tape tail 2300. The analyst shall swipe across the backing sheet of double-sided tape 2400 in all eight directions using the 3M P.A.-1 hand applicator or similar device held at 90 degrees with respect to the plane in which lies the surface of the backing sheet of double-sided tape piece 2400 to ensure proper adhesion between double-sided tape piece 2400 and substrate area 2100. After double-sided tape piece 2400 has been affixed to substrate area 2100, any excess double-sided tape must be cleanly trimmed from the edges of the sample test strip.

Step 9: Applying the Finished Test Strip to a Rigid Testing Plate

After step 8 of the indirect method is completed, the backing sheet of the double-sided tape may be then removed by the analyst, and the sample test strip is then ready to be adhered to a pre-cleaned, rigid plate for mounting onto the release and adhesion tester. The analyst shall use the 3M P.A.-1 hand applicator or similar device held at 90 degrees with respect to the plane in which lies the surface of the non-adhesive side of the prepared sample test strip to ensure proper adhesion of the double-sided tape to the rigid plate. The sample test strip is complete and ready to run. Depending upon the scope of the study, the sample test strip may be exposed to specific atmospheric conditions for a set dwell time before peeling on the release and adhesion tester.

Figure 25:
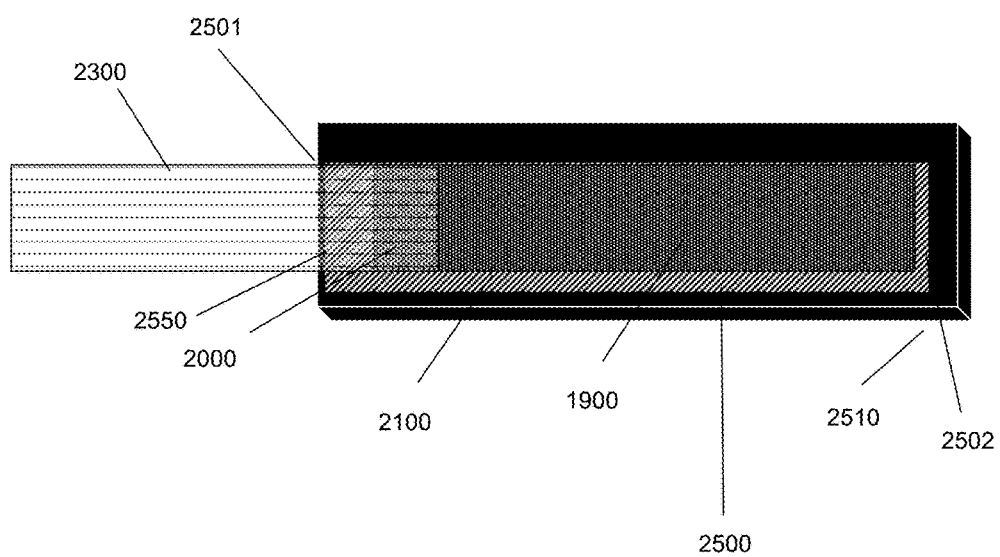
FIG. 25 presents an overview of an edge-to-edge test strip prepared via the indirect method which has been mounted onto a rigid testing plate.

An example of the completed application of a finished edge-to-edge test strip produced via the indirect method onto a rigid testing plate is depicted by FIG. 25. The elements of the finished and mounted test strip 2500 visible in this view include the label 1900 which is adhered to substrate 2100 and from which fiber reinforced tail 2300 has been created from tab 2000. Test strip 2500 is mounted onto rigid testing plate 2510 using double-sided tape which is not visible along this view. Test strip 2500 in FIG. 25 has been mounted to rigid testing plate 2510 such that the position of label 1900 is centered across the width of rigid testing plate 2510 and that the end of test strip 2500 which bears fiber reinforced tape tail 2300, corresponding to reference number 2501, opposite of test strip end 2502, meets edge 2550 of rigid testing plate 2510.

Figure 26:
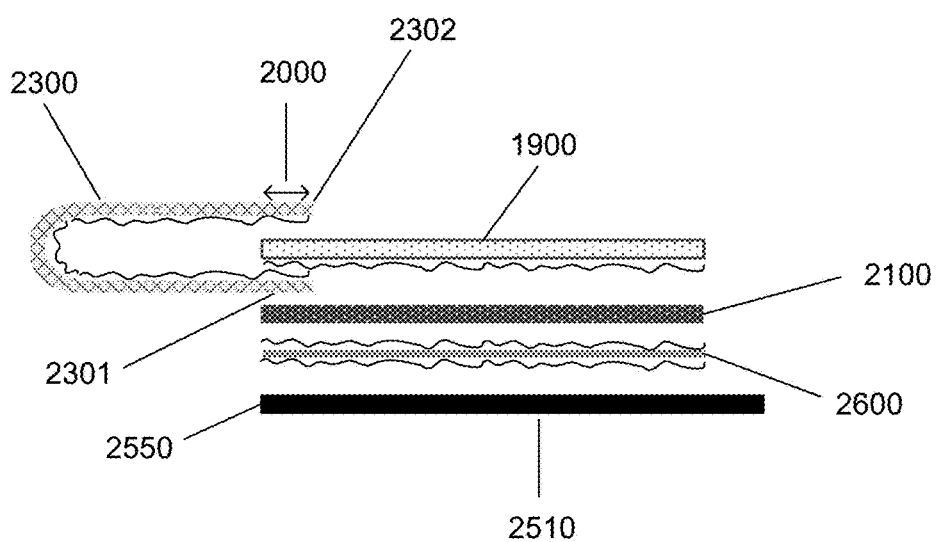
FIG. 26 provides a cross-sectional view through the center of the length of a test strip prepared via the indirect method which has been mounted onto a rigid plate.

FIG. 26 depicts a cross-section of the layers along the length and through the center of a completed test strip as prepared by the indirect method and mounted onto rigid testing plate 2510. This cross-section view allows the placement of double sided tape piece 2600 to be visible as well as the positions of opposite ends 2301 and 2302 of fiber-reinforced tape piece 2300.

Preparation of a Control

Additionally, the sample test strip may be traced and cut from an unprinted area, if one exists, such as unprinted area 1604 of FIG. 16, and applied to the substrate as any of the four test strip types as described previously in steps 1-9 of the indirect method, including the creation of the tail, the application of the double-sided tape, and mounting of the sample test strip onto the rigid test plate. It is recommended to create a strip from an unprinted area in the same dimensions and along the same orientation (machine, cross, or diagonal) as the test strip chosen from the printed label.

If the analyst has access to unprinted "married" rolls from which the labels are created, this may be used to create control test samples. As printing is usually performed in stages, i.e., offset followed by Intaglio, samples can be created from labels obtained from different stages of the print run as well.

Preservation and Archiving of Sample Test Strips

After peeling by the release and adhesion tester is complete, samples may be stored in a neat and orderly fashion by cutting away the excess fiber-reinforced tape tail without removing the tab and affixing the samples with clear, transparent tape onto a clear, colorless, plastic binding cover or similar material. The tape should be applied to both ends of the strip on the non-adhesive side of the label. Care should be taken to properly document the identity of the samples, the sequence in which they were run, and all experimental parameters, including the time and date of the experiment.

Description of the Reverse-Direct Method

The reverse-direct method may be applied to the following types of test strips: "Edge-to-Edge" strips, "Edge-to-Interior" strips, "Interior-to-Edge" strips, and "Interior-to-Interior" strips.

Regardless of the test strip type created, the analyst must wear gloves during all points of sample preparation. This is to prevent the contamination of the adhesive and the surface of the substrate to which the label will be affixed. Once an area of interest on the label has been chosen, strips should be traced using a template of the chosen width and length to ensure uniformity. The template may be aligned against a "landmark" feature along the design of the label to ensure that replicate sample test strips traced from other labels will be identical to each other, as described previously.

Any number of replicate test strips of the same area of investigation may be prepared depending upon the scale of the experiment and the level of statistical confidence sought by the analyst. For a full analysis of the resistance to peel strength of a label, it is recommended that a set of experiments be performed whereby the entire label is sectioned into "edge-to-edge" strips across the machine direction, cross direction, and diagonal directions for a 360 degree analysis as discussed previously in Scenario I.

Step 1: Identifying an Area of the Label to Create a Test Strip

The analyst will identify an area of interest on the label to create a test strip. For one possible embodiment of this step, see Step 1 of the Indirect Method and FIG. 16-17.

Step 2: Tracing the Test Strip with the Template

The analyst will follow the directions given in the Indirect Method, Step 2, and refer to the illustrations in FIG. 18-19 for this step in order to carry on with the embodiment described in the previous step.

Step 3: Creating a Tab

For the reverse-direct method, a tab is still created from the label as shown previously in FIG. 20. However, the properties and function of the tab in the reverse-direct method differ slightly from that in the indirect method.

In the reverse-direct method, the peeling along a test strip will not be performed with tab created from the label. The tab created from the label in the reverse-direct method merely serves to mimic the initiation of the separation between label and substrate. Instead, the peeling along a test strip will be performed by a tab created from the substrate, otherwise known as a substrate tab, which is to be created at a later step.

The length or depth of the tab created from the label portion of the test strip in the reverse-direct method shall range between one-quarter and one-half inch, and the tab created from the label will be lifted slightly away from the silicone backing sheet without creating a crease on the label, similar to the indirect method. Unlike the indirect method, however, the tab created from the label portion of the test strip will undergo further treatment such that it shall be folded over and adhered to itself such that its resultant overall length (depth) is reduced by half, thus, ranging between one-eighth and one-quarter inch. This is demonstrated in FIG. 27A-D, where d refers to the original tab length (depth) ranging from ¼" to ½" and where ½ d refers to the folded over tab length (depth) ranging from ⅛" to ¼".

It is necessary in both the reverse-direct method and the indirect method to maintain a constant tab length among samples in an experimental run to eliminate a possible source of variation in measurement. Likewise, the length of the folded over tab in the reverse-direct method should be kept constant among samples in an experimental run to eliminate a possible source of variation in measurement.

In FIG. 27A-D label tabs corresponding to reference numbers 2710, 2720, 2730, and 2740 have been created previously along their respective test strips traced along duplicates of label 1601 by using a razor blade or similar cutting instrument. Label tabs 2710, 2720, 2730, and 2740 have been cut from the end of the test strip along which the analyst wishes to commence the peel. For strips 2791, 2792, 2793, and 2794 the direction of the peel is assumed to be from the top 1605 to the bottom 1606 along the machine direction 200. It is also assumed that labels 2701, 2702, 2703, and 2704 have not yet been removed or lifted from the sheets onto which they have been printed and die cut.

Figure 27A:
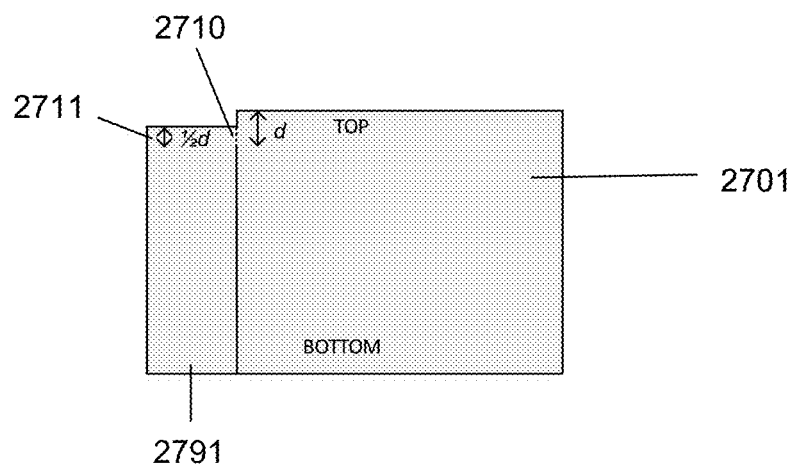
FIG. 27A demonstrates the formation of the folded-over label tab on a PSA label onto which an edge-to-edge test strip has been traced.

In FIG. 27A, edge-to-edge strip 2791 is shown traced onto label 2701, a duplicate of label 1601. Edge-to-edge strip 2791 features label tab 2710 of length (depth) d=¼"-½", which has been folded over and adhered to itself to create folded-over label tab 2711 of length ½d=⅛"-¼".

Figure 27B:
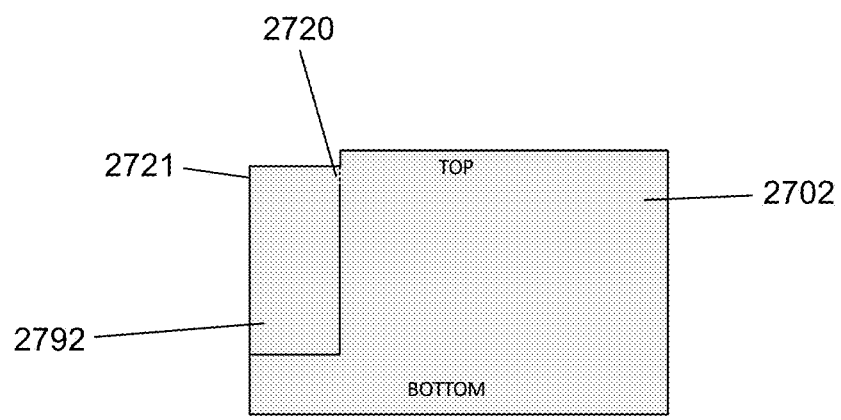
FIG. 27B demonstrates the formation of the folded-over label tab on a PSA label onto which an edge-to-interior test strip has been traced.

In FIG. 27B, edge-to-interior strip 2792 is shown traced onto label 2702, a duplicate of label 1601. Edge-to-interior strip 2792 features label tab 2720 of length (depth) d=¼"-½", which has been folded over and adhered to itself to create folded-over label tab 2721 of length ½d=⅛"-¼".

Figure 27C:
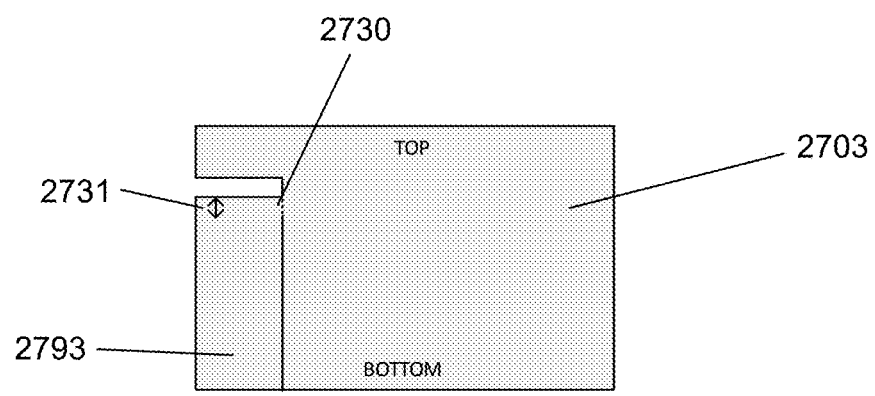
FIG. 27C demonstrates the formation of the folded-over label tab on a PSA label onto which an interior-to-edge test strip has been traced.

In FIG. 27C, interior-to-edge strip 2793 is shown traced onto label 2703, a duplicate of label 1601. Interior-to-edge strip 2793 features label tab 2730 of length (depth) d=¼"–½", which has been folded over and adhered to itself to create folded-over label tab 2731 of length ½d=⅛"–¼".

Figure 27D:
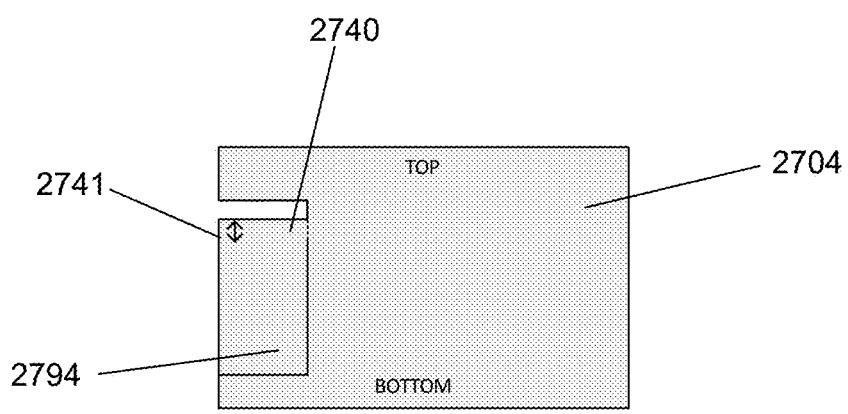
FIG. 27D demonstrates the formation of the folded-over label tab on a PSA label onto which an interior-to-interior test strip has been traced.

In FIG. 27D, interior-to-interior strip 2794 is shown traced onto label 2704, a duplicate of label 1601. Interior-to-edge strip 2794 features label tab 2740 of length (depth) d=¼"–½", which has been folded over and adhered to itself to create folded-over label tab 2741 of length ½d=⅛"–¼".

Step 4: Affixing the Label to the Substrate and Creating a Tab from the Substrate The analyst shall obtain the intended substrate and wipe it with a lint free cloth to remove any residues or detritus. The analyst shall carefully remove the entire label from its backing sheet without disturbing the tab created on the strip traced from the label.

The analyst will then affix the label onto the substrate in the same position and orientation as it would be done during normal practice and use. The tab created on the strip traced onto the label shall remain unaffixed to the substrate due to it previously having been folded over and adhered to itself. Examples for each strip type are shown in FIG. 28A-D.

Figure 28A:
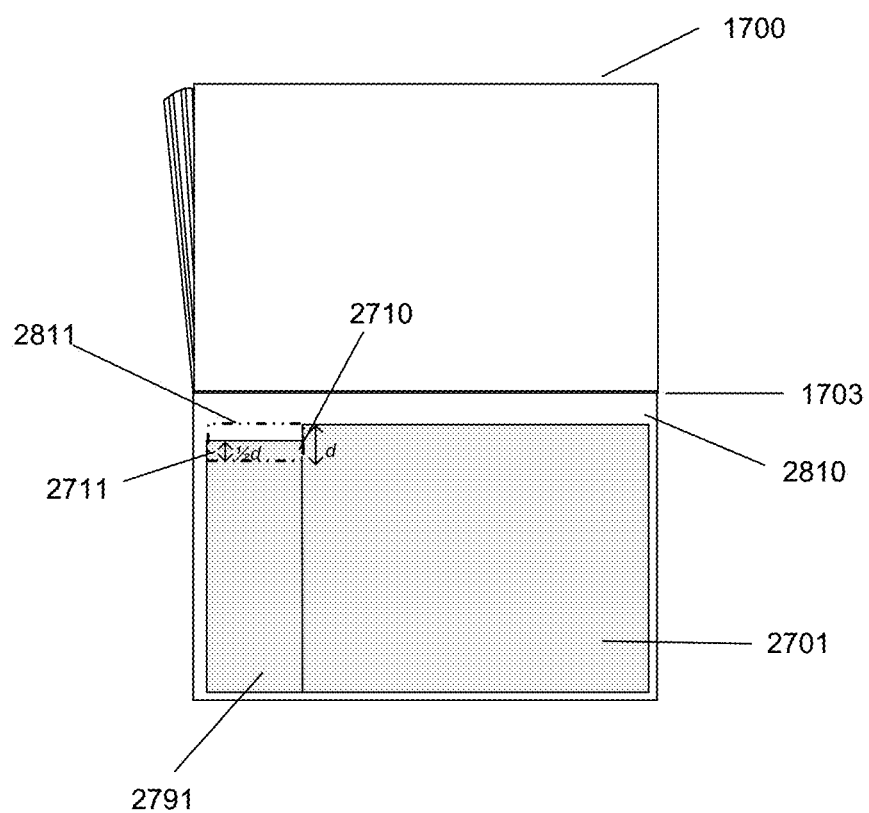
FIG. 28A provides the placement of a label, onto which an edge-to-edge strip has been traced in the machine direction, onto its intended substrate, and indicates the area which is to become the substrate tab for the edge-to-edge test strip.

In FIG. 28A, edge-to-edge strip 2791, traced onto label 2701, a duplicate of label 1601, has been transferred by the analyst onto its intended substrate, page 2810 of booklet 1700. The top portion of label 2701 is aligned parallel to spine 1703 of booklet 1700. Folded-over label tab 2711 is unattached to substrate 2810. The area of substrate 2810 which is partially obscured by the presence of folded-over label tab 2711 is set off by dashed-dotted lines in FIG. 28A. This area of substrate 2810 is to become substrate tab 2811 from which peeling will commence via the reverse-direct method. The depth of substrate tab 2811 is equal to the original depth of label tab 2710 prior to its transformation into folded-over label tab 2711. Therefore, the depth of substrate tab 2811 ranges from ¼" to ½".

Figure 28B:
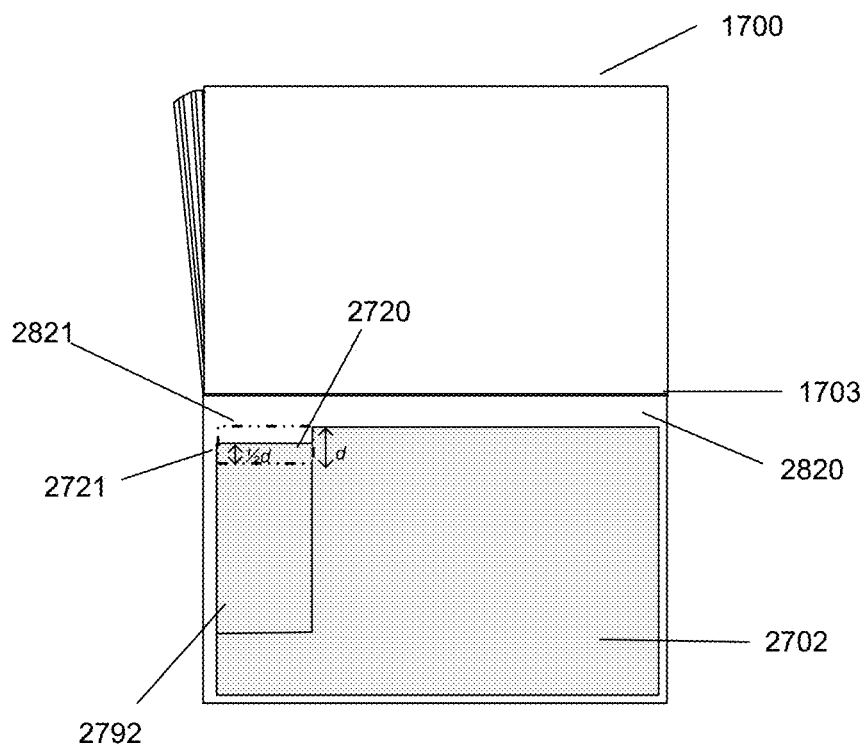
FIG. 28B provides the placement of a label, onto which an edge-to-interior strip has been traced in the machine direction, onto its intended substrate, and indicates the area which is to become the substrate tab for the edge-to-interior test strip.

In FIG. 28B, edge-to-interior strip 2792, traced onto label 2702, a duplicate of label 1601, has been transferred by the analyst onto its intended substrate, page 2820 of booklet 1700. The top portion of label 2702 is aligned parallel to spine 1703 of booklet 1700. Folded-over label tab 2721 is unattached to substrate 2820. The area of substrate 2820 which is partially obscured by the presence of folded-over label tab 2721 is set off by dashed-dotted lines in FIG. 28B. This area of substrate 2820 is to become substrate tab 2821 from which peeling will commence via the reverse-direct method. The depth of substrate tab 2821 is equal to the original depth of label tab 2720 prior to its transformation into folded-over label tab 2721. Therefore, the depth of substrate tab 2821 ranges from ¼" to ½".

Figure 28C:
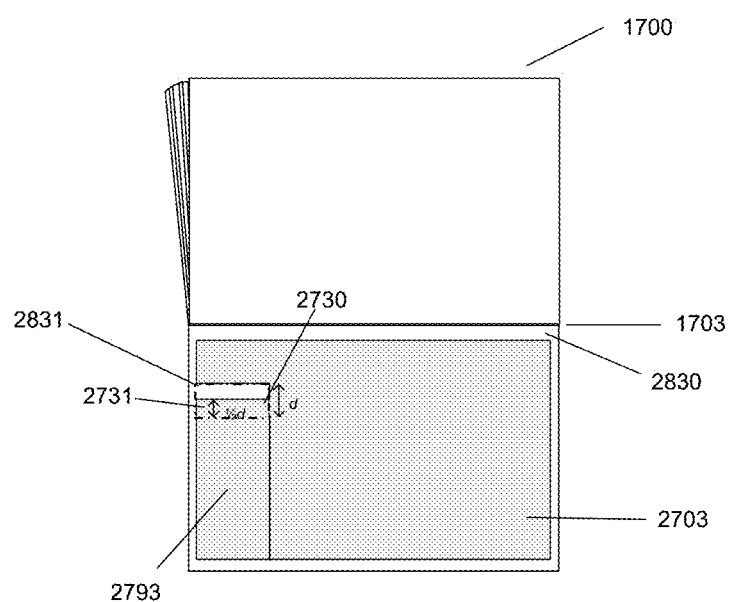
FIG. 28C provides the placement of a label, onto which an interior-to-edge strip has been traced in the machine direction, onto its intended substrate, and indicates the area which is to become the substrate tab for the interior-to-edge test strip.

In FIG. 28C, interior-to-edge strip 2793, traced onto label 2703, a duplicate of label 1601, has been transferred by the analyst onto its intended substrate, page 2830 of booklet 1700. The top portion of label 2703 is aligned parallel to spine 1703 of booklet 1700. Folded-over label tab 2731 is unattached to substrate 2830. The area of substrate 2830 which is partially obscured by the presence of folded-over label tab 2731 is set off by dashed-dotted lines in FIG. 28C. This area of substrate 2830 is to become substrate tab 2831 from which peeling will commence via the reverse-direct method. The depth of substrate tab 2831 is equal to the original depth of label tab 2730 prior to its transformation into folded-over label tab 2731. Therefore, the depth of substrate tab 2831 ranges from ¼" to ½".

Figure 28D:
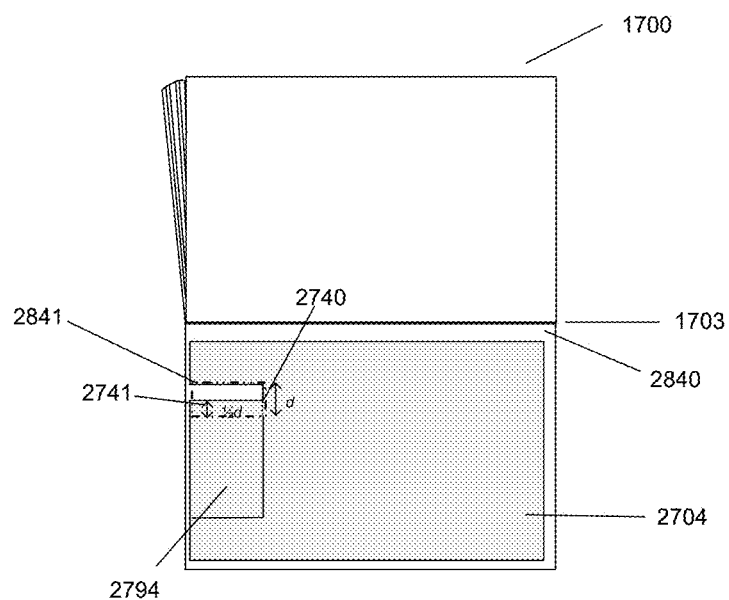
FIG. 28D provides the placement of a label, onto which an interior-to-interior strip has been traced in the machine direction, onto its intended substrate, and indicates the area which is to become the substrate tab for the interior-to-interior test strip.

In FIG. 28D, interior-to-edge strip 2794, traced onto label 2704, a duplicate of label 1601, has been transferred by the analyst onto its intended substrate, page 2840 of booklet 1700. The top portion of label 2704 is aligned parallel to spine 1703 of booklet 1700. Folded-over label tab 2741 is unattached to substrate 2840. The area of substrate 2840 which is partially obscured by the presence of folded over tab 2741 is set off by dashed-dotted lines in FIG. 28C. This area of substrate 2840 is to become substrate tab 2841 from which peeling will commence via the reverse-direct method. The depth of substrate tab 2841 is equal to the original depth of label tab 2740 prior to its transformation into folded over tab 2741. Therefore, the depth of substrate tab 2841 ranges from ¼" to ½".

After applying the label to the substrate by hand, the analyst shall then swipe the area of the label affixed to the substrate with a hand applicator, such as the 3M P.A.-1 hand applicator or similar, held at 90 degrees with respect to the plane in which lies the surface of the non-adhesive side of the label. The label shall be swiped in a total of 8 directions with respect to the orientation of the label (top to bottom, bottom to top, left to right, right to left, bottom right to top left, top left to bottom right, bottom left to top right, top right to bottom left). The analyst shall carefully avoid damaging the tab created on the strip traced onto the label while swiping with the hand applicator. The analyst will also avoid cutting away or damaging the area where the substrate tab is located in steps 5 and 7 to follow.

Step 5: Trimming/Removing Excess Substrate from the Greater Array

If the portion of the substrate onto which the label is affixed is bound/suspended/attached/connected to a larger array, grouping, or collection, including, but not limited to the page of a bound book, then that portion shall be separated from the greater whole by physical means such as cutting or slicing.

Any area of the substrate beyond 5 mm of the perimeter of the label must be removed by a cutting device. If at all possible, it is best to trim as much of the excess substrate away without damaging the label.

The process of separating any remaining area of the substrate from the substrate adhering to the label, hitherto referred to as label/substrate combination, will be performed such that no part of the label, nor the area of the substrate to which it is affixed, shall be disturbed or damaged. The area of the substrate which forms the substrate tab described previously in step 4 shall not be removed, altered, or damaged in any way. If necessary, the analyst is able at this point to remove any portion of excess material immediately above the substrate tab with a suitable cutting instrument. This should be performed in order to proceed with step 6.

FIG. 29A-D provide examples of labels bearing each of the four strip types affixed to the intended substrate (a booklet page), which have been separated (cut away) from the greater array (the booklet). Excess material (label which is bound to substrate and any additional substrate) not part of the substrate tab (area of which is shown within the dashed-dotted lines and partially obscured by the folded-over label tab of the label along the test strip) has been removed.

Figure 29A:
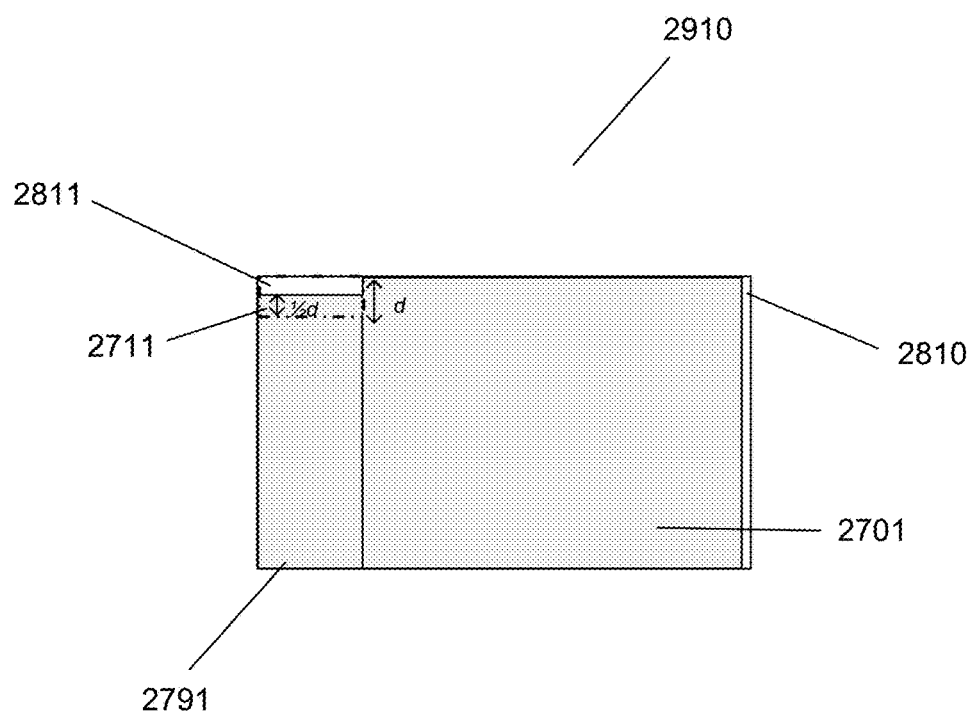
FIG. 29A depicts the label/substrate combination featuring an edge-to-edge traced strip separated from the booklet.

In FIG. 29A reference number 2910 refers to the reverse-direct method label/substrate combination of label 2701, onto which strip edge-to-edge strip 2791 has been traced and label tab 2710 has been transformed into folded-over label tab 2711, and substrate booklet page 2810 separated by the analyst from booklet 1700 by removing substrate booklet page 2810 from spine 1703.

Figure 29B:
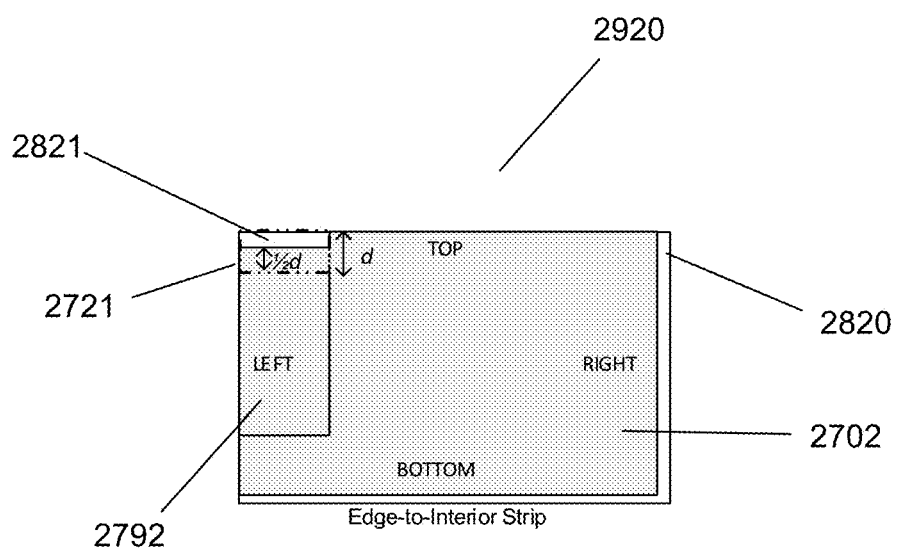
FIG. 29B depicts the label/substrate combination featuring an edge-to-interior traced strip separated from the booklet.

In FIG. 29B reference number 2920 refers to the reverse-direct method label/substrate combination of label 2702, onto which strip edge-to-interior strip 2792 has been traced and label tab 2720 has been transformed into folded-over label tab 2721, and substrate booklet page 2820 separated by the analyst from booklet 1700 by removing substrate booklet page 2820 from spine 1703.

Figure 29C:
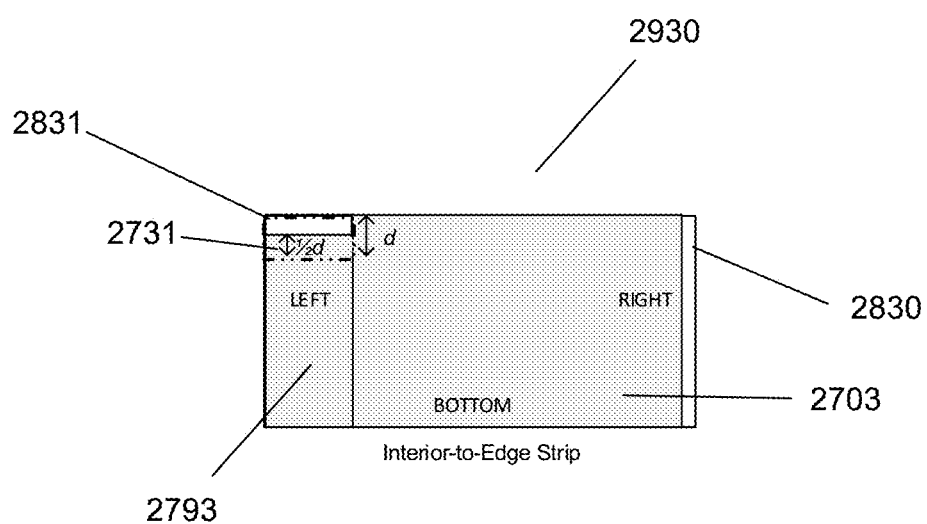
FIG. 29C depicts the label/substrate combination featuring an interior-to-edge traced strip separated from the booklet.

In FIG. 29C reference number 2930 refers to the reverse-direct method label/substrate combination of label 2703, onto which strip interior-to-edge strip 2793 has been traced and label tab 2730 has been transformed into folded-over label tab 2731, and substrate booklet page 2830 separated by the analyst from booklet 1700 by removing substrate booklet page 2830 from spine 1703 and trimming away excess material from along the top edge of substrate tab 2831.

Figure 29D:
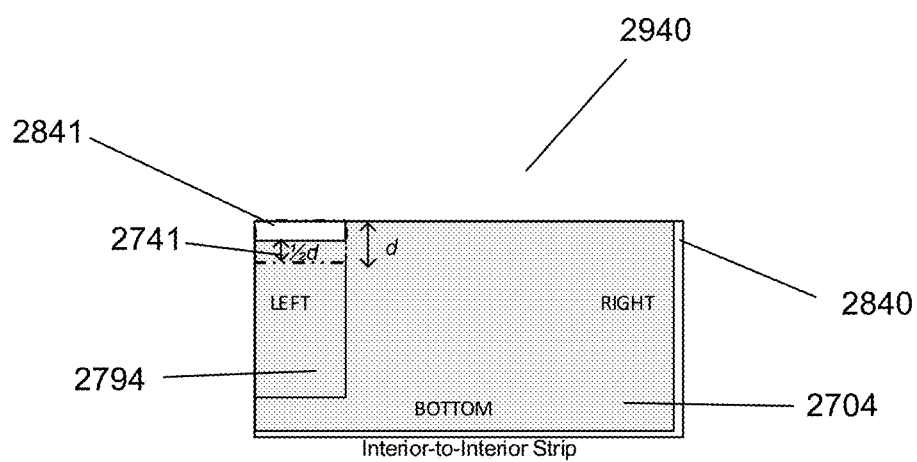
FIG. 29D depicts the label/substrate combination featuring an interior-to-interior traced strip separated from the booklet.

In FIG. 29D reference number 2940 refers to the reverse-direct method label/substrate combination of label 2704, onto which strip interior-to-edge strip 2794 has been traced and label tab 2740 has been transformed into folded-over label tab 2741, and substrate booklet page 2840 separated by the analyst from booklet 1700 by removing substrate booklet page 2840 from spine 1703 and trimming away excess material from along the top edge of substrate tab 2841.

Step 6: Adding a "Tail" to the Substrate Tab

A piece of fiber-reinforced tape of width greater than or equal to the sample test strip width shall be cut without bias at either end. The length of the tape shall be double the length necessary for the sample to be clamped to the release and adhesion tester for peeling. It is necessary to maintain equal length and width of the tape for all samples in an experimental set to reduce variation in measurement.

One end of the fiber-reinforced tape shall be adhered to the full length of the obverse surface of the substrate tab before the second, opposite end is adhered to the reverse surface of the substrate tab. To do this, the tab created from the label must be lifted slightly upwards but without damaging the label tab or any part of what will become the sample test strip. The fiber-reinforced tape shall be folded over onto itself to create a "tail" by which the sample test strip will be peeled by the release and adhesion tester.

Figure 30A:
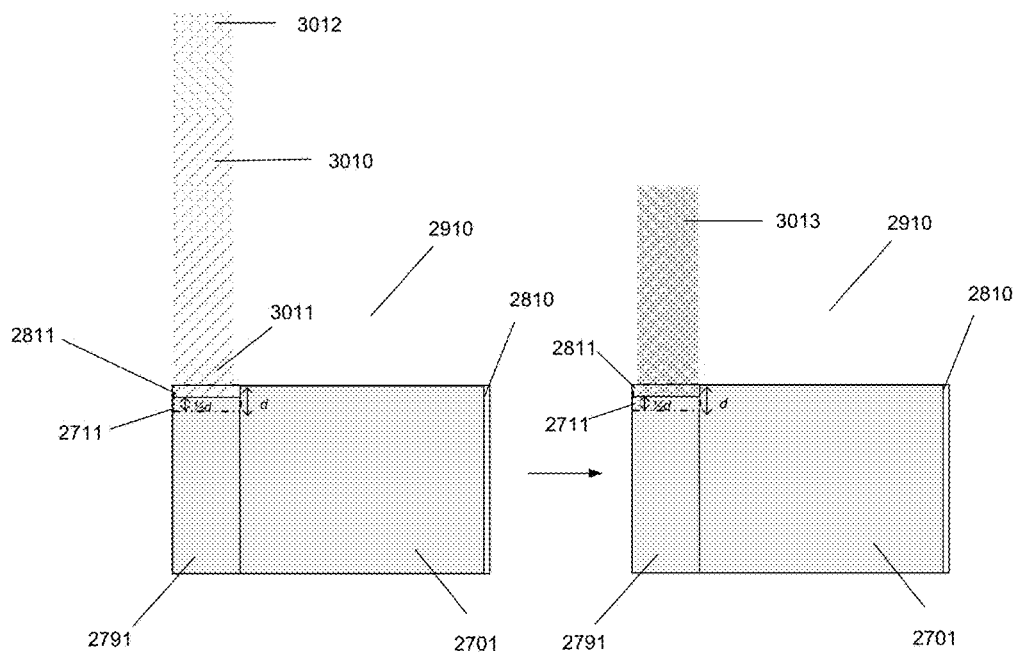
FIG. 30A demonstrates the process of creating a fiber-reinforced tape tail onto the substrate tab of an edge-to-edge traced strip which has not yet been cut away from its originating label/substrate combination.

In FIG. 30A reference number 3010 corresponds to a piece of fiber-reinforced tape conforming to the requirements described above with two opposite ends. The fiber-reinforced tape contains adhesive only on one side. Reference number 3011 corresponds to the first end of fiber-reinforced tape piece 3010, the adhesive side of which is to be affixed to the full length, d, of the obverse face of substrate tab 2811. To accomplish this, it is necessary to uplift folded-over label tab 2711 slightly to allow the adhesive side of tape piece end 3011 to make complete contact along the full length, d, of the obverse face of substrate tab 2811. Thus, the non-adhesive side of tape piece end 3011 is adjacent to folded-over label tab 2711 when tape piece end 3011 is properly affixed to the obverse face of substrate tab 2811. Reference number 3012 corresponds to the second end of fiber-reinforced tape piece 3010, the adhesive side of which is to be affixed to the full length, d, of the reverse face of substrate tab 2811. The folding over of fiber reinforced tape piece 3010 onto itself along its adhesive-coated surface after the previously prescribed affixation of ends 3011 and 3012 results in the creation of fiber reinforced tape tail 3013.

Figure 30B:
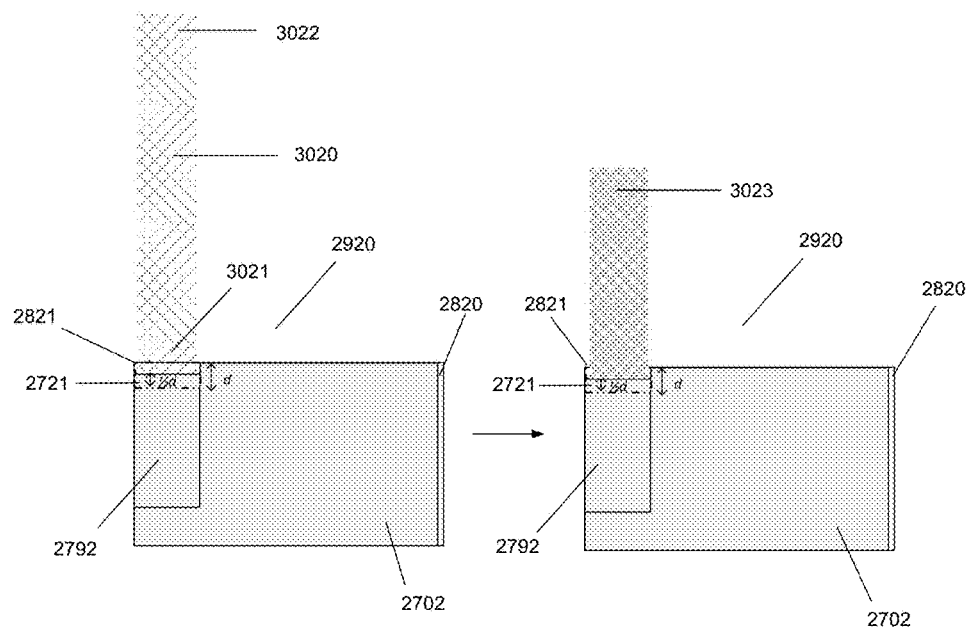
FIG. 30B demonstrates the process of creating a fiber-reinforced tape tail onto the substrate tab of an edge-to-interior traced strip which has not yet been cut away from its originating label/substrate combination.

In FIG. 30B reference number 3020 corresponds to a piece of fiber-reinforced tape conforming to the requirements described above with two opposite ends. The fiber-reinforced tape contains adhesive only on one side. Reference number 3021 corresponds to the first end of fiber-reinforced tape piece 3020, the adhesive side of which is to be affixed to the full length, d, of the obverse face of substrate tab 2821. To accomplish this, it is necessary to uplift folded-over label tab 2721 slightly to allow the adhesive side of tape piece end 3021 to make complete contact along the full length, d, of the obverse face of substrate tab 2821. Thus, the non-adhesive side of tape piece end 3021 is adjacent to folded-over label tab 2721 when tape piece end 3021 is properly affixed to the obverse face of substrate tab 2821. Reference number 3022 corresponds to the second end of fiber-reinforced tape piece 3020, the adhesive side of which is to be affixed to the full length, d, along the reverse face of substrate tab 2821. The folding over of fiber reinforced tape piece 3020 onto itself along its adhesive-coated surface after the previously prescribed affixation of ends 3021 and 3022 results in the creation of fiber reinforced tape tail 3023.

Figure 30C:
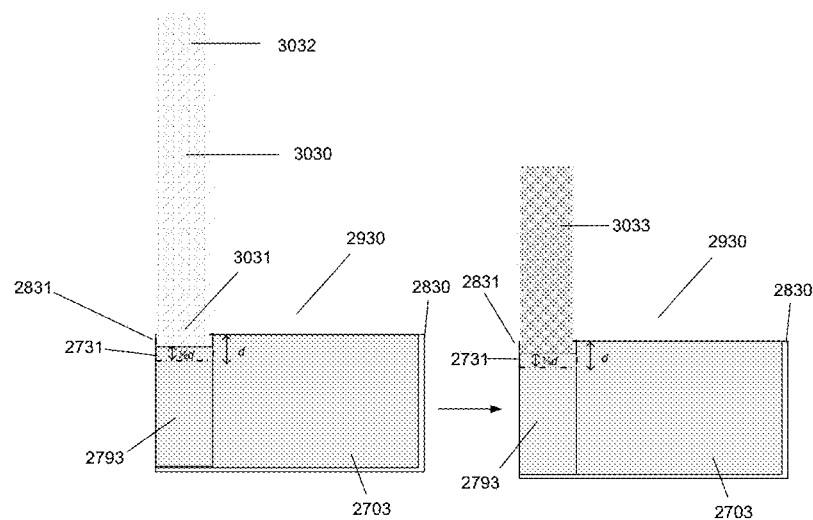
FIG. 30C demonstrates the process of creating a fiber-reinforced tape tail onto the substrate tab of an interior-to-edge traced strip which has not yet been cut away from its originating label/substrate combination.

In FIG. 30C reference number 3030 corresponds to a piece of fiber-reinforced tape conforming to the requirements described above with two opposite ends. The fiber-reinforced tape contains adhesive only on one side. Reference number 3031 corresponds to the first end of fiber-reinforced tape piece 3030, the adhesive side of which is to be affixed to the full length, d, of the obverse face of substrate tab 2831. To accomplish this, it is necessary to uplift folded-over label tab 2731 slightly to allow the adhesive side of tape piece end 3031 to make complete contact along the full length, d, of the obverse face of substrate tab 2831. Thus, the non-adhesive side of tape piece end 3031 is adjacent to folded-over label tab 2731 when tape piece end 3031 is properly affixed to the obverse face of substrate tab 2831. Reference number 3032 corresponds to the second end of fiber-reinforced tape piece 3030, the adhesive side of which is to be affixed to the full length d along the reverse face of substrate tab 2831. The folding over of fiber-reinforced tape piece 3030 onto itself along its adhesive-coated surface after the previously prescribed affixation of ends 3031 and 3032 results in the creation of fiber reinforced tape tail 3033.

Figure 30D:
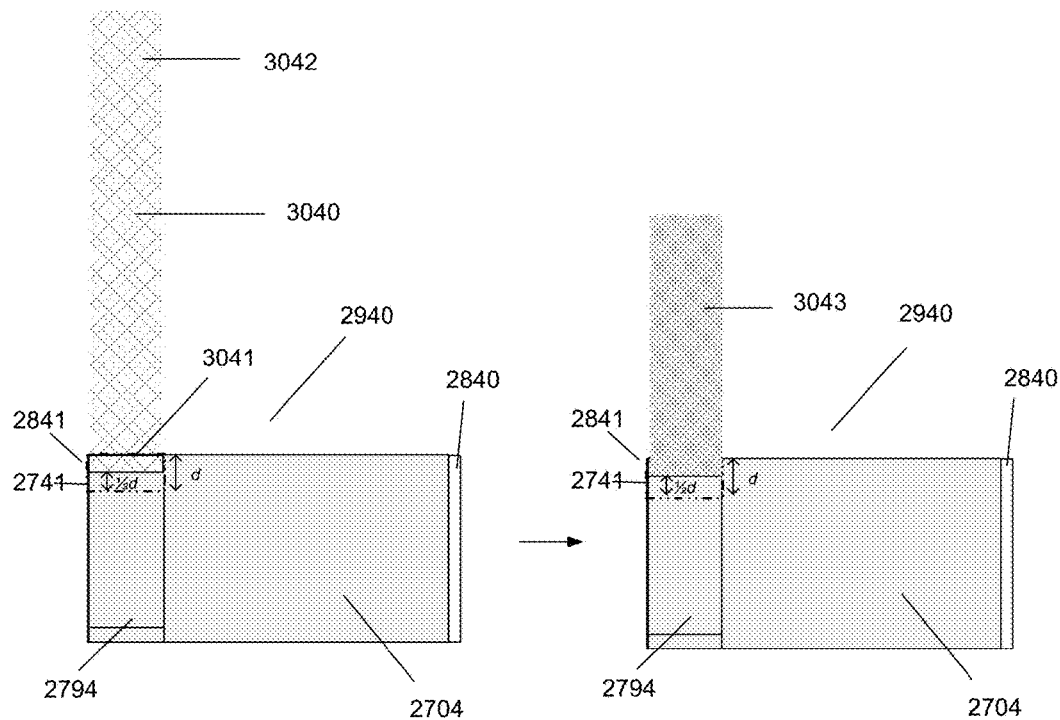
FIG. 30D demonstrates the process of creating a fiber-reinforced tape tail onto the substrate tab of an interior-to-interior traced strip which has not yet been cut away from its originating label/substrate combination.

In FIG. 30D reference number 3040 corresponds to a piece of fiber-reinforced tape conforming to the requirements described above with two opposite ends. The fiber-reinforced tape contains adhesive only on one side. Reference number 3041 corresponds to the first end of fiber-reinforced tape piece 3040, the adhesive side of which is to be affixed to the full length, d, of the obverse face of substrate tab 2841. To accomplish this, it is necessary to uplift folded-over label tab 2741 slightly to allow the adhesive side of tape piece end 3041 to make complete contact with the obverse face of substrate tab 2841. Thus, the non-adhesive side of tape piece end 3041 is adjacent to folded-over label tab 2741 when tape piece end 3041 is properly affixed to the obverse face of substrate tab 2841. Reference number 3042 corresponds to the second end of fiber-reinforced tape piece 3040, the adhesive side of which is to be affixed to the full length, d, along the reverse face of substrate tab 2841. The folding over of fiber reinforced tape piece 3040 onto itself after the previously prescribed affixation of ends 3041 and 3042 results in the creation of fiber reinforced tape tail 3043.

Step 7: Cutting Away the Test Strip

The sample test strip is cut along the line(s) traced on the label using a rotary cutter, razor blade, or other suitable cutting instrument. The test strip shall include the substrate tab created underneath the folded over label tab. It is necessary to maintain the same length and position of each substrate tab for all samples within an experiment to eliminate a potential source of variation in measurement. FIG. 31A-D depict examples of each strip type cut away from the label/substrate combinations from which each strip was formed with the label face stock facing out. It is onto the label face stock that the double-sided tape will be applied in step 8.

Step 8: Affixing the Double-Sided Tape to the Label Face Stock

The analyst shall cut a strip of suitably strong double-sided tape to accommodate the length of the sample test strip. In the reverse-direct method the double-sided tape shall be applied to the label face stock rather than the reverse (or back) side of the substrate as prescribed by the indirect method. Therefore, the length of the double-sided tape should be equal to the distance from the edge of the folded over tab to the edge of the cut test strip. The double-sided tape shall be aligned to the label so that there is no overhang of the double-sided tape near the fiber-reinforced tape or along the edges of the test strip, as shown in FIG. 31A-D. Any overhang shall be trimmed away neatly using a razor blade or other suitable cutting device.

Figure 31A:
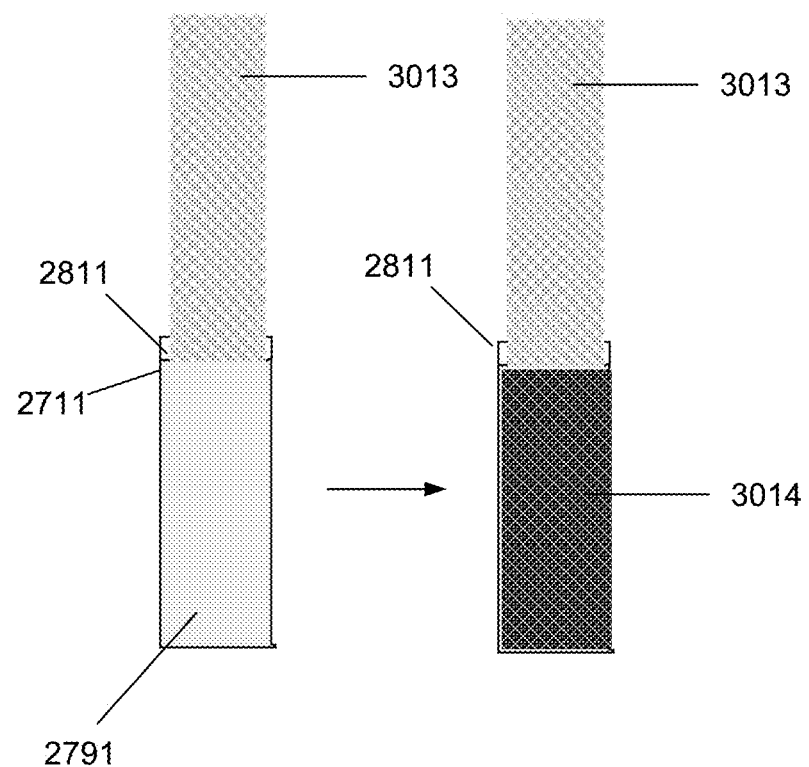
FIG. 31A depicts the placement of double-sided tape onto the surface of an edge-to-edge test strip which bears the label face stock.

In FIG. 31A, the analyst will measure the distance from the edge of folded-over tab 2711 to the bottom edge of strip 2791 to determine the length of double-sided tape required to adhere to the surface of test strip 2791 bearing the face stock of label 2701. Reference number 3014 corresponds to a suitably sized piece of double-sided tape with its backing sheet in place which has been affixed to the label face stock portion of test strip 2791 that encompasses the distance from folded-over tab 2711 to the bottom end of the test strip. No portion of double-sided tape piece 3014 is adhered to fiber-reinforced tape tail 3013.

Figure 31B:
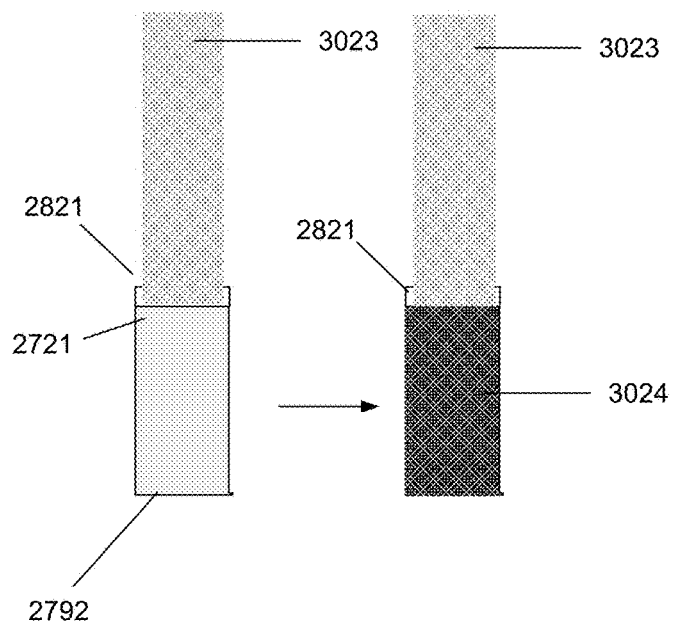
FIG. 31B depicts the placement of double-sided tape onto the surface of an edge-to-interior test strip which bears the label face stock.

In FIG. 31B, the analyst will measure the distance from the edge of folded-over tab 2721 to the bottom edge of strip 2792 to determine the length of double-sided tape required to adhere to the surface of test strip 2792 bearing the face stock of label 2702. Reference number 3024 corresponds to a suitably sized piece of double-sided tape with its backing sheet in place which has been affixed to the label face stock portion 2702 of test strip 2792 that encompasses the distance from folded-over tab 2721 to the bottom end of the test strip. No portion of double-sided tape piece 3024 is adhered to fiber-reinforced tape tail 3023.

Figure 31C:
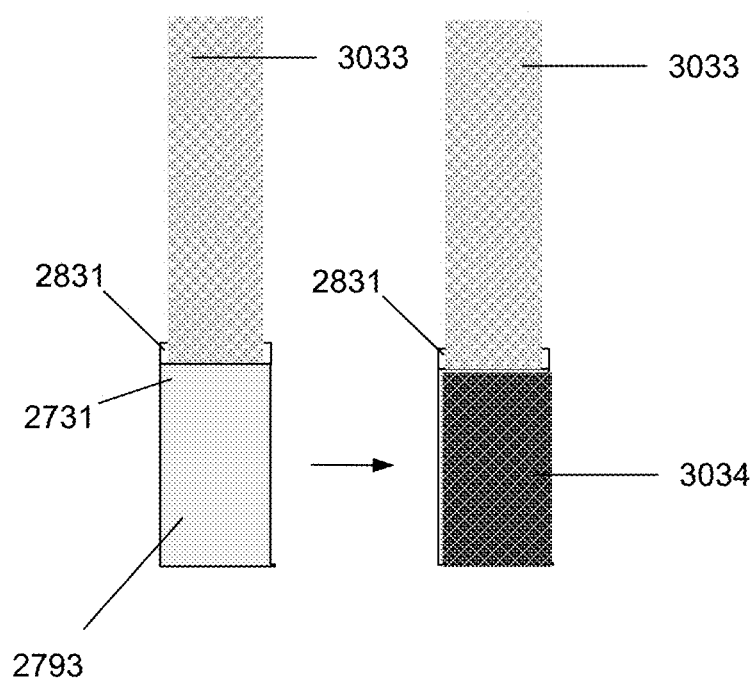
FIG. 31C depicts the placement of double-sided tape onto the surface of an interior-to-edge test strip which bears the label face stock.

In FIG. 31C, the analyst will measure the distance from the edge of folded-over tab 2731 to the bottom edge of strip 2793 to determine the length of double-sided tape required to adhere to the surface of test strip 2793 bearing the face stock of label 2703. Reference number 3034 corresponds to a suitably sized piece of double-sided tape with its backing sheet in place which has been affixed to the label face stock portion 2703 of test strip 2793 that encompasses the distance from folded-over tab 2731 to the bottom end of the test strip. No portion of double-sided tape piece 3034 is adhered to fiber-reinforced tape tail 3033.

Figure 31D:
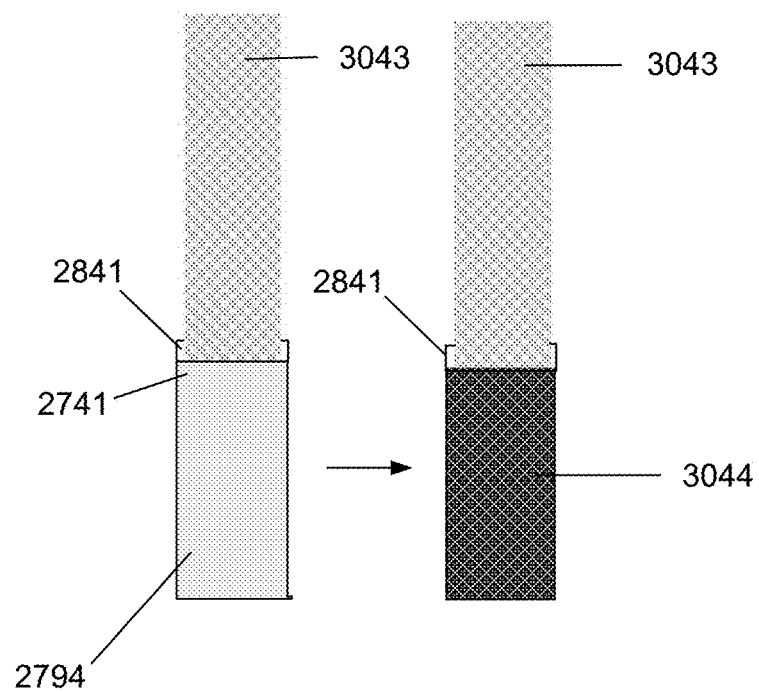
FIG. 31D depicts the placement of double-sided tape onto the surface of an interior-to-interior test strip which bears the label face stock.

In FIG. 31D, the analyst will measure the distance from the edge of folded-over tab 2741 to the bottom edge of strip 2794 to determine the length of double-sided tape required to adhere to the surface of test strip 2794 bearing the face stock of label 2704. Reference number 3044 corresponds to a suitably sized piece of double-sided tape with its backing sheet in place which has been affixed to the label face stock portion of test strip 2794 that encompasses the distance from folded-over tab 2741 to the bottom end of the test strip. No portion of double-sided tape piece 3044 is adhered to fiber-reinforced tape tail 3043.

After the application of the double-sided tape is complete, the analyst shall swipe across the backing sheet of the double-sided tape in all eight directions using the handheld applicator held at 90 degrees with respect to the plane in which lies the surface of the backing sheet of the double-sided tape to ensure proper adhesion between the double-sided tape to the label face stock.

Step 9: Applying the Finished Test Strip to a Rigid Testing Plate

The backing sheet of the double-sided tape may then be removed by the analyst, and the sample test strip is ready to be adhered to a pre-cleaned, rigid plate for mounting onto the release and adhesion tester. The sample test strip shall be centered along the top edge of the plate, as shown in FIG. 32 and in FIG. 33.

The analyst shall use the 3M P.A.-1 hand applicator or similar device held at 90 degrees with respect to the plane in which lies the surface of the non-adhesive side of the prepared sample test strip to ensure proper adhesion of the double-sided tape to the rigid plate. The sample test strip is complete and ready to run. Depending upon the scope of the study, the sample test strip may be exposed to specific atmospheric conditions for a set dwell time before being peeled on the release and adhesion tester.

Figure 32:
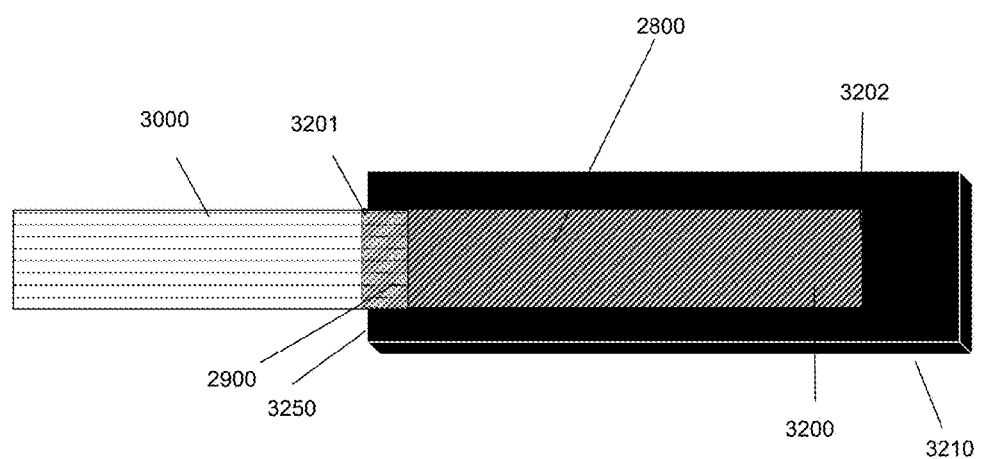
FIG. 32 presents an overview of a test strip prepared via the reverse-direct method which has been mounted onto a rigid testing plate.

An example of the completed application of a finished edge-to-edge test strip produced via the reverse-direct method onto a rigid testing plate is depicted by FIG. 32. The elements of finished and mounted test strip 3200 visible in this view include substrate 2800, substrate tab 2900, and fiber-reinforced tail 3000, which has been created from substrate tab 2900.

Test strip 3200 has been mounted to rigid testing plate 3210 such that the position of the strip is centered across the width of rigid testing plate 3210 and that end 3201 of test strip 3200 which bears fiber-reinforced tail 3000 meets edge 3250 of plate 3210.

Figure 33:
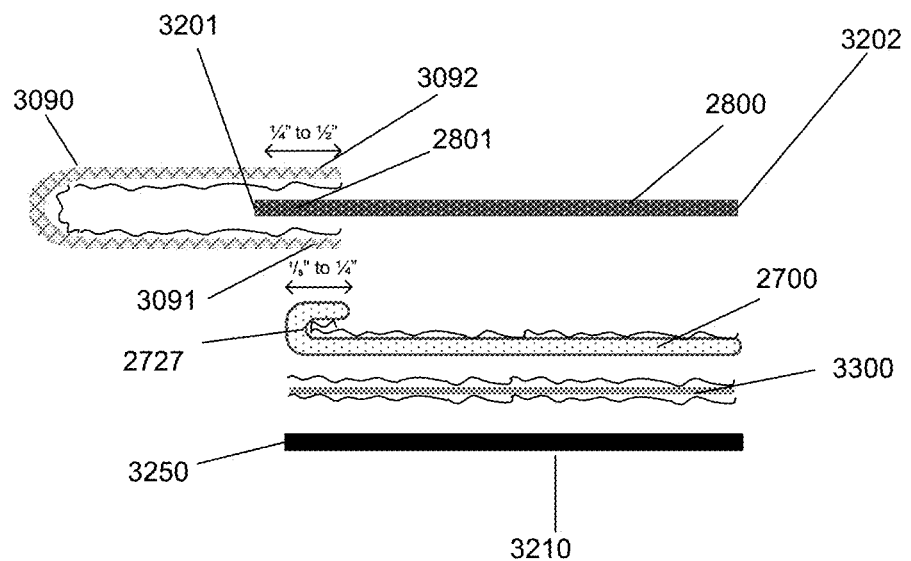
FIG. 33 provides a cross-sectional view through the center of the length of a test strip prepared via the reverse-direct method which has been mounted onto a rigid plate.

FIG. 33 depicts a cross section of the layers along the length and through the center of a completed test strip as prepared by the reverse-direct method which has been mounted onto rigid testing plate 3210. This cross-sectional view allows the placement of double-sided tape piece 3300 to be visible, as well as the positions of opposite ends 3091 and 3092 of the fiber-reinforced tape tail created from fiber-reinforced tape piece 3090 and substrate tab 2801. Also visible in this view is folded-over label tab 2727 created from the strip traced from label 2700. End 3201, opposite of end 3202 of the completed test strip, bears the substrate tab and fiber-reinforced tape tail and is aligned and centered with edge 3250 of plate 3210.

Preparation of a Control

Additionally, the sample test strip may be traced and cut from an unprinted area of the label, if one exists, and applied to the substrate as any of the four test strip types as described previously in steps 1-9 of the reverse-direct method, including the creation of the tail, the application of the double-sided tape, and mounting of the sample test strip onto the rigid test plate. It is recommended to create a strip from an unprinted area in the same dimensions and along the same orientation (machine, cross, or diagonal) as the test strip chosen from the printed label.

If the analyst has access to unprinted "married" rolls from which the labels are created, this may be used to create control test samples. As printing is usually performed in stages, i.e., offset followed by Intaglio, samples can be created from labels obtained from different stages of the print run as well.

Preservation and Archiving of Sample Test Strips

After peeling by the release and adhesion tester is complete, samples may be stored in a neat and orderly fashion by cutting away the excess fiber-reinforced tape tail without removing the tab and affixing the samples with clear, transparent tape onto a clear, colorless, plastic binding cover or similar material. The tape should be applied to both ends of the strip on the reverse side of the substrate. Care should be taken to properly document the identity of the samples, the sequence in which they were run, and all experimental parameters, including the time and date of the experiment.

A Note on Tabs

Figure 34:
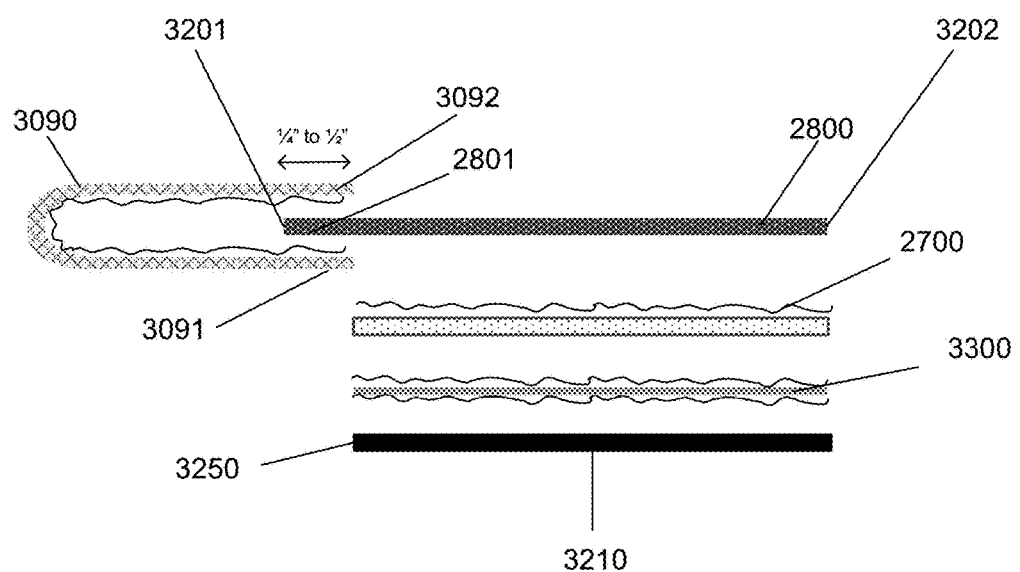
FIG. 34 provides a cross-sectional view through the center of the length of a test strip, which is either an edge-to-edge or edge-to-interior test strip, prepared via the reverse-direct method and without the formation of a folded-over label tab that has been mounted onto a rigid plate.

For edge-to-edge and edge-to-interior strips only:

If the analyst is interested in observing the peeling behavior and in determining the resistance to peel strength required to separate the substrate away from the label beginning from the edge of the strip, a tab may be created from an area of the substrate the same width as the test strip and of a length of one-fourth to one-half inch beyond the perimeter of the label from which the peeling is to commence, if such an area is available along the substrate. The analyst shall follow the steps of this procedure to produce a finished and mounted test strip, as shown in cross section by FIG. 34. The arrangement and positioning of the elements in FIG. 34 are best contrasted with those shown in FIG. 33.

Selection of a Double-Sided Tape

For the analyst to conduct a successful investigation of the resistance to peel strength of a label, the double-sided tape which is used to mount the test strip (either prepared in the Indirect Method or the Reverse-Direct Method) must be sufficiently strong to maintain the position of the test strip on the rigid testing plate during peeling. Often the only way to know if a double-sided tape is strong enough is through trial and error on actual test strips. If a test strip is being pulled away from the double-sided tape or if a test strip, including the double-sided tape, is being pulled away from the rigid testing plate as the peel experiment is running, then the double-sided tape lacks sufficient adhesive strength, assuming the analyst has observed protocol while preparing the test strip.

Just as in the preparation of test strips, during the analysis and selection process of a double-sided tape, the analyst shall wear gloves at all times, and the rigid testing plates used shall be clean and free of oils, adhesive, or any debris.

A strip of double-sided tape shall be cut one inch longer than the length of the rigid testing plate. The width of the double-sided tape shall match the width of the template used to create the test strips. The double-sided tape shall be mounted and centered onto a clean, rigid testing plate with the backing sheet still in place. The one-inch (1") overhang shall be located on the end from which the peeling will commence.

The analyst shall swipe the double-sided tape in eight directions (top to bottom, bottom to top, left to right, right to left, upper left to lower right, lower right to upper left, upper right to lower left, lower left to upper right) using a 3M P.A.-1 hand held applicator or similar device held at 90 degrees with respect to the plane in which lies the surface of the backing sheet of the double-sided tape to ensure proper contact and adhesion of the double-sided tape to the rigid testing plate.

Figure 35:
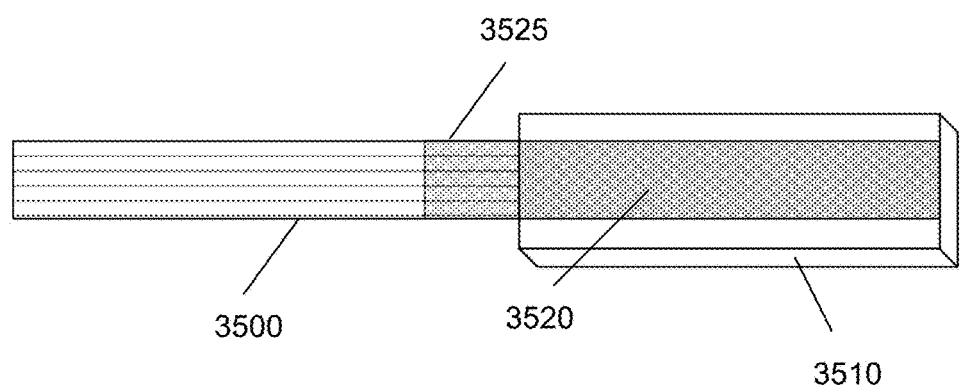
FIG. 35 presents an overview of a replicate of a double-sided tape piece mounted onto a rigid testing plate and fitted with a fiber reinforced tail for the purpose of determining the resistance to peel strength of the double-sided tape from the surface of the rigid testing plate.

Onto the 1" overhang the analyst shall adhere the adhesive side of a piece of fiber-reinforced tape onto the exposed adhesive side of the double-sided tape. The analyst shall then remove the backing sheet from the double-sided tape and continue to fold the fiber-reinforced tape over itself such that the other end of the fiber-reinforced tape covers the newly exposed side of the 1" overhang. A completed replicate is shown in FIG. 35 showing the assembly of the following elements: fiber-reinforced tape tail 3500, rigid testing plate 3510, double-sided tape piece 3520, and overhanging portion of double-sided tape piece equal to one-inch in length 3525.

The length of the fiber-reinforced tape tail shall be consistent with the length used in actual sample test strips. The analyst shall then mount the rigid testing plate onto the release and adhesion tester and perform the peel under the same conditions as a sample test strip. Five replicates will provide sufficient data to the analyst on the resistance to peel force of the double sided tape being peeled away from the rigid testing plate and whether the tape is suitable for the preparation of test strips.

It is advised that the analyst be consistent in product use for all consumables, including double sided tape and fiber-reinforced tape, to prevent the introduction of experimental variation.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining adhesive strength comprising:
   providing a label having an adhesive layer on a first surface and a second surface opposite the first surface;
   providing a substrate having a first surface and a second surface opposite the first surface;
   affixing a portion of the adhesive layer on the first surface of the label to the first surface of the substrate;
   forming a tab portion on the label from a portion of the label not affixed to the substrate;
   affixing a tail to the tab portion, the tail being configured to receive a pulling force;
   forming a label test strip from the label;
   affixing an adhesive layer to the second surface of the substrate;
   affixing the adhesive layer on the second surface of the substrate to a test plate;
   peeling the label test strip away from the substrate by pulling the tail away from the substrate; and
   measuring the force required to peel the label test strip from the substrate;
   wherein the label has a machine direction and a cross direction and wherein the label test strip is formed so as to extend along a line at an angle to the machine direction or cross direction and the angle is some angle other than 0 degrees, 90 degrees, 180 degrees, 270 degrees, or 360 degrees.

2. The method of claim 1, wherein the label has an original shape defined by an edge and wherein the label test strip is sized to extend from one edge to another edge of the original label shape.

3. The method of claim 1, wherein the label has an original shape defined by an edge and wherein the label test strip is sized to extend from one edge to an interior of the original label shape.

4. The method of claim 1, wherein the label has an original shape defined by an edge and wherein the label test strip is sized to extend from an interior to an edge of the original label shape.

5. The method of claim 1, wherein the label has an original shape defined by an edge and wherein the label test strip is sized to extend from an interior to another portion of the interior of the original label shape.

6. The method of claim 1 further comprising:
providing a new label having an adhesive layer on a first surface and a second surface opposite the first surface, wherein the adhesive on the first surface is the same adhesive as that recited for the first surface of the label in claim 1;
providing a new substrate having a first surface and a second surface opposite the first surface;
affixing a portion of the adhesive layer on the first surface of the new label to the first surface of the new substrate;
forming a new tab portion on the new substrate from a portion of the new substrate not affixed to the new label;
affixing a new tail to the new tab portion, the new tail being configured to receive a pulling force;
forming a substrate test strip from the new substrate;
affixing an adhesive layer to a second surface of the new label;
peeling the substrate test strip away from the new label by pulling the new tail away from the new label; and
measuring the force required to peel the substrate test strip from the new label.

7. The method of claim 1, wherein the label test strip is peeled away from the substrate along an angle relative to a machine or cross direction of the label and the angle is some angle other than 0 degrees, 90 degrees, 180 degrees, 270 degrees, or 360 degrees.

\* \* \* \* \*